United States Patent
Shoshan-Barmatz et al.

(10) Patent No.: US 10,508,091 B2
(45) Date of Patent: *Dec. 17, 2019

(54) PIPERAZINE AND PIPERIDINE DERIVATIVES, THEIR SYNTHESIS AND USE THEREOF IN INHIBITING VDAC OLIGOMERIZATION, APOPTOSIS AND MITOCHONDRIA DYSFUNCTION

(71) Applicant: THE NATIONAL INSTITUTE FOR BIOTECHNOLOGY IN THE NEGEV LTD., Beer-Sheva (IL)

(72) Inventors: Varda Shoshan-Barmatz, Omer (IL); Arie Lev Gruzman, Jerusalem (IL)

(73) Assignee: THE NATIONAL INSTITUTE FOR BIOTECHNOLOGY IN THE NEGEV LTD., Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/567,807

(22) PCT Filed: Sep. 13, 2016

(86) PCT No.: PCT/IL2016/051020
§ 371 (c)(1),
(2) Date: Oct. 19, 2017

(87) PCT Pub. No.: WO2017/046794
PCT Pub. Date: Mar. 23, 2017

(65) Prior Publication Data
US 2018/0118700 A1  May 3, 2018

Related U.S. Application Data

(60) Provisional application No. 62/217,986, filed on Sep. 14, 2015.

(51) Int. Cl.
| | |
|---|---|
| *C07D 295/15* | (2006.01) |
| *C07D 207/416* | (2006.01) |
| *C07D 211/66* | (2006.01) |
| *A61P 25/28* | (2006.01) |
| *A61P 25/16* | (2006.01) |
| *A61P 9/00* | (2006.01) |
| *A61P 9/06* | (2006.01) |
| *A61K 31/445* | (2006.01) |
| *C07D 471/10* | (2006.01) |
| *A61K 31/435* | (2006.01) |
| *A61K 31/454* | (2006.01) |
| *A61K 31/4965* | (2006.01) |
| *C07D 401/04* | (2006.01) |
| *C07D 207/273* | (2006.01) |
| *C07D 207/36* | (2006.01) |

(52) U.S. Cl.
CPC .......... *C07D 295/15* (2013.01); *A61K 31/435* (2013.01); *A61K 31/445* (2013.01); *A61K 31/454* (2013.01); *A61K 31/4965* (2013.01); *A61P 9/00* (2018.01); *A61P 9/06* (2018.01); *A61P 25/16* (2018.01); *A61P 25/28* (2018.01); *C07D 207/273* (2013.01); *C07D 207/36* (2013.01); *C07D 207/416* (2013.01); *C07D 211/66* (2013.01); *C07D 401/04* (2013.01); *C07D 471/10* (2013.01)

(58) Field of Classification Search
None
See application file for complete search history.

(56) References Cited

U.S. PATENT DOCUMENTS

| | | |
|---|---|---|
| 2004/0029887 A1 | 2/2004 | Bhatia et al. |
| 2018/0078548 A1 | 3/2018 | Shoshan-Barmatz et al. |

FOREIGN PATENT DOCUMENTS

| | | | |
|---|---|---|---|
| CN | 1944424 | | 4/2007 |
| CN | 1948298 B | * | 9/2010 |
| WO | WO 03/028728 | | 4/2003 |
| WO | WO 2008/063984 | | 5/2008 |
| WO | WO 2014/192865 | | 12/2014 |
| WO | WO2015099196 | * | 7/2015 |

OTHER PUBLICATIONS

Chemical Abstract Registry No. 792941-16-3, indexed in the Registry File on STN CAS Online, Dec. 6, 2004.*
Chemical Abstract Registry No. 924861-14-3, indexed in the Registry File on STN CAS Online, Mar. 5, 2007.*
CAPLUS printout of Foreign Patent No. CN1948298B, published on Sep. 1, 2010.*
Schafer, S., Kolkhof, P. Failure is an option: learning from unsuccessful proof-of-concept trials. Drug Discovery Today. Nov. 2008, 13, 913-916.*
Honig, H., Pullman, W. From bench to clinic and back: Perspective on the 1st IQPC Translational Research conference. Journal of Translational Medicine. Dec. 2004, 2, 44.*
Ben-Hail et al., Novel Compounds Targeting the Mitochondrial Protein VDAC1 Inhibit Apoptosis and Protect against Mitochondrial Dysfunction. Journal of Biological Chemistry 2016, 291, 24986-25003.*

(Continued)

*Primary Examiner* — Po-Chih Chen
(74) *Attorney, Agent, or Firm* — Nixon & Vanderhye P.C.

(57) ABSTRACT

Provided herein piperazine and piperidine derivatives, their synthesis and use thereof in inhibiting VDAC oligomerization, apoptosis and mitochondria dysfunction. Also provided methods of treatment of diseases associated with said processes, e.g. Alzheimer's disease.

7 Claims, 17 Drawing Sheets

(56) References Cited

OTHER PUBLICATIONS

Registry No. 1385037-69-3, (STN search) Aug. 1, 2012.
Registry No. 89474-12-4, (STN search). Nov. 16, 1984.
International Search Resort issued in Appln. No. PCT/IL2016/051020 dated Jan. 10, 2017.
Written Opinion of the International Search Report issued in Appln. No. PCT/IL2016/051020 dated Jan. 10, 2017.
Bauer et al., "Functional Model of Metabolite Gating by Human Voltage-Dependent Anion Channel 2," Biochemistry, vol. 50: 3408-3410 (2011).
Baumgartner et al., "Calcium Elevation in Mitochondria Is the Main $Ca^{2+}$ Requirement for Mitochondrial Permeability Transition Pore(mPTP) Opening," Journal of Biological Chemistry, vol. 284, No. 31: 20796-20803 (Jul. 31, 2009).
Ben-Hail et al., "VDAC1-interacting anion transport inhibitors inhibit VDAC1oligomerization and apoptosis," Biochimica et Biophysica Acta, vol. 1863: 1612-1623 (2016).
Journigan et al., "Nonpeptide Small Molecule Agonist and Antagonist Original Leads for Neuropeptide FF1 and FF2 Receptors," Journal of Medicinal Chemistry, vol. 57: 8903-8927 (Sep. 30, 2014).
Keinan et al., "The role of calcium in VDAC1 oligomerization and mitochondria-mediated apoptosis," Biochimica et Biophysica Acta, vol. 1833: 1745-1754 (2013).
Obniska et al., "Synthesis, anticonvulsant activity and $5-HT_{1A}$, $5-HT_{2A}$ receptor affinity of new N-[(4-arylpiperazin-1-yl)-alkyl] derivatives of 2-azaspiro[4.4]nonane and [4.5]decane-1,3-dione," European Journal of Medicinal Chemistry, vol. 41: 874-881 (2006).
Shoshan-Barmatz et al., "VDAC, a multi-functional mitochondrial protein regulating cell life and death," Molecular Aspects of Medicine, vol. 31: 227-285 (2010).
Shoshan-Barmatz et al., "Mitochondrial VDAC1: Function in Cell Life and Death and a Target for Cancer Therapy," Current Medicinal Chemistry, vol. 19, No. 5: 714-735 (2012).
Shoshan-Barmatz et al., "VDAC, a multi-functional mitochondrial protein as a pharmacological arget," Mitochondrion, vol. 12: 24-34 (2012).
Zhang et al., "In silico design and synthesis of piperazine-1-pyrrolidine-2,5-dione scaffold-based novel malic enzyme inhibitors," Bioorganic & Medicinal Chemistry Letters, vol. 16: 525-528 (2006).
Alamed et al., "Two-day radial-arm water maze learning and memory task; robust resolution of amyloid-related emory deficits in transgenic mice" Nature Protocols, 1(4): 1671-1679 (2006).
Arzoine et al., "Voltage-dependent Anion Channel 1-based Peptides Interact with Hexokinase to Prevent Its Anti-apoptotic Activity" The Journal of Biological Chemistry, 284(6): 3946-3955 (2009).
Ben-Hail et al., "Novel Compounds Targeting the Mitochondrial Protein VDAC1 Inhibit Apoptosis and Protect against Mitochondrial Dysfunction" Journal of Biological Chemistry, 291(48): 24986-25003 (2016).
Betarbet et al., "Animal models of Parkinson's disease" BioEssays, 24(4): 308-318 (2002).
Enomoto et al., "Disruptions in spatial working memory, but not short-term memory, induced by repeated ketamine exposure" Progress in Neuro-Psychopharmacology & Biological Psychiatry, 33(4):668-775 (2009).
Falk et al., "Modeling psychiatric disorders: from genomic findings to cellular phenotypes" Molecular Psychiatry, 21(9): 1167-1179 (2016).
Fernandez-Echevarria et al., "Aβ promotes VDAC1 channel dephosphorylation in neuronal lipid rafts. Relevance to the mechanisms of neurotoxicity in Alzheimer's Disease" Neuroscience, 278: 354-366 (2014).
Gonzalez-Gronow et al., "Antibodies against the voltage-dependent anion channel (VDAC) and its protective ligand hexokinase-I in children with autism" Journal of Neuroimmunology, 227: 153-161 (2010).
Grauer et al., "WAY-163909, a $5-HT_{2C}$ agonist, enhances the preclinical potency of current antipsychotics" Psychopharmacology, 204(1):37-49 (2009).
Howland et al., "Focal loss of the glutamate transporter EAAT2 in a transgenic rat model of SOD1 mutant-mediated amyotrophic lateral sclerosis (ALS)" PNAS, 99(3): 1604-1609 (2002).
Keinan et al., "Oligomenzation of the Mitochondrial Protein Voltage-Dependent Anion Channel is Coupled to the induction of Apoptosis" Molecular and Cellular Biology, 30(24): 5698-5709 (2010).
Lin et al., "Differential long term effects of early diisopropylfluorophosphate exposure in Balb/C and C57Bl/J6 mice" Int. J. Devl Neuroscience, 30(2): 113-120 (2012).
Makadia et al., "Poly Lactic-co-Glycolic Acid (PLGA) as Biodegradable Controlled Drug Delivery Carrier" Polymers (Basel), 3(3): 1377-1397 (2011).
Nabeshima et al., "Animal Model of Schizophrenia: Dysfunction of NMDA Receptor-Signaling in Mice following Withdrawal from Repeated Administration of Phencyclidine" Ann. N.Y. Acad. Sci., 1086: 160-168 (2006).
Okatsu et al., "Mitochondrial hexokinase HKI is a novel substrate of the Parkin ubiquitin ligase" Biochemical and Biophysical Research Communications, 428(1): 197-202 (2012).
Petit-Demouliere et al., "Forced swimming test in mice: a review of antidepressant activity" Psychopharmacology, 177(3): 245-255 (2005).
Regenold et al., "Mitochondrial detachment of hexokinase 1 in mood and psychotic disorders: Implications for brain energy metabolism and neurotrophic signaling" Journal of Psychiatric Research, 46(1): 95-104 (2012).
Rezin et al., "Mitochondrial Dysfunction and Psychiatric Disorders" Neurochem Res, 34(6):1021-1029 (2009).
Rosa et al., "Role of Hexokinase and VDAC in Neurological Disorders" Current Molecular Pharmacology, 9(4): 320-331 (2016).
Rosenmann et al., "A novel transgenic mouse expressing double mutant tau driven by its natural promoter exhibits tauopathy characteristics" Experimental Neurology, 212(1): 71-84 (2008).
Saraiva et al., "Amyloid-β Triggers the Release of Neuronal Hexokinase 1 from Mitochondria" PLoS One, 5(12):e15230, 8 pgs (2010).
Shan et al., "Abnormal partitioning of hexokinase 1 suggests disruption of a glutamate transport protein complex in schizophrenia" Schizophrenia Research, 154:1-13 (2014).
Shoshan-Barmatz et al., "Key regions of VDAC1 functioning in apoptosis induction and regulation by hexokinase" Biochimica et Biophysica Acta, 1787(5):421-430 (2009).
Shoshan-Barmatz et al., "The mitochondrial voltage-dependent anion channel 1 in tumor cells" Biochimica et Biophysica Acta, 1848: 2547-2575 (2015).
Shoshan-Barmatz et al. "VDAC1, mitochondrial dysfunction, and Alzheimer's disease" Pharmacological Research, 131 (2018) 87-101.
Tremolizzo et al., "An epigenetic mouse model for molecular and behavioral neuropathologies related to schizophrenia vulnerability" PNAS, 99(26): 17095-17100 (2002).
Van Spronsen et al., "Synapse Pathology in Psychiatric and Neurologic Disease" Curr Neurol Neurosci Rep, 10(3): 207-214 (2010).
Webster et al., "Using mice to model Alzheimer's dementia: an overview of the clinical disease and the preclinical behavioral changes in 10 mouse models" Frontiers in Genetics, 5(88):1-23 (2014).
Gu, "Synthesis of phenylpiperazino compuounds as dopamine $D_3$ receptor ligands" Journal of Hainan Normal University (Natural Science), vol. 20, No. 4: 342-345 & 360 (Dec. 2007) (w/ English abstract on p. 360), (Eng. abstract only).
Guo et al., "Discovery of Aroyl Piperazine Derivatives as $I_{Kr}$ & $I_{Ks}$ Dual Inhibitors for Cardiac Arrhythmia Treatment" Medicinal Chemistry, vol. 10: 497-505 (2014).
Kempter et al., "Synthese von heteroanalogen Piperidinoacetaniliden" (English translation: "Synthesis of heteroanalogs of piperidinoacetanilides") Wissenschaftliche Zeitschrift—Martin-Luther Universität Halle-Wittenberg-Mathematisch-Naturwissenschaftliche Reihe, vol. 32, No. 5: 3-25 (1983) (w/ English summary on p. 23), (Eng. summary only).
Search Report issued in EP Appln. No. 16845836.2 dated Feb. 12, 2019.

(56) References Cited

OTHER PUBLICATIONS

Office Action dated Nov. 26, 2018 in a U.S. Appl. No. 15/700,801 (8 pages).

* cited by examiner

Fig. 18a
Fig. 18b
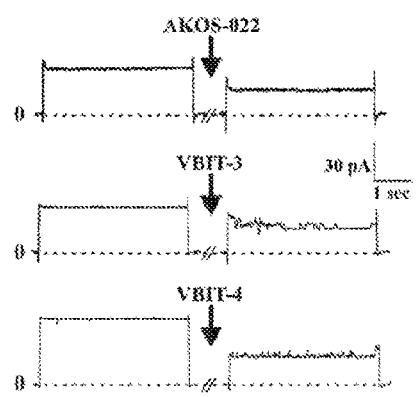
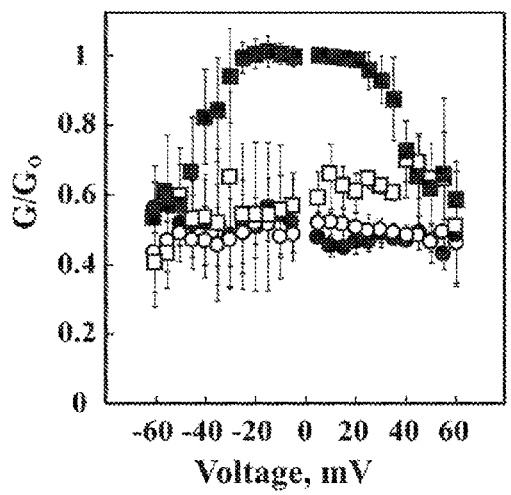
Fig. 18c
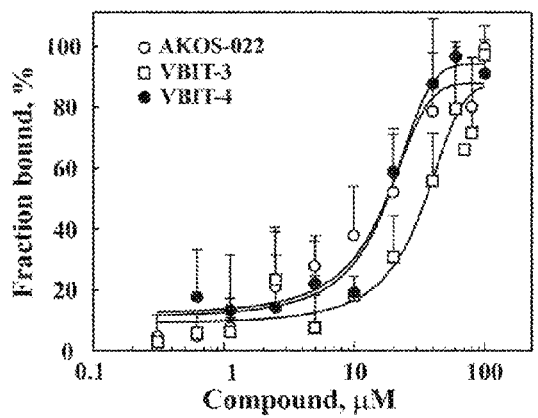

PIPERAZINE AND PIPERIDINE DERIVATIVES, THEIR SYNTHESIS AND USE THEREOF IN INHIBITING VDAC OLIGOMERIZATION, APOPTOSIS AND MITOCHONDRIA DYSFUNCTION

This application is the U.S. national phase of International Application No. PCT/IL2016/051020 filed Sep. 13, 2016, which designated the U.S. and claims priority to 62/217,986 filed Sep. 14, 2015.

The invention relates to use of small organic compounds interacting with the Voltage-Dependent Anion Channel (VDAC), reducing its channel conductance and acting as inhibitors of VDAC oligomerization, associated with apoptosis induction, for the treatment of diseases associated with enhanced apoptosis. In particular the present invention relates to the compounds of the general formulae (I) and (II) for the treatment of enhanced apoptosis-associated diseases, such as neurodegenerative and cardiovascular diseases. The present invention also embraces pharmaceutical compositions comprising these compounds and methods of using the compounds and their pharmaceutical compositions.

VDAC forms the main interface between mitochondrial and cellular metabolisms by mediating the fluxes of ions, nucleotides and other metabolites across the outer mitochondrial membrane (OMM) (Shoshan-Barmatz, V., et. al (2010) VDAC, a multi-functional mitochondrial protein regulating both cell life and death. Molecular Aspects of Medicine 31(3), 227-286; Shoshan-Barmatz, V. and Ben-Hail, D. (2012) VDAC, a multi-functional mitochondrial protein as a pharmacological target, Mitochondrion, 12(1):24-34). VDAC has also been recognized as a key protein in mitochondria-mediated apoptosis. VDAC mediates the release of apoptosis-inducing proteins from mitochondria to the cytosol and regulates apoptosis via interaction with pro- and anti-apoptotic proteins (Shoshan-Barmatz, V., et. al (2010) VDAC, a multi-functional mitochondrial protein regulating both cell life and death. Molecular Aspects of Medicine 31(3), 227-286; Shoshan-Barmatz V. and Golan M. (2012) Mitochondrial VDAC: Function in cell life and death and a target for cancer therapy, Current Medicinal Chemistry 19(5), 714-735).

Piperazine and piperidine are used as essential sub-structure motifs in various drugs. Piperazine pyrrolidine-2,5-dione derivatives have also been demonstrated as malic enzyme inhibitors (Zhang, Y. John et al. 2006. Biorganic & Medicinal Chemistry Letters 16, 525-528).

It has now been found by the present inventors that members of a novel group of piperazine- and piperidine-based compounds directly interact with and have high inhibitory activity of VDAC oligomerization and are thus useful as inhibitors of its channel conductance, it oligomerization and thereby as inhibitors of the release of apoptogenic proteins from the mitochondria, as well as inhibitors of apoptotic cell death or other cell death types as necrosis.

The present invention provides substituted piperazine- and piperidine-derivatives of general Formula (I)

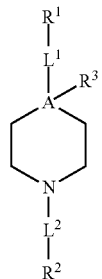

Formula (I)

wherein the groups $R^1$, $R^2$, $R^3$, $L^1$, $L^2$ and A are as defined hereinafter, including the stereoisomers, enantiomers, mixtures thereof and salts thereof.

Compounds of general Formulae (I) and (II), as defined hereinafter, are suitable for inhibiting the oligomerization of mitochondrial Voltage-Dependent Anion Channel (VDAC) protein, an early and critical step in the progression of apoptosis. Compounds of general Formulae (I) and (II) are also suitable for protecting a cell against apoptosis. Compounds of general Formulae (I) and (II) are further suitable for protecting a cell against mitochondrial dysfunction associated with apoptosis induction and/or compromised cell energy production, reactive oxygen radicals (ROS) production and/or alterations in intracellular calcium concentration.

The invention also relates to processes for preparing a compound of general Formula (I) according to the invention.

The invention is further directed to pharmaceutical compositions containing a compound of Formulae (I) or (II) according to the invention, as well as to the use of the compounds of Formulae (I) and (II) for preparing a pharmaceutical composition for the treatment of diseases and disorders, especially diseases and disorders associated with enhanced apoptosis or other cell death types as necrosis.

Other aspects and embodiments of the present invention will become apparent to the skilled person from the following detailed description.

BRIEF DESCRIPTION OF THE FIGURES

FIG. 18a demonstrates current through purified VDAC1 channel in presence of compounds of Formulae 1, 2, and 10.

FIG. 18b demonstrates the fraction of maximal conductance of purified VDAC1 in presence of the compounds of the Formulae 1 (solid circle), 2 (empty square) or 10 (empty circle), at varying applied voltage.

FIG. 18c demonstrates the bound fraction of the compounds of the Formulae 1, 2 and 10 to the purified VDAC1, as a function of their concentration.

Figure 1:
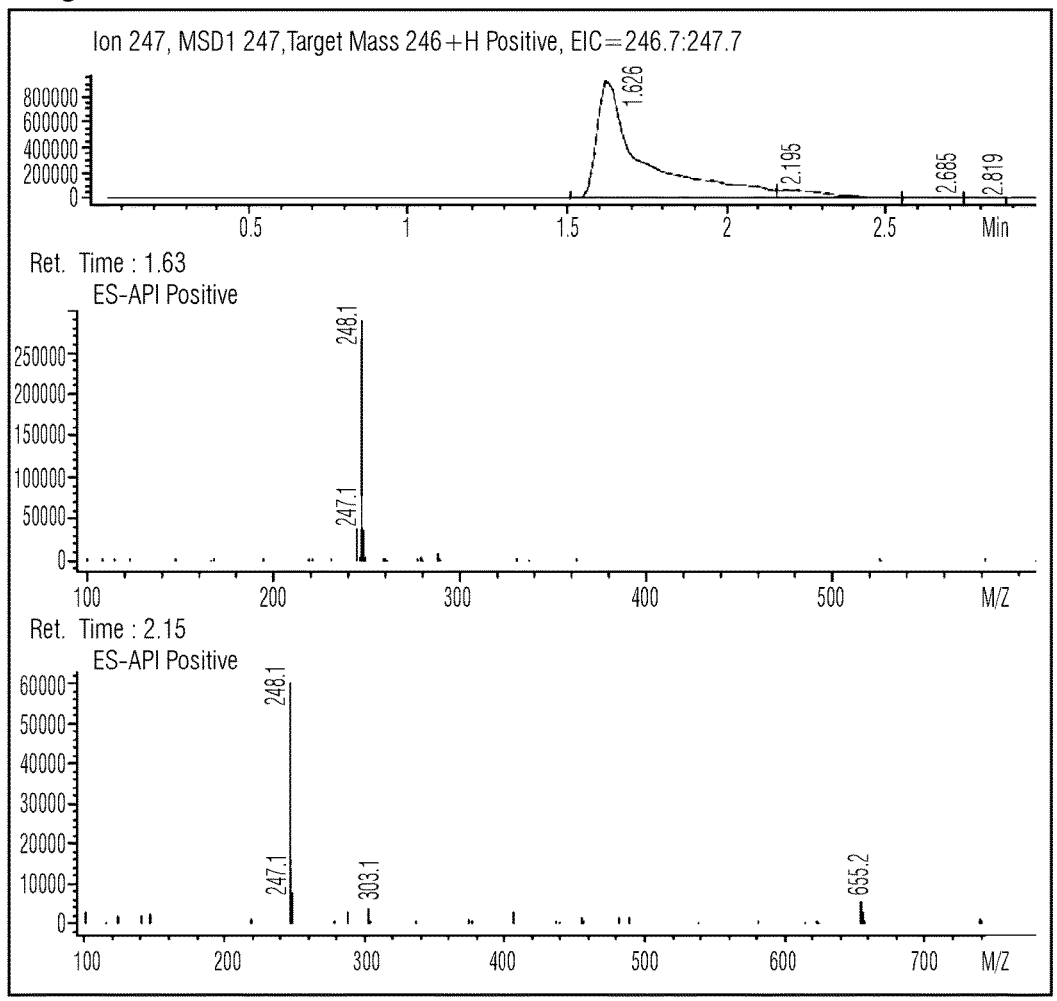
FIG. 1 demonstrates a representative chromatogram and respective mass spectra of two peaks of interest relating to Intermediate 1.

According to one aspect of the invention there is provided a compound of the general formula (I):

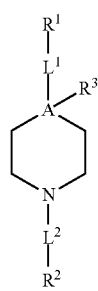

Formula (I)

wherein:

A is carbon (C) or nitrogen (N);

$R^3$ is hydrogen or heteroalkyl group; wherein when A is nitrogen (N), $R^3$ is absent;

$L^1$ is a linking group which may be absent or present, but if present is an amino linking group —$NR^4$—, wherein $R^4$ is hydrogen, a $C_{1-n}$-alkyl, wherein n is an integer from 2 to 5, inclusive, or a substituted alkyl $CH_2$—R, wherein R is a functional group selected from hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl; preferably $R^4$ is hydrogen;

$R^1$ is an aromatic moiety, preferably phenyl, which may be substituted with one or more of Z;

Z is independently one or more of functional groups selected from, hydrogen, halo, haloalkyl, haloalkoxy, perhaloalkoxy or $C_{1-2}$-perfluoroalkoxy, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl; preferably Z is $C_{1-2}$-perfluoroalkoxy; preferably $R^1$ is a phenyl and Z is trifluoromethoxy; preferably $R^1$ is a phenyl substituted with one trifluoromethoxy, most preferably at the para position;

$L^2$ is a linking group, such that when A is nitrogen (N), $L^2$ is a group consisting of 4-10 atoms (apart from hydrogen atoms), optionally forming a closed ring, whereof at least one of the atoms is nitrogen, said nitrogen forming part of an amide group; preferably said linking group is selected from the group consisting of an $C_{4-6}$-alkylamidylene and a pyrrolidinylene, said linking group optionally substituted with one or two of alkyl, hydroxy, oxo or thioxo group; most preferably $L^2$ is selected from butanamidylene, N-methylbutanamidylene, N,N-dimethylbutanamidylene, 4-hydroxybutanamidylene (HO—$CH_2$—C*H—$CH_2$—C(O)NH—, wherein the asterisk denotes attachment point), 4-oxobutanamidylene, 4-hydroxy-N-methylbutanamidylene, 4-oxo-N-methylbutanamidylene, 2-pyrrolidonyle, pyrrolidine-2,5-dionylene, 5-thioxo-2-pyrrolidinonylene and 5-methoxy-2-pyrrolidinonylene;

and when A is carbon (C), then $L^2$ is $C_{1-n}$ alkylene, wherein n is an integer from 2 to 4, inclusive; $L^2$ is preferably methylene (—$CH_2$—);

$R^2$ is a phenyl or a naphthyl, optionally substituted with halogen, preferably when $R^2$ is a phenyl it is substituted with halogen, preferably chlorine, at the para position, preferably when $R^2$ is naphthyl, $L^2$ is an alkylene group, preferably —$CH_2$—;

with a proviso that when A is carbon (C), $L^1$ is —$NR^4$—, $R^4$ is hydrogen, and $R^2$ is phenyl substituted with chlorine, then $L^2$ is not pyrrolidine-2,5-dione.

In one embodiment, when A is nitrogen (N), the linking group $L^2$ is selected from the group consisting of an $C_{4-6}$-alkylamidylene and a pyrrolidinylene, said linking group optionally substituted with one or two of alkyl, hydroxy, oxo or thioxo group. For example, $L^2$ may be butanamidylene, N-methylbutanamidylene, N,N-dimethylbutanamidylene, 4-hydroxybutanamidylene, 4-oxobut-anamidylene, 4-hydroxy-N-methylbutanamidylene, 4-oxo-N-methyl-butanamidylene, 2-pyrrolidonyle, pyrrolidine-2,5-dionylene, 5-thioxo-2-pyrrolidinonylene or 5-methoxy-2-pyrrolidinonylene. Preferably, when $L^2$ is butanamidylene, N-methylbutanamidylene, N,N-dimethylbutanamidylene, 4-hydroxybutanamidylene, 4-oxobut-anamidylene, 4-hydroxy-N-methylbutanamidylene or 4-oxo-N-methylbutanamidylene, then preferably the carbon in third position (C) of the butanamide moiety is bonded to the nitrogen (N) of the piperazine ring or the piperidine ring and the nitrogen (N) of the butanamide moiety is bonded to $R^2$. For example, when $L^2$ is 2-pyrrolidone, pyrrolidine-2,5-dione, 5-thioxo-2-pyrrolidone or 5-methoxy-2-pyrrolidone, then preferably a carbon (C) of the pyrrolidine moiety is bonded to the nitrogen (N) of the piperazine ring or the piperidine ring and the nitrogen (N) of the pyrrolidine moiety is bonded to $R^2$.

In another embodiment, A is carbon (C), $R^3$ is heteroalkyl and $L^2$ is methylene.

The invention also relates to the stereoisomers, enantiomers, mixtures thereof, and salts, particularly the physiologically acceptable salts, of the compounds of general Formula (I) according to the invention.

According to another aspect of the invention there is provided a compound of the general formula (Ia):

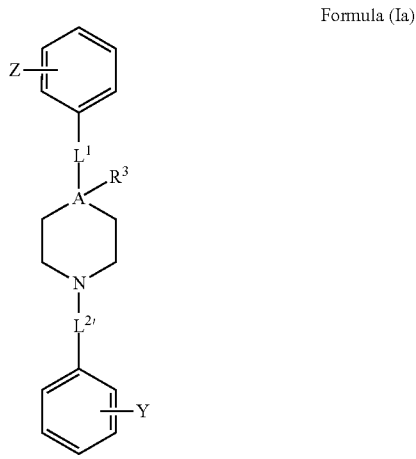

Formula (Ia)

wherein:

A, R³, Z and L¹ are as previously defined in reference to compound of Formula (I); preferably A is nitrogen (N);

L²' is a linking group selected from the group consisting of an $C_4$-alkylamidylene, $C_5$-alkylamidylene or $C_6$-alkylamidylene, optionally substituted with one or two of alkyl, hydroxy, oxo or thioxo group; preferably L²' is selected from butanamidylene, N-methylbutanamidylene, N,N-dimethylbutanamidylene, 4-hydroxybut-anamidylene, 4-oxobutanamidylene, 4-hydroxy-N-methylbutan-amidylene or 4-oxo-N-methylbutanamidylene; most preferably L²' is 4-hydroxybutanamidylene; wherein preferably the carbon (C) at position 3 of the alkyl moiety of alkylamidylene L²' is bonded to the nitrogen (N) of the piperazine ring or of the piperidine ring, and the nitrogen (N) of the butanamide moiety is bonded to the phenyl group; preferably L²' is HO—CH₂—C*H—CH₂—C(O)NH—, wherein the asterisk denotes attachment point;

Y is halogen, preferably chlorine, e.g. at the para position;

or an enantiomer, diastereomer, mixture or salt thereof.

According to another aspect of the invention there is provided a compound of the general formula (Ib):

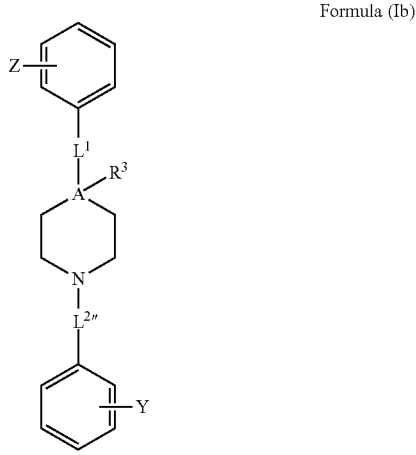

Formula (Ib)

wherein:

A, R³, and Z are as previously defined in reference to the compound of Formula (I); preferably A is nitrogen (N);

L¹ is absent;

L²'' is a pyrrolidinylene linking group, optionally substituted with one or two of alkyl, hydroxy, oxo or thioxo group, preferably L²'' is selected from 2-pyrrolidonylene, pyrrolidine-2,5-dionylene, 5-thioxo-2-pyrrolidinonylene and 5-methoxy-2-pyrrolidinonylene; most preferably L²'' is pyrrolidine-2,5-dionylene; wherein preferably a carbon (C) at position 4 or the carbon (C) at position 3 of the pyrrolidinyl moiety L²'' is bonded to the nitrogen (N) of the piperazine ring or the piperidine ring and the nitrogen (N) of the pyrrolidinyl moiety is bonded to the phenyl group substituted with Y;

Y is halogen, preferably chlorine, e.g. at the para position;

provided that when A is carbon (C), L¹ is present and R⁴ is hydrogen, L²'' is not pyrrolidine-2,5-dione.

According to yet another aspect of the invention there is provided a compound of the general formula (Ic):

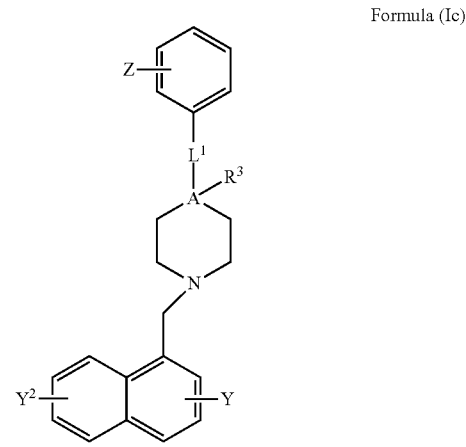

Formula (Ic)

wherein:

A, R³, and Z are as previously defined in reference to the compounds of general Formula (I);

L¹ is —NH—;

Y¹ and Y² may be absent or present, but if present are independently a halogen;

or an enantiomer, diastereomer, mixture or salt thereof.

Preferred compounds of Formula (Ic) are those wherein R³ is —C(O)NHCH₂C(O)OH group, and/or wherein Z is $C_{1-2}$-alkoxy or halogenated $C_{1-2}$-alkoxy, e.g. $C_{1-2}$-perfluoroalkoxy.

According to another aspect of the invention there is provided a compound of the general formula (Id):

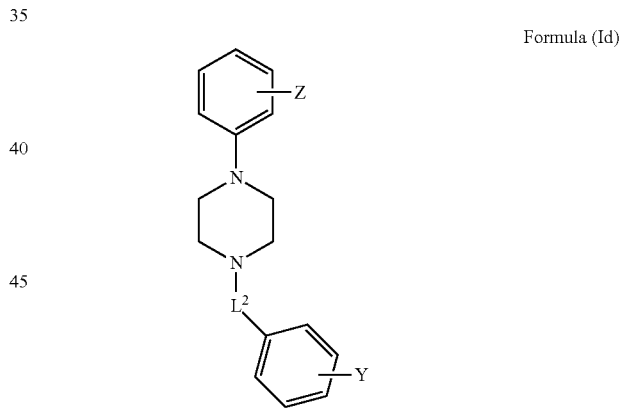

Formula (Id)

wherein

L² is selected from the group consisting of an $C_{4-6}$-alkylamidylene (e.g. HO—CH₂—C*H—CH₂—C(O)NH—, wherein the asterisk denotes attachment point), and a pyrrolidinylene (e.g. pyrrolidin-2,5-dionylene), optionally substituted with one or two of alkyl, hydroxy, oxo or thioxo group;

Z is haloalkoxy, e.g. $C_{1-2}$-perfluoroalkoxy, and Y is halogen.

The invention also relates to the stereoisomers, enantiomers, mixtures thereof and salts thereof, of the compounds of general Formulae (Ia), (Ib), (Ic), and (Id), according to the invention.

Table 1 provides non-limiting examples of compound of general Formula (I). It includes compounds as follows: N-(4-chlorophenyl)-4-hydroxy-3-(4-(4-(trifluoromethoxy)

phenyl)-piperazin-1-yl)butanamide (Formula 1), 1-(4-chlorophenyl)-3-(4-(4-(trifluoromethoxy)phenyl)piperazin-1-yl)pyrrolidine-2,5-dione (Formula 2), 1-(naphthalen-1-yl)methyl)-4-(phenylamino)-piperidine-4-carbonyl)glycine (Formula 3), 1-(4-chlorophenyl)-3-(4-(4-(trifluoromethoxy)phenyl)pyrrolidin-1-yl)pyrrolidin-2-one (Formula 4), 1-(4-chlorophenyl)-5-thioxo-3-(4-(4-(trifluoro-methoxy)phenyl)piperazin-1-yl)pyrrolidin-2-one (Formula 5), 1-(4-chlorophenyl)-5-methoxy-4-(4-(4-(trifluoromethoxy)phenyl)-piperazin-1-yl)pyrrolidin-2-one (Formula 6), 1-(4-chlorophenyl)-5-thioxo-4-(4-((4-(trifluoromethoxy)phenyl)amino)piperidin-1-yl)pyrrolidin-2-one (Formula 7), 4-(4-chlorophenyl)-4-oxo-3-(4-(4-(trifluoromethoxy)phenyl)piperazin-1-yl)butanamide (Formula 8), N-(4-chlorophenyl)-4-hydroxy-N-methyl-3-(4-(4-(trifluoromethoxy)phenyl)piperazin-4-yl)butanamide (Formula 9).

TABLE 1

| Formula # | Structure | Description (according to general Formula (I)) |
|---|---|---|
| 1 | 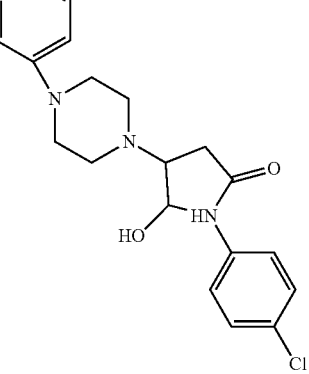 | A is nitrogen (N), $R^3$ is absent, $L^1$ is absent, $R^1$ is phenyl substituted with one trifluoromethoxy, $L^2$ is 4-hydroxybutanamidylene, the $3^{rd}$ carbon (C) of the butanamide moiety is bonded to the nitrogen (N) of the piperazine ring, the nitrogen (N) of the butanamide moiety is bonded to $R^2$ and $R^2$ is a phenyl substituted with chlorine at the para position [also identified herein as VBIT-4 or as BGD-4] |
| 2 | 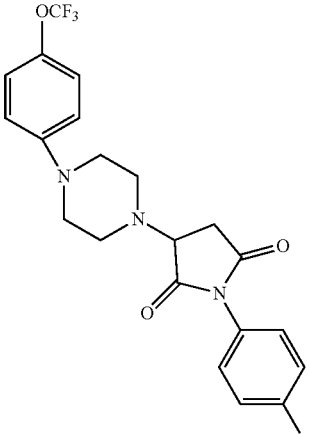 | A is nitrogen (N), $R^3$ is absent, $L^1$ is absent, $R^1$ is phenyl substituted with one trifluoromethoxy, $L^2$ is pyrrolidine-2,5-dione, the carbon (C) at position 3 of the pyrrolidine moiety is bonded to the nitrogen (N) of the piperazine ring, the nitrogen (N) of the pyrrolidine moiety is bonded to $R^2$ and $R^2$ is a phenyl substituted with chlorine at the para position [also identified herein as VBIT-3 or as BGD-3] |
| 3 | 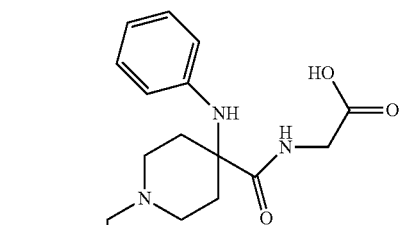 | A is carbon (C), $R^3$ is —C(O)NHCH$_2$C(O)OH group; $L^1$ is —NH—, $R^1$ is a phenyl, $L^2$ is methylene and $R^2$ is a naphthyl [also identified herein as VBIT-12] |

TABLE 1-continued

| Formula # | Structure | Description (according to general Formula (I)) |
|---|---|---|
| 4 | 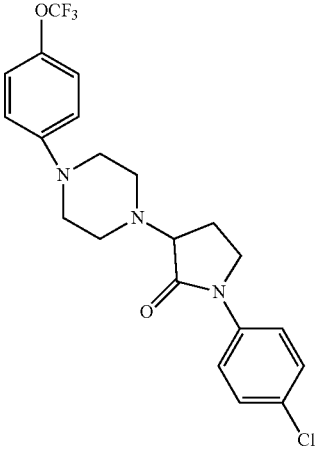 [SMILES: O=C1C(N2CCN(c3ccc(OC(F)(F)F)cc3)CC2)CCN1c1ccc(Cl)cc1] | A is nitrogen (N), $R^3$ is absent, $L^1$ is absent, $R^1$ is a phenyl substituted with one trifluoromethoxy; $L^2$ is 2-pyrrolidone, the carbon (C) at position 3 of the pyrrolidone moiety is bonded to the nitrogen (N) of the piperazine ring, the nitrogen (N) of the pyrrolidone moiety is bonded to $R^2$ and $R^2$ is a phenyl substituted with chlorine at the para position [also identified herein as VBIT-5] |
| 5 | 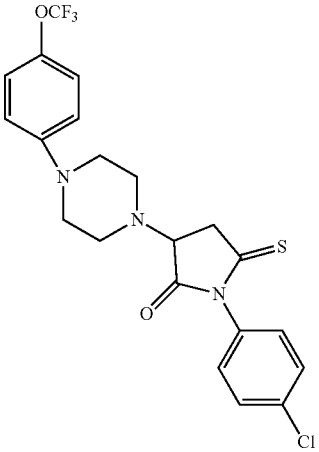 [SMILES: O=C1C(N2CCN(c3ccc(OC(F)(F)F)cc3)CC2)CC(=S)N1c1ccc(Cl)cc1] | A is nitrogen (N), $R^3$ is absent, $L^1$ is absent, $R^1$ is a phenyl substituted with one trifluoromethoxy, $L^2$ is 5-thioxo-2-pyrrolidone, the carbon (C) at position 3 of the pyrrolidine moiety is bonded to the nitrogen (N) of the piperazine ring, the nitrogen (N) of the pyrrolidine moiety is bonded to $R^2$ and $R^2$ is a phenyl substituted with chlorine at the para position [also identified herein as VBIT-6] |
| 6 | 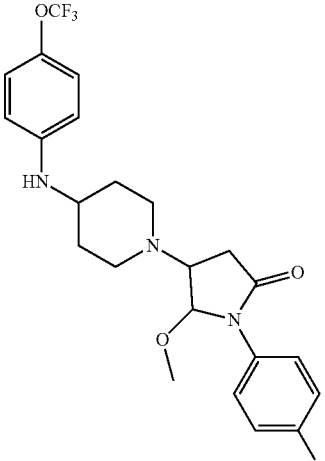 | A is carbon (C), $R^3$ is hydrogen, $L^1$ is —NH—, $R^1$ is a phenyl substituted with one trifluoromethoxy, $L^2$ is 5-methoxy-2-pyrrolidinone, the carbon (C) at position 4 of the pyrrolidine moiety is bonded to the nitrogen (N) of the piperidine ring, the nitrogen (N) of the pyrrolidine moiety is bonded to $R^2$ and $R^2$ is a phenyl substituted with chlorine at the para position [also identified herein as VBIT-9] |

TABLE 1-continued

| Formula # | Structure | Description (according to general Formula (I)) |
|---|---|---|
| 7 | 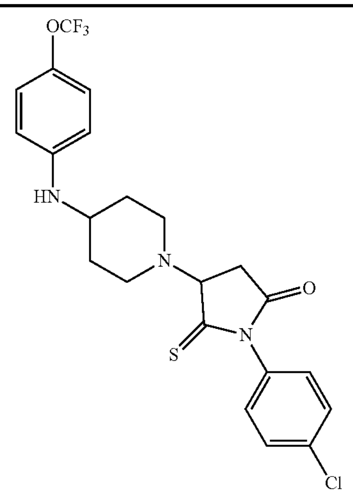 | A is carbon (C), $R^3$ is hydrogen, $L^1$ is —NH—, $R^1$ is a phenyl substituted with one trifluoromethoxy, $L^2$ is 5-thioxo-2-pyrrolidone, the carbon (C) at position 3 of the pyrrolidine moiety is bonded to the nitrogen (N) of the piperidine ring, the nitrogen (N) of the pyrrolidine moiety is bonded to $R^2$ and $R^2$ is a phenyl substituted with chlorine at the para position [also identified herein as VBIT-10] |
| 8 | 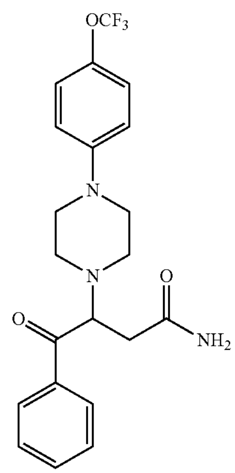 [SMILES: NC(=O)CC(C(=O)c1ccccc1)N1CCN(c2ccc(OC(F)(F)F)cc2)CC1] | A is nitrogen (N), $R^3$ is absent, $L^1$ is absent, $R^1$ is phenyl substituted with one trifluoromethoxy, $L^2$ is 4-oxobutanamide, the $3^{rd}$ carbon (C) of the butanamide moiety is bonded to the nitrogen (N) of the piperazine ring, the $4^{th}$ carbon (C) of the butanamide moiety is bonded to $R^2$ and $R^2$ is a phenyl substituted with chlorine at the para position [also identified herein as VBIT-7] |
| 9 | 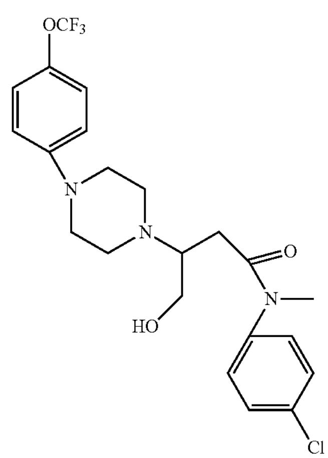 [SMILES: CN(C(=O)CC(CO)N1CCN(c2ccc(OC(F)(F)F)cc2)CC1)c1ccc(Cl)cc1] | A is nitrogen (N), $R^3$ is absent, $L^1$ is absent, $R^1$ is phenyl substituted with one trifluoromethoxy, $L^2$ is 4-hydroxy-N-methylbutanamide, the $3^{rd}$ carbon (C) of the butanamide moiety is bonded to the nitrogen (N) of the piperazine ring, the nitrogen (N) of the butanamide moiety is bonded to $R^2$ and $R^2$ is a phenyl substituted with chlorine at the para position [also identified herein as VBIT-8] |

Some terms used herein to describe the compounds according to the invention are defined more specifically below.

The term halogen denotes an atom selected from among F, Cl, Br and I, preferably Cl and Br.

The term heteroalkyl as used herein in reference to $R^3$ moiety of the general Formulae (I), (Ia), (Ib), (Ic), (Id), (II) and (IIa), refers to a saturated or unsaturated group of 3-12 atoms (apart from hydrogen atoms), wherein one or more (preferably 1, 2 or 3) atoms are a nitrogen, oxygen, or sulfur atom, for example an alkyloxy group, as for example methoxy or ethoxy, or a methoxymethyl-, nitrile-, methyl-carboxyalkylester- or 2,3-dioxyethyl-group; preferably heteroalkyl group is a chain comprising an alkylene, and at least one of a carboxylic acid moiety, a carbonyl moiety, an amine moiety, a hydroxyl moiety, an ester moiety, an amide moiety. The term heteroalkyl refers furthermore to a carboxylic acid or a group derived from a carboxylic acid as for example acyl, acyloxy, carboxyalkyl, carboxyalkylester, such as for example methylcarboxyalkylester, carboxyalkylamide, alkoxycarbonyl or alkoxycarbonyloxy; preferably the term refers to —C(O)NHCH$_2$C(O)OH group.

The term C$_{1\text{-}n}$-alkyl, wherein n may have a value as defined herein, denotes a saturated, branched or unbranched hydrocarbon group with 1 to n carbon (C) atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term C$_{1\text{-}n}$-alkoxy, wherein n may have a value as defined herein, denotes an alkyl group as defined herein, bonded via —O— (oxygen) linker.

The term C$_{1\text{-}n}$-perfluoroalkoxy, wherein n may have a value as defined herein, denotes an alkoxy group with hydrogen atoms substituted by fluorine atoms.

The term C$_{1\text{-}m}$-alkylamidyl, wherein m may have a value as defined herein, denotes a group comprising 1 to m carbon (C) atoms and an amide group formed by either C$_{m\text{-}a}$alkyl-COOH and H$_2$N—C$_a$alkyl, or C$_{m\text{-}a}$alkyl-NH$_2$ and HOOC-C$_a$alkyl, wherein a is smaller than or equal to m. Similarly, the terms C$_4$-alkylamidylene, C$_5$-alkylamidylene and C$_6$-alkylamidylene refer to divalent C$_m$-alkylamidyl groups, wherein m is either 4, 5, or 6, respectively.

The term "VDAC" as used herein, unless the context explicitly dictates otherwise, refers to Voltage-Dependent Anion Channel protein, to all its isoforms, e.g. to isoform VDAC1, to isoform VDAC2, or to isoform VDAC3.

According to another aspect of the invention, provided herein is a process for the preparation of a compound of Formula (I). The compounds of Formula (I) according to the invention may be obtained using known methods of synthesis. Preferably the compounds are obtained by methods of preparation that are described more fully hereinafter.

Certain compounds of the general Formula (I), wherein L$^1$ is absent, and A is nitrogen, may be prepared by coupling an aryl halide of the formula R$^1$—X, wherein X is a halogen, preferably bromide, with a mono-protected piperazine, e.g. with BOC-protected piperazine, and upon deprotection, reacting with a L$^2$-linker precursor reactive with secondary amines, and subsequent amidation or transamidation of the L$^2$-linker precursor moiety with a suitable amine of the formula (Y)R$^2$—NH$_2$. The L$^2$-linker precursor may be an unsaturated C$_{4\text{-}6}$ carboxylic derivative compound, e.g. an unsaturated C$_{4\text{-}6}$ lactone, or a β-, γ-, δ- or ε-unsaturated linear ester of the C$_{4\text{-}6}$ carboxylic acid and a suitable alcohol, e.g. C$_{1\text{-}6}$ alcohol. Alternatively, the deprotected R$^1$-piperazine may be reacted with a suitable N—R$^2$-pyrrolidenone or N—R$^2$-pyrrolidinene-dione, prepared by generally known methodology (e.g. in Synthesis, anticonvulsant activity and 5-HT1A, 5-HT2A receptor affinity of new N-[(4-arylpiperazin-1-yl)-alkyl] derivatives of 2-azaspiro[4.4]nonane and [4.5]decane-1,3-dione, by Obniska, J.; Kolaczkowski, M.; Bojarski, A. J.; Duszynska, B., European Journal of Medicinal Chemistry (2006), 41(7), 874-881).

Compounds of general Formulae (Ia) and (Ib) may be prepared according to a Method (a) shown in Schemes 1 to 3, starting from a compound of general Formula A, wherein Z is as hereinbefore defined.

Scheme 1

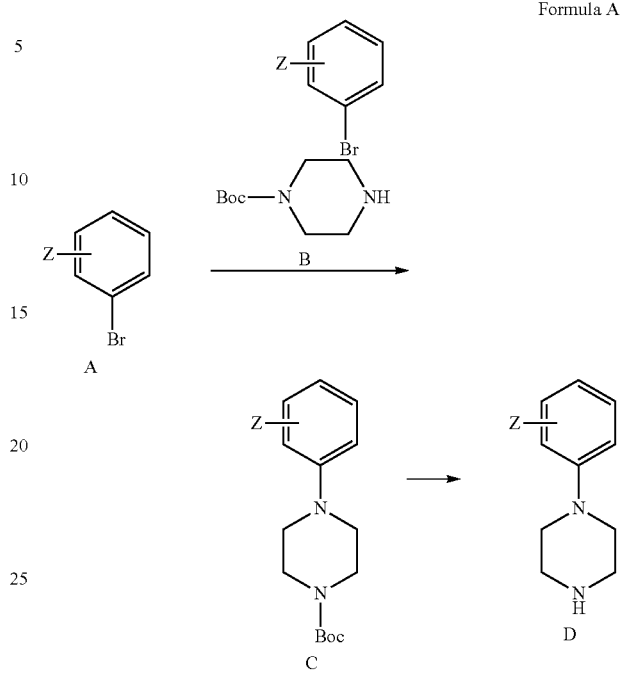

Compounds of general Formula C are obtained by reacting a compound of general Formula A with a piperizine in which one of the nitrogens is protected with a protecting group, e.g. tert-butyloxycarbonyl protecting group (BOC group). The starting compounds of general Formula A is either commercially obtainable or may be prepared by using known methods from commercially obtainable compounds. The carbon-nitrogen (C—N) coupling reaction is carried out in the presence of a palladium catalyst, such as tris(dibenzylideneacetone)dipalladium (Pd$_2$(dba)$_3$) that is particularly suitable. The reaction is carried out in a presence of a bidentate phosphine ligand and a base. Suitable bidentate phosphine ligands are diphenyl-phosphinobinapthyl (BINAP) and diphenylphosphinoferro-cene (DPPF), while BINAP is particularly preferred. Suitable bases include sodium tert-butoxide, potassium tert-butoxide, lithium bis(trimethylsilyl)-amide, while sodium tert-butoxide is particularly suitable. The reaction is carried out in a suitable aprotic solvent such as toluene, tetrahydrofuran (THF), dioxane, but preferably toluene, under nitrogen atmosphere, and at a temperature between 55° C. and 110° C., preferably at a temperature of 65° C. and 110° C., most preferably 80° C. and 110° C. Upon completion of the reaction the solvent is evaporated to provide crude compound of Formula C as a residue that may be used for the next step without further purification.

Compounds of general Formula D are obtained by removal of the protecting group, e.g. BOC, in the compound of general Formula C, which can be accomplished with strong acids such as trifluoroacetic acid, neat or in dichloromethane, or with concentrated HCl in methanol or in dichloromethane (DCM), while concentrated HCl in DCM is preferred. The reaction is preferably carried out at room temperature. Upon completion of the reaction the organic phase is discarded and the aqueous phase evaporated to dryness. The residue is dissolved in a base and a suitable solvent, such as DCM, dichloroethane or 2-methyltetrahydrofuran (MeTHF), NaOH (2.0 M) and DCM are preferred. Upon completion of the reaction, the organic solvent phase, e.g. DCM, is collected and concentrated to yield the crude product of general Formula D that may be used for the next step without further purification.

Compounds of general Formula (Ia) and (Ib) are obtained from compounds of general Formula D. For example, certain preferred compounds of general Formula (Ia) may be obtained according to Scheme 2, by reacting a compound of general Formula D with a suitable lactone, e.g. 2-furanone, to yield a compound of general Formula E, which is reacted with a suitable aminophenyl to yield a compound of general Formula (Ia).

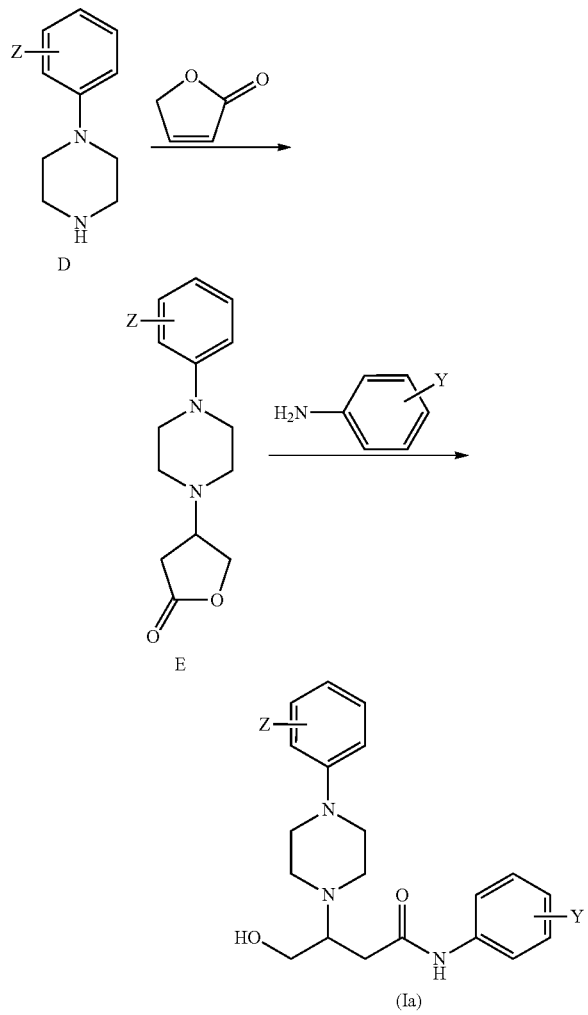

For example, certain preferred compounds of general Formula (Ib) may be obtained according to Scheme 3, by reacting a compound of general Formula D with a suitable pyrrole-dione, e.g 1-Phenyl-1H-pyrrole-2,5-dione, which is commercially available or may readily be prepared by methods familiar to those skilled in the art, to yield a compound of general Formula (Ib).

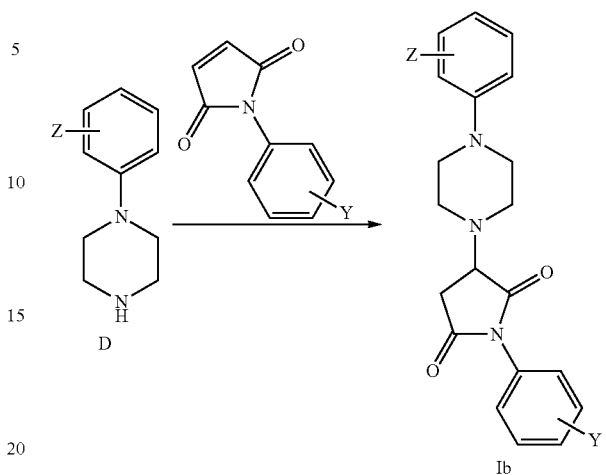

Certain compounds of the general Formula (I) wherein $R^3$ is present and is not hydrogen and wherein $L^1$ is present, can be prepared from halogenated compounds of the general formula $(Y^1)(Y^2)R^2$-$L^2$X that are coupled with a protected piperidone in presence of a base, and the recovered ketone is $R^3$-sililated, e.g. nitrilosililated, in presence of an amine of the general formula $R^1$-$L^1$-H ($L^1$-H being the —$NR^4$— group, with $R^4$ as defined hereinabove) in acid environment to furnish the compound of general formula $(Y^1)(Y^2)R^2$-$L^2$-N[—$CH_2$—$CH_2$—]$_2$C($R^3$)$L^1$-$R^1$, wherein $R^3$ is the nitrile. Thereafter, the nitrile may be hydrolyzed in a strong acid to a respective amide and further in a strong base to a respective carboxylic acid, which is reacted by peptidic methodology to a protected glycinate ester, finally deprotected to furnish the compound of formula (I).

Certain preferred compounds of general Formula (Ic) may be prepared according to a Method (b) shown in Schemes 4 and 4a, starting from a naphthyl compound of general Formula F, wherein X is halogen, preferably chlorine, p is an integer having a value of 1, 2 or 3 and $Y^1$ and $Y^2$ are as hereinbefore defined.

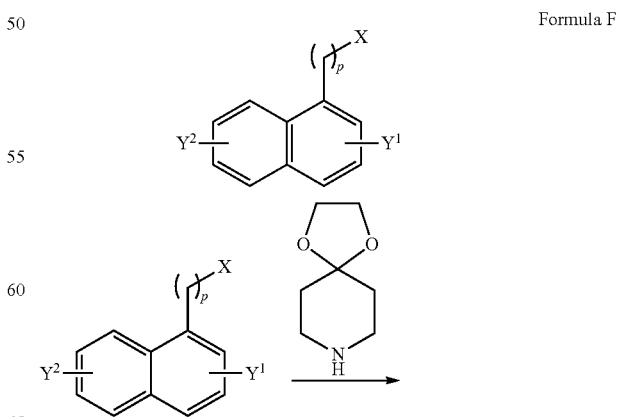

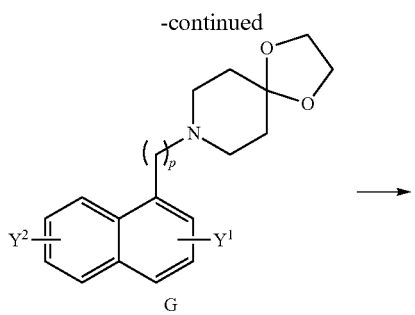

G

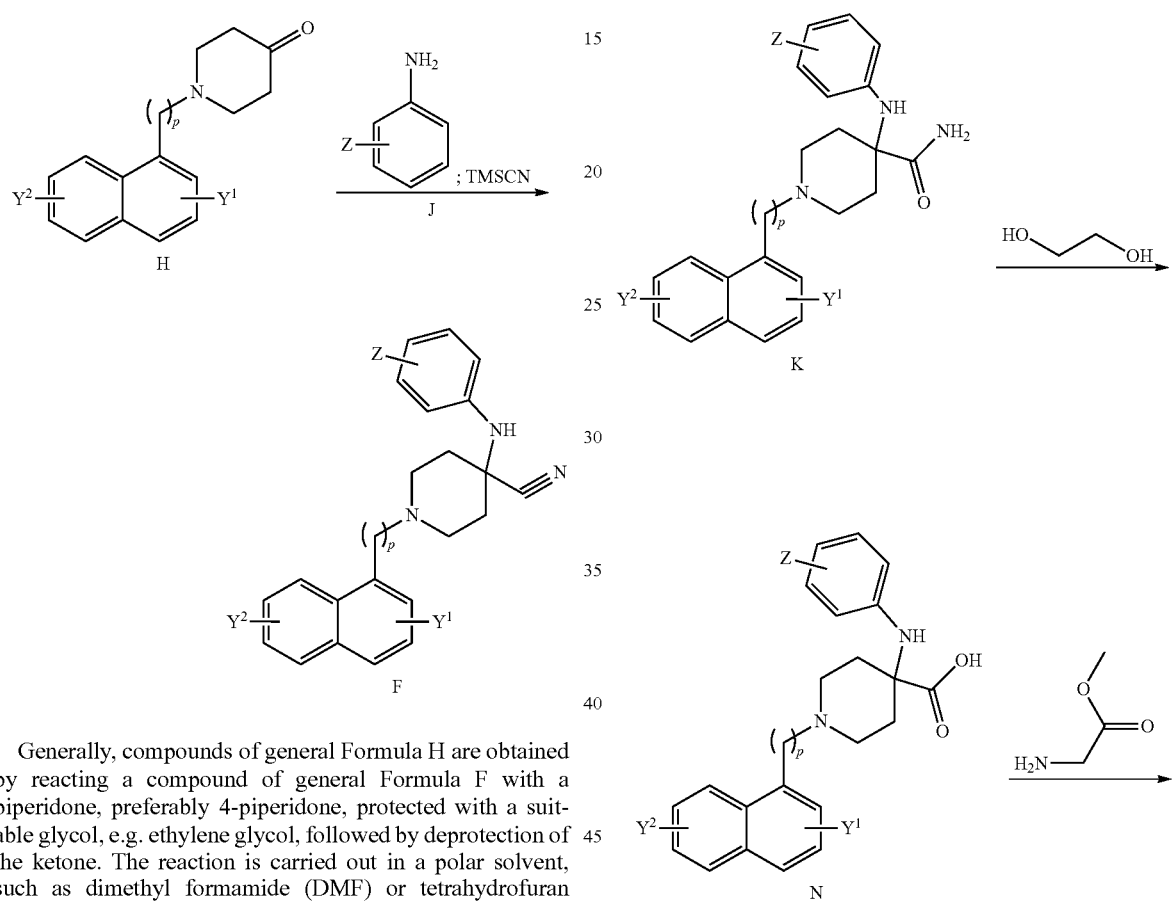

Generally, compounds of general Formula H are obtained by reacting a compound of general Formula F with a piperidone, preferably 4-piperidone, protected with a suitable glycol, e.g. ethylene glycol, followed by deprotection of the ketone. The reaction is carried out in a polar solvent, such as dimethyl formamide (DMF) or tetrahydrofuran (THF), in presence of a base. Suitable base may be a carbonate, e.g. potassium carbonate, sodium carbonate. The reaction may be carried out at a temperature between 0° C. and 60° C., preferably between 15° C. and 40° C., most preferably at ambience, e.g. at room temperature. The reaction may be kept for about 6-18 hours, preferably for about 10-14 hours. The product may be purified, e.g. by chromatography, and deprotected by heating the product under acidic conditions. The deprotection may be carried out in a suitable solvent, e.g. an alcohol, such as ethanol, that dissolves the acid used, e.g. hydrochloric acid.

The obtained compound of Formula H may be further reacted with a suitable substituted silane, e.g trimethyl sililonitrile (TMSCN), in a presence of a suitable primary or secondary amine, e.g. aniline, piperidine, ethylamine, propylamine, ethylpropylamine, dipropylamine, in a suitable solvent under acidic conditions, e.g. in acetic acid, trifluoroacetic acid, benzoic acid. The reagents may be combined at a temperature lower than 60° C., preferably lower than 40° C., further preferably between 0° C. and 40° C. and most preferably between 10° C. and 20° C. The reaction may be kept for about 6-18 hours, preferably for about 10-14 hours. After neutralizing the acid, the reaction mixture may be extracted into an apolar solvent, such as dichloromethane, to yield the nitrile compound of formula J, which may be used without further purification.

The nitrile compounds of formula J may be further converted into the compounds of general Formula (Ic) according to the Scheme 4a below:

Scheme 4a

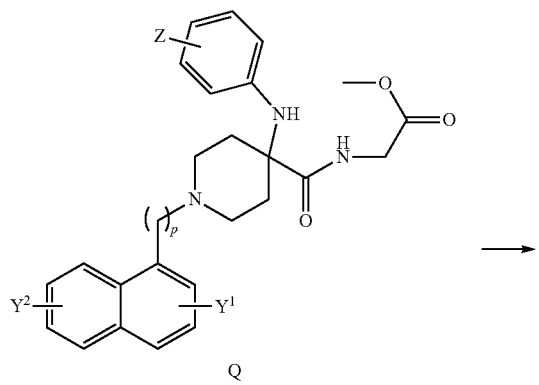

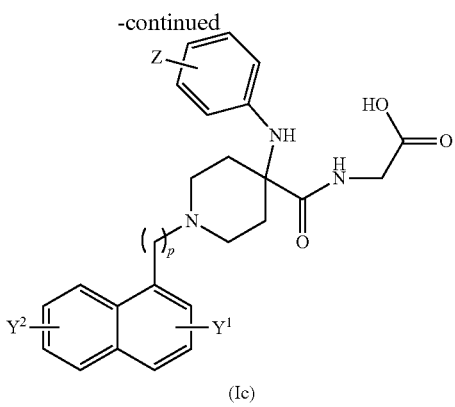

(Ic)

The compound of the formula K is prepared by hydrolyzing the nitrile compound of formula J in a strong acid, e.g. in concentrated sulfuric acid, nitric acid, hydrobromic acid (HBr) and hydrochloric acid (HCl). The reaction may be kept for about 6-18 hours, preferably for about 10-14 hours. After neutralization of the reaction mixture, the compound of the formula K can be purified, e.g. by reverse-phase preparative HPLC.

The compound of the formula K may be further hydrolyzed into the compound of formula N, e.g. with potassium hydroxide in a polar solvent, e.g. in ethylene glycol. The reagents may be combined at a temperature between 110° C. and 170° C. and most preferably between 140° C. and 160° C. The reaction may be kept for about 6-18 hours, preferably for about 10-14 hours. After cooling of the reaction mixture, the compound of the formula N can be purified, e.g. by reverse-phase preparative HPLC. The compound of formula N may then be reacted with methyl glycinate in DMF in presence of a coupling agent, e.g. 1-[Bis(dimethylamino) methylene]-1H-1,2,3-triazolo[4,5-b]-pyridinium-3-oxid hexafluorophosphate (known as HATU) and diisopropyl ethylamine, for about 6-18 hours, preferably for about 10-14 hours, and purified, e.g. by reverse-phase preparative HPLC, to furnish the compound of formula Q. Additional coupling agents that may be used are N,N'-dicyclohexylcarbodiimide (DCC), 3-(ethyliminomethyleneamino)-N,N-dimethylpropan-1-amine (EDC), 3-[bis(dimethylamino)-methyliumyl]-3H-benzotriazol-1-oxide hexafluorophosphate (HBTU), 1-[bis(dimethylamino)methylene]-1H-1,2,3-triazolo[4,5-b] pyrid-inium 3-oxid hexafluorophosphate (HATU), 1-[(1-(cyano-2-ethoxy-2-oxoethylideneaminooxy)-dimethylamino-morpholinomethylene)]-methanaminium hexafluorophosphate (COMU).

Finally, the compound of formula Q may be hydrolyzed with a base, e.g. lithium hydroxide, to release the methyl ester and furnish the crude compound of the general Formula (Ic), e.g. in an aprotic solvent, such as tetrahydrofuran, for about 6-18 hours, preferably for about 10-14 hours. The reaction mixture may then be neutralized to pH about 7, and then purified, e.g. by a preparative HPLC, to furnish the compound of the general Formula (Ic).

Compounds of general formula (Id) are prepared according to the method described for the compounds of general formulae (Ia) and (Ib).

In the reactions described hereinabove, any reactive group such as for example an amino, alkylamino, hydroxy or carboxy group, may be protected during the reaction by conventional protecting groups which are cleaved after the reaction, by methods known in the art.

The invention also relates to the stereoisomers, such as diastereomers and enantiomers, mixtures and salts, particularly the physiologically acceptable salts, of the compounds of general Formulae (I), (Ia), (Ib), (Ic), and (Id), and of the compounds of structural formulae 1, 2, 3, 4, 5, 6, 7, 8 and 9.

The compounds of general Formulae (I), (Ia), (Ib), (Ic), and (Id), or intermediate products in the synthesis of compounds of general Formulae (I), (Ia), (Ib), (Ic), and (Id), may be resolved into their enantiomers and/or diastereomers on the basis of their physical-chemical differences using methods known in the art. For example, cis/trans mixtures may be resolved into their cis and trans isomers by chromatography. For example, enantiomers may be separated by chromatography on chiral phases or by recrystallisation from an optically active solvent or by enantiomer-enriched seeding.

The compounds of general Formulae (I), (Ia), (Ib), (Ic), and (Id), and the compounds of structural formulae 1, 2, 3, 4, 5, 6, 7, 8 and 9, may be converted into the salts thereof, particularly physiologically acceptable salts for pharmaceutical use. Suitable salts of the compounds of general Formulae (I), (Ia), (Ib), (Ic), and (Id), and of the compounds of structural formulae 1, 2, 3, 4, 5, 6, 7, 8 and 9, may be formed with organic or inorganic acids, such as, without being limited to hydrochloric acid, hydrobromic acid, sulphuric acid, phosphoric acid, lactic acid, acetic acid, succinic acid, citric acid, palmitic acid or maleic acid. Compounds of general Formulae (I), (Ia), (Ib), (Ic) and (Id), containing a carboxy group, may be converted into the salts thereof, particularly into physiologically acceptable salts for pharmaceutical use, with organic or inorganic bases. Suitable bases for this purpose include, for example, sodium hydroxide, potassium hydroxide, ammonium hydroxide, arginine or ethanolamine.

According to another aspect provided herein are uses of the compounds of general Formulae (I), (Ia), (Ib), (Ic), (Id), (II) and (IIa), such as, without being limited to, the compounds of structural formulae 1, 2, 3, 4, 5, 6, 7, 8, 9, 10 and 11, for example as oligomerization inhibitors of Voltage-Dependent Anion Channel (VDAC).

Another aspect of the invention relates to the use of compound according to general Formula (II) as defined below, in the preparation of medicaments for treatment of diseases as described herein.

Formula (II)

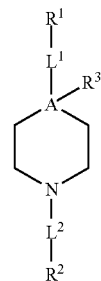

wherein:

A is carbon (C) or nitrogen (N);

$R^3$ is hydrogen or heteroalkyl group comprising 3-12 atoms other than hydrogen, wherein at least one is a heteroatom, preferably selected from nitrogen, sulfur and oxygen; wherein when A is nitrogen (N), $R^3$ is absent;

$L^1$ is a linking group which may be absent or present, but if present is selected from an amino linking group —$NR^4$—, wherein R⁴ is hydrogen; a $C_{1-n}$-alkylene, wherein n is an integer from 2 to 5, inclusive; or a substituted alkyl, $CH_2$—R wherein R is a functional group selected from hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl; preferably R⁴ is hydrogen, optionally L¹ forming a ring with R³;

R¹ is an aromatic moiety, preferably phenyl, which may be substituted with one or more of $C_{1-2}$-alkoxy, $C_{1-2}$-perfluoroalkoxy; preferably R¹ is a phenyl substituted trifluoromethoxy; preferably R¹ is a phenyl substituted with one trifluoromethoxy, preferably at the para position;

L² is a linking group consisting of 4-10 atoms, preferably of 5-6 atoms, optionally forming a closed ring, whereof at least one of the atoms is nitrogen, said nitrogen forming part of an amide group, preferably said linking group is selected from the group consisting of an $C_{4-6}$-alkylamidylene or a pyrrolidinylene, said linking group optionally substituted with one or two of alkyl, hydroxy, oxo or thioxo group; more preferably L² is selected from butanamidylene, N-methylbutanamidylene, N,N-dimethylbutanamidylene, 4-hydroxybutanamidylene, 4-oxobutanamidylene, 4-hydroxy-N-methylbutanamidylene, 4-oxo-N-methylbutanamidylene, 2-pyrrolidonylene, pyrrolidine-2,5-dionylene, 5-thioxo-2-pyrrolidinonylene and 5-methoxy-2-pyrrolidinonylene; or L² is $C_{1-n}$ alkylene, wherein n is an integer between 2 and 5, inclusive, preferably methylene (—$CH_2$—); said linking group L² bonds piperidine or piperazine moiety at nitrogen (N) atom; and R² is an aryl, preferably a phenyl or a naphthyl, optionally substituted with halogen, optionally when R² is a phenyl it is substituted with halogen, preferably chlorine, preferably at the para position, further optionally when R² is naphthyl, L² is an alkylenyl group, preferably methylene (—$CH_2$—).

Another aspect of the invention relates to the use of compound according to general Formula (IIa) as defined below, in the preparation of medicaments for treatment of diseases as described herein.

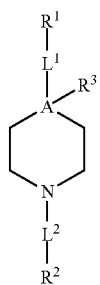

Formula (IIa)

wherein:

A is carbon (C);

R³ is hydrogen or heteroalkyl chain comprising 3-12 atoms, wherein at least one is a heteroatom, selected from nitrogen, sulfur and oxygen;

L¹ is a linking group which is an amino linking group —NR⁴—, wherein R⁴ is hydrogen, $C_{1-n}$-alkyl, wherein n is an integer from 2 to 5, inclusive, and $CH_2$—R, wherein R is a functional group selected from hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl;

when R³ is hydrogen, then L¹ is —NR⁴—; when R³ is heteroalkyl group comprising 3-12 atoms, then L¹ is forming a ring with R³;

R¹ is an aromatic moiety, which is optionally substituted with one or more of $C_{1-2}$-alkoxy, e.g. haloalkoxy, such as $C_{1-2}$-perfluoroalkoxy;

L² is a linking group consisting of 4-10 atoms, optionally forming a closed ring, whereof at least one of the atoms is nitrogen, said nitrogen forming part of an amide group or L² is $C_{1-2}$ alkyl or $C_{1-n}$ alkylene, wherein n is an integer between 2 and 5, inclusive; said linking group L² bonds piperidine or piperazine moiety at nitrogen (N) atom; preferably, L² is selected from butanamidylene, N-methylbutanamidylene, N,N-dimethylbutanamidylene, 4-hydroxybutanamidylene, 4-oxobutanamidylene, 4-hydroxy-N-methylbutanamidylene, 4-oxo-N-methylbutanamidylene, 2-pyrrolidonylene, pyrrolidine-2,5-dionylene, 5-thioxo-2-pyrrolidinonylene and 5-methoxy-2-pyrrolidinonylene; and R² is an aryl, optionally substituted with halogen, optionally when R² is a phenyl it is substituted with halogen, further optionally when R² is naphthyl, L² is an alkylenyl group. In a specific embodiment, R³ is hydrogen, L¹ is —NH—, and R¹ is a phenyl substituted with trifluoromethoxy.

The invention also relates to use of the stereoisomers, enantiomers, mixtures thereof, and salts, particularly the physiologically acceptable salts, of the compounds of general Formulae (II) and (IIa).

In a specific embodiment, there is provided use of compounds according to the general Formulae (II) and (IIa), having the structural Formulae 10 and 11:

Formula 10

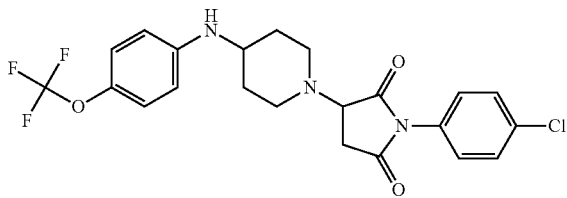

The compound of Formula 10 is also identified herein as AKOS022 or AKOS022075291.

Formula 11

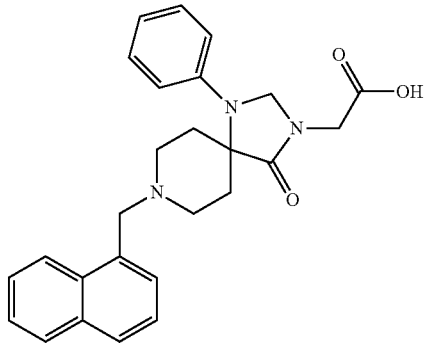

The compound of Formula 11 is also identified herein as DIV 00781.

The compounds of general Formulae (II) and (IIa), such as, without being limited to, the compounds of structural formulae 1, 2, 3, 4, 5, 6, 7, 8, 9, 10 and 11, may be converted into the salts thereof, particularly physiologically acceptable salts for pharmaceutical use. Suitable salts of the compounds of general Formulae (II) and (IIa), such as, without being limited to, the compounds of structural formulae 1, 2, 3, 4, 5, 6, 7, 8, 9, 10 and 11, may be formed with organic or inorganic acids, such as, without being limited to hydrochloric acid, hydrobromic acid, sulphuric acid, phosphoric acid, lactic acid, acetic acid, succinic acid, citric acid, palmitic acid or maleic acid. Compounds of general Formulae (II) and (IIa) containing a carboxy group, may be converted into the salts thereof, particularly into physiologically acceptable salts for pharmaceutical use, with organic or inorganic bases. Suitable bases for this purpose include, for example, sodium salts, potassium salts, arginine salts, ammonium salts, or ethanolamine salts.

The compounds of general Formulae (I), (Ia), (Ib), (Ic), (Id), (II) and (IIa), especially the specific compounds of Formulae 1, 2, 3, 10 and 11, are inhibitors of Voltage-Dependent Anion Channel (VDAC) oligomerization and apoptosis. The effect of the compounds of the invention and of the specific compounds of formulae 1, 2, 3, 10 and 11 on VDAC oligomerization, i.e. their ability to inhibit VDAC oligomerization, is determined by Bioluminescence Resonance Energy Transfer (BRET2) technology that allows to directly monitor the oligomeric state of VDAC molecules in the native membrane in cells in live. BRET2 screening may be carried out as described in the art (Keinan et al., (2010) Oligomerization of the mitochondrial protein voltage-dependent anion channel is coupled to the induction of apoptosis. Mol Cell Biol 30, 5698-5709).

The compounds of general Formula (II) and (IIa) have ICso values for several activities in the range from 0.1 µM to 10 µM.

The direct interaction between VDAC and the compounds of general Formulae (I), (Ia), (Ib), (Ic), (Id), (II) and (IIa), especially the specific compounds of Formulae 1, 2, 3, 10 and 11, may be measured by assessing VDAC channel conductance, following its reconstitution into a planar lipid bilayer (PLB). The compounds of the general Formulae (I), (Ia), (Ib), (Ic), (Id), (II) and (IIa), interact with VDAC and reduce its channel conductance. To obtain quantitative parameters of this interaction and derive a dissociation constant, e.g. a microscale thermophoresis (MST) interaction assay may be performed. In this manner, dissociation values are derived from the curves showing the affinity of the compounds of the invention to VDAC.

The compounds of general Formulae (I), (Ia), (Ib), (Ic), (Id), (II) and (IIa), especially the specific compounds of Formulae 1, 2, 3, 10 and 11, were found to protect cells against apoptotic cell death. The ability of the compounds of general Formulae (I), (Ia), (Ib), (Ic), (Id), (II) and (IIa) to inhibit apoptosis may be analyzed by annexin-V/propidium iodide (PI) staining and flow cytometry.

One of the ways cell apoptosis is activated is by release of Cytochrome c (Cyto c) from the mitochondria into cytosol. The compounds of general Formulae (I), (Ia), (Ib), (Ic), (Id), (II) and (IIa), especially the specific compounds of Formulae 1, 2, 3, 10 and 11, were found to inhibit the release of Cyto c from mitochondria, as induced by apoptosis stimuli, thereby protecting cells against apoptotic cell death. Cyto c released to the cytosol may be analyzed by immunoblotting using Cyto c-specific antibodies.

Apoptosis induction was shown to disrupt cell $Ca^{2+}$ homeostasis and energy production. Indeed, many anticancer drugs and other cytotoxic agents, such as thapsigargin, staurosporine, $As_2O_3$, and selenite, induce apoptotic cell death, as well as disrupt cell $Ca^{2+}$ homeostasis (Keinan et al., (2013) The role of calcium in VDAC1 oligomerization and mitochondria-mediated apoptosis. Biochim Biophys Acta 1833, 1745-1754)). The compounds of general Formulae (I), (Ia), (Ib), (Ic), (Id), (II) and (IIa), especially the specific compounds of Formulae 1, 2, 3, 10 and 11, were found to inhibit the elevation in intracellular calcium ions concentration ($[Ca^{2+}]i$) elicited by apoptosis stimuli. Increased $[Ca^{2+}]i$ is associated with an increase in mitochondrial $Ca^{2+}$, a process expected to lead to dissipation of the mitochondrial potential (m$\Delta\Psi$) (Baumgartner et al., (2009) Calcium elevation in mitochondria is the main $Ca^{2+}$ requirement for mitochondrial permeability transition pore (mPTP) opening. J Biol Chem 284, 20796-20803). The compounds of general Formulae (I), (Ia), (Ib), (Ic), (Id), (II) and (IIa), especially the specific compounds of Formulae 1, 2, 3, 10 and 11, were found to be effective in preventing the decrease in m$\Delta\Psi$ elicited by a cytotoxic agent. The ability of the compounds of the invention to prevent the decrease in m$\Delta\Psi$ induced by cytotoxic agent may be measured using tetramethylrhodamine methylester (TMRM).

The compounds of general Formulae (I), (Ia), (Ib), (Ic), (Id), (II) and (IIa), especially the specific compounds of Formulae 1, 2, 3, 10 and 11, are inhibitors of overall cellular reactive oxidative species (ROS) production and of mitochondrial ROS production. The effect of the compounds of general Formulae (I), (Ia), (Ib), (Ic), (Id), (II) and (IIa) especially the specific compounds of Formulae 1, 2, 3, 10 and 11, on inhibition of cellular ROS production may be determined by 2',7' dichlorodihydrofluorescein (DCF) fluorescence. The effect of the compounds of general Formulae (I), (Ia), (Ib), (Ic), (Id) and (II), especially the specific compounds of Formulae 1, 2, 3, 10 and 11, as inhibitors of mitochondrial ROS production may be measured by Mito-SOX Red, a mitochondrial superoxide indicator.

In view of the ability of the compounds of general Formulae (I), (Ia), (Ib), (Ic), (Id), (II) and (IIa), especially the specific compounds of Formulae 1, 2, 3, 10 and 11, to inhibit one or more of the oligomerization of VDAC and/or of the channel ion conductance of VDAC or apoptosis and/or the release of Cyto c from mitochondria and/or the elevation in intracellular calcium concentration ($[Ca^{2+}]i$) elicited by a cytotoxic agent and/or production of reactive oxidative species (ROS) the compounds of general Formulae (I), (Ia), (Ib), (Ic), (Id), (II) and (IIa), especially the specific compounds of Formulae 1, 2, 3, 10 and 11, and the pharmaceutically acceptable salts thereof, may be suitable for treating and/or preventing all those conditions or diseases that can be influenced by inhibiting one or more of oligomerization of VDAC, apoptosis, release of Cyto c from mitochondria, elevation in intracellular calcium concentration ($[Ca^{2+}]i$) and production of reactive oxidative species (ROS). Therefore the compounds according to general Formulae (I), (Ia), (Ib), (Ic), (Id), (II) and (IIa), especially the specific compounds of Formulae 1, 2, 3, 10 and 11, and the pharmaceutically acceptable salts thereof, are particularly suitable for the prevention or treatment of diseases or conditions associated with enhanced apoptosis, such as, without being limited to, neurodegenerative and cardiovascular diseases and disorders. The compounds of general Formulae (I), (Ia), (Ib), (Ic), (Id), (II) and (IIa), especially the specific compounds of Formulae 1, 2, 3, 10 and 11, and the pharmaceutically acceptable salts thereof, are also particularly suitable for the prevention or treatment of diseases or conditions such as Alzheimer's disease, Parkinson's disease, cardiac hypertrophy, heart failure, myocardial infarction, ischemia/reperfusion injury, apoptosis, and autophagy of cardiac myocytes, atrial fibrillation (AF), cardiac arrhythmia, and related diseases. It has been found that the treatment with a compound of Formula 1 improved the learning and memory task of Alzheimer's disease-like transgenic mice, to resemble those of wild type mice, as described in the Examples below.

The compounds of general Formulae (I), (Ia), (Ib), (Ic), (Id), (II) and (IIa), such as, without being limited to, the compounds of structural formulae 1, 2, 3, 4, 5, 6, 7, 8, 9, 10 and 11, especially the specific compounds of Formulae 1, 2, 3, and 11, and the pharmaceutically acceptable salts thereof, may be formulated in a pharmaceutical composition, optionally comprising other active substances, and one or more of inert conventional excipients, as known to the skilled artisans. The pharmaceutical compositions may be prepared according to the general guidance provided in the art, e.g. by Remington, The Science and Practice of Pharmacy (formerly known as Remington's Pharmaceutical Sciences), ISBN 978-0-85711-062-6. The pharmaceutical compositions, e.g. in the form solid dosage forms, topical dosage form, and/or parenteral dosage forms, e.g. tablets, capsules, creams, ointments, patches, injections, and others as known in the art constitute another aspect of the invention.

Particularly, the compounds of general Formulae (I), (Ia), (Ib), (Ic), (Id), (II) and (IIa), particularly of structural formulae 1, 2, 3, 4, 5, 6, 7, 8, 9, 10 and 11, especially the specific compounds of Formulae 1, 2, 3, 10 and 11, and the pharmaceutically acceptable salts thereof, may be formulated as nanoparticles. The nanoparticles may be prepared in well-known polymers, e.g. polylactic-co-glycolic acid, e.g., as described in H. K. Makadia, S. J. Siegel, Poly Lactic-co-Glycolic Acid (PLGA) as Biodegradable Controlled Drug Delivery Carrier, Polymers (Basel), 3 (2011) 1377-1397; and others. Generally, the compounds may be co-dissolved with the polymer in a suitable organic solvent, and the organic phase may be then dispersed in an aqueous phase comprising stabilizers and/or surface active agents. The stabilizers may be, e.g. polyvinyl alcohol, with molecular weights from about 89000 to 98000, and hydrolysis degree from about 99%. Upon evaporation of organic solvent from the aqueous phase, the nanoparticles may be purified, e.g. by centrifugation and washing.

The encapsulated compounds, e.g. in form of nanoparticles, of general Formulae (I), (Ia), (Ib), (Ic), (Id), (II) and (IIa), such as, without being limited to, the compounds of structural formulae 1, 2, 3, 4, 5, 6, 7, 8, 9, 10 and 11, especially the specific compounds of Formulae 1, 2, 3, 10 and 11, and the pharmaceutically acceptable salts thereof, may be advantageously used in various routes of administration. Intranasal route may be suitable mode of administration in this regard. Alternatively, the nanoparticles may be administered systemically to accumulate in cancerous tissues.

The dose of compounds of general Formulae (I), (Ia), (Ib), (Ic), (Id), (II) and (IIa), such as, without being limited to, the compounds of structural formulae 1, 2, 3, 4, 5, 6, 7, 8, 9, 10 and 11, especially the specific compounds of Formulae 1, 2, 3, and 11, and the pharmaceutically acceptable salts thereof, required to achieve treatment or prevention of a disease or a disorder or a condition usually depends on the pharmacokinetic and pharmacodynamic properties of the compound which is to be administered, the patient, the nature of the disease, disorder or condition and the method and frequency of administration. Suitable dosage ranges for compounds of general Formulae (I), (Ia), (Ib), (Ic), (Id), (II) and (IIa), such as, without being limited to, the compounds of structural formulae 1, 2, 3, 4, 5, 6, 7, 8, 9, 10 and 11, especially the specific compounds of Formulae 1, 2, 3, 10 and 11, and the pharmaceutically acceptable salts thereof, may be from 1.0 to 100 mg/kg body weight.

Compounds of Formulae (I), (Ia-d), (II) and (IIa), bearing at least one fluorine atom, e.g. as part of trifluoromethyl group, such as, without being limited to, the compounds of structural formulae 1, 2, 4, 5, 6, 7, 8, 9, and 10, especially the specific compounds of Formulae 1, 2, and 10, may be suitable as diagnostic agents for Positron Emission Tomography. For this purpose these compounds may be modified or synthesized with $^{18}F$ isotope, as known in the art. These 18-fluorinated compounds may be suitable for imaging of VDAC overexpression in living organisms. Particularly, 18-fluorinated compounds of the general Formulae (I), (Ia), (Ib), (Ic), (Id), (II) and (IIa) may be used to detect pathological conditions or changes due to treatments, particularly for early detection of conditions, e.g. Alzheimer's Disease, cardiovascular diseases, changes of VDAC expression pattern in pancreatic beta cells, and other tissues.

Accordingly, in another aspect there is provided a method for preventing or treating a disease selected from the list consisting of neurodegenerative diseases and disorders, cardiovascular diseases and disorders, Alzheimer's disease, Parkinson's disease, cardiac hypertrophy, heart failure, myocardial infarction, ischemia/reperfusion injury, apoptosis, autophagy of cardiac myocytes, atrial fibrillation (AF), and cardiac arrhythmia, comprising administering to the subject in need thereof a therapeutically effective amount of a compound of general formulae (Ia), (Ib), (Ic), (Id), (II) and (IIa), as defined herein.

EXAMPLES

Materials

Carbonyl cyanide m-chlorophenyl hydrazone (CCCP), carboxymethyl-cellulose (CMC), cisplatin, cytochalasin B, dimethyl sulfoxide (DMSO), DL-dithiothreitol (DTT), EDTA, HEPES, leupeptine, phenylmethylsulfonyl fluoride (PMSF), N-decane, sodium selenite, soybean asolectin, staurosporine (STS), tetramethylrhodamine methylester (TMRM) and Tris were purchased from Sigma (St. Louis, Mo.). N,N-Lauryl-(dimethyl)-amineoxide (LDAO) was obtained from Fluka (Bucks, Switzerland). Coelenterazine (Deep Blue C [DBC]) was obtained from Bioline (Taunton, Mass.). Hydroxyapatite (Bio-Gel HTP) was procured from Bio-Rad Laboratories (Hercules, Calif.). Digitonin came from Calbiochem-Novobiochem (Nottingham, UK). Celite was purchased from the British Drug Houses (London, UK). Rabbit monoclonal antibodies against VDAC1 (ab154856) and mouse monoclonal antibodies against GAPDH (ab9484) came from Abcam (Cambridge, UK). Monoclonal antibodies against actin were obtained from Millipore (Billerica, Mass.) and anti-Cytochrome c antibodies (556433) were obtained from BD Bioscience (San Jose, Calif.). Polyclonal anti-AIF (Apoptosis Inducing Factor) antibodies came from R&D Systems (Minneapolis, Minn.). Fluo-4-AM™ (CAS name/number: Glycine, N-[4-[6-[(acetyloxy)methoxy]-2,7-difluoro-3-oxo-3H-xanthen-9-yl]-2-[2-[2-[bis[2-[(acetyloxy)methoxy]-2-oxoethyl]amino]-5-methylphenoxy]ethoxy]phenyl]-N-[2-[(acetyloxy)methoxy]-2-oxoethyl]-, (acetyloxy)methyl ester 273221-67-3), carboxy-H2DCFDA™ (5-(and-6)-carboxy-2",7"-dichlorodihydrofluorescein diacetate (carboxy-H2DCFDA)

and MitoSOX™ Red (red mitochondrial superoxide indicator) were acquired from Invitrogen (Grand Island, N.Y.). Horseradish peroxidase (HRP)-conjugated anti-mouse and anti-rabbit antibodies were obtained from Promega (Madison, Wis.). Ethylene glycol bis[succinimidylsuccinate] (EGS) was obtained from Pierce (Rockford, Ill.). Annexin V-fluorescein isothiocyanate (FITC) was from Enzo Life Sciences (Lausen, Switzerland). Dulbecco's modified Eagle's medium (DMEM) and the supplements fetal bovine serum (FBS), L-glutamine and penicillin-streptomycin were purchased from Biological Industries (Beit-Haemek, Israel). The compound of Formula 10 (AKOS022) was obtained from AKosConsulting & Solutions GmbH (Germany), under catalogue number AKOS022075291. Polylactic-co-glycolic acid (poly-D,L-lactide-co-glycolide, 30,000-60,000 Da) was obtained from Sigma. Polyvinyl alcohol, Mw 89000-98000, hydrolysis degree 99%, was provided by Sigma.

Methods

LC-MS Analysis

The chromatography was performed using a regular Bridge C18 column 4.6×50 mm, 3.5 µm, kept at 40° C. The materials were eluted at 2 mL/min, with mixture of 0.01 M aqueous solution of ammonium carbonate and acetonitrile, with acetonitrile ramping from 5% to 100% for periods as described below and eluting with 100% acetonitrile, with detection at the target mass.

Tissue Culture

HEK-293, HeLa, SH-SY5Y and K-Ras-transformed Bax$^{-/-}$/Bak$^{-/-}$ mouse embryonic fibroblast (MEF) cell lines were grown at 37° C. under an atmosphere of 95% air and 5% $CO_2$ in DMEM supplemented with 10% FBS, 2 mM L-glutamine, 1000 U/ml penicillin and 1 mg/ml streptomycin. T-REx-293 cells (HEK cells stably containing the pcDNA6/TR regulatory vector and thus expressing the tetracycline repressor; Invitrogen) stably expressing hVDAC1-shRNA and showing low (10-20%) endogenous VDAC1 expression (referred to herein as T-REx-pS10) were grown under the same conditions as HEK-293 cells, with an addition of 5 µg/ml blasticidin.

VDAC-1 Cross-Linking

Appropriate test cells (2.5-3 mg/ml) in PBS, were harvested after the treatment and incubated with the cross-linking reagent EGS at a ratio of 100-300 µM for sample of 2-3 mg protein/ml concentration (pH 8.3) for 15 minutes. Protein concentration was determined according to Lowry assay. Samples (60-80 µg protein) were subjected to SDS-PAGE by a standard technique and immunoblotting was performed using anti-VDAC1 antibodies. Gels were electro-transferred onto nitrocellulose membranes for immuno-staining. The membranes were incubated with a blocking solution containing 5% non-fat dry milk and 0.1% Tween-20 in Tris-buffered saline, followed by incubation with mono-clonal anti-VDAC1, anti-Cytochrome c, anti-AIF or anti-actin antibodies. Membranes were then incubated with HRP-conjugated anti-mouse or anti-rabbit IgG (1:10,000), serving as secondary antibodies. Antibody labeling was detected by chemiluminiscence. To detect VDAC1 oligomers, membranes were treated with 0.1 M glycine, pH 2.0, prior to immunoblotting and washed several times with 0.1% Tween-20 in Tris-buffered saline. Quantitative analysis of immuno-reactive VDAC1 dimer, trimer and multimer bands was performed using FUSION-FX (Vilber Lourmat, France).

VDAC1 Purification

Briefly, rat liver mitochondria (5 mg/ml) in 10 mM Tris-HCl, pH 7.2, were incubated with 2% LDAO at 0° C. for 20 min, followed by centrifugation (30 min, 14,000 g) and the obtained supernatant was loaded onto a dry celite: hydroxyapatite (2:1) column. VDAC1 was eluted with a solution containing 2% LDAO, 10 mM Tris-HCl, pH 7.2, 50 mM NaCl, and 20 to 22 mM $NaH_2PO_4$, with VDAC1 detection by Coomassie blue staining. The VDAC1-containing fractions were dialyzed against 10 mM Tris-HCl, pH 7.2, and subjected to a second chromatography step on a carboxymethyl-cellulose (CMC) column from which VDAC1 was eluted with a solution containing 10 mM Tris-HCl, pH 7.2, 0.1% LDAO and 500 mM NaCl, detected as above. The VDAC1-containing fractions were collected and used for VDAC1 channel conductance and MST assays.

VDAC1 Channel Conductance

The reconstitution of purified rat VDAC1 into a planar lipid bilayer (PLB) and subsequent single and multiple channel current recordings and data analysis were carried out as follows. Briefly, the PLB was prepared from soybean asolectin dissolved in n-decane (30 mg/ml). Purified VDAC1 (1 ng) was added to the chamber defined as the cis side containing 1 M NaCl, 10 mM Hepes, pH 7.4. Currents were recorded under voltage-clamp using a Bilayer Clamp BC-535B amplifier (Warner Instrument, Hamden, Conn.). The currents, measured with respect to the trans side of the membrane (ground), were low-pass-filtered at 1 kHz and digitized online using a Digidata1440-interface board and pClampex 10.2 software (Axon Instruments, Union City, Calif.).

Microscale Thermophoresis (MST) Analysis

MST analysis was performed using a NanoTemper Monolith NT.115 apparatus. Briefly, purified VDAC1 10 µM was fluorescently labeled using NanoTempers Protein labeling kit BLUE according to manufactures instructions (L001, NanoTemper Technologies). A constant concentration of the protein was incubated with different concentrations of the tested inhibitor in PBS. Afterwards, 3-5 µl of the samples were loaded into a glass capillary (Monolith NT Capillaries) and thermophoresis analysis was performed (LED 20%, IR laser 20%).

Measurement of Superoxide Generation

ROS (reactive oxygen species) production was monitored using the oxidant sensitive dye DCFDA (2',7'-dichlorofluorescein diacetate) fluorescent probe, a cell-permeable indicator of ROS, which is converted by $H_2O_2$ and peroxidases to the DCF (2',7'-dichlorofluorescein) fluorescent derivate. Briefly, untreated and treated cells were incubated with DCFDA (4 µM) for 30 minutes. For mitochondrial accumulated ROS, MitoSOX Red (4 µM), mitochondrial superoxide indicator for live-cell imaging was used according to the manufacturer's protocol (Invitrogen, Grand Island, N.Y.). Fluorescence was measured using a FACSCalibur™ flow cytometer software (BD Biosciences, Franklin Lakes, N.J.).

Mitochondrial Membrane Potential Determination

Mitochondrial membrane potential (mΔΨ) was determined using TMRM (Tetramethylrhodamine, methyl ester, perchlorate), a potential-sensitive dye, and a plate reader. HEK-293 cells were treated with the tested compounds and an apoptotic inducer and subsequently incubated with TMRM (0.5 µM, 20 min). The cells were then washed twice with PBS and examined with FACSCaliburµ flow cytometer software (BD Biosciences, Franklin Lakes, N.J.). CCCP (carbonyl cyanide m-chlorophenyl hydrazine)-mediated ΔΨ dissipation served as control.

Cellular $Ca^{2+}$ Concentration Analysis

Fluo-4 AM™ was used to monitor changes in cytosolic $Ca^{2+}$ levels. Cells, e.g. HeLa cells (1×10$^6$ cells/ml) were harvested after the treatment, collected (1,500×g relative centrifugal force (RCF)) (for 10 min) washed with HBSS (Hanks' Balanced Salt Solution) buffer, pH 7.3-7.4 (5.33 mM KCl, 0.44 mM $KH_2PO_4$, 138 mM NaCl, 4 mM $NaHCO_3$, 0.3 mM $Na_2HPO_4$, 5.6 mM glucose, 0.03 mM phenol red) supplemented with 1.8 mM $CaCl_2$ ($HBSS^+$) and incubated with 2.5 μM Fluo-4 AM™ in 200 μl ($HBSS^+$) buffer in the dark for 30 min at 37° C. After washing the remaining dye, the cells were incubated with 200 μl ($HBSS^+$) buffer and changes in cellular free $Ca^{2+}$ concentration were measured immediately with FACS analysis. At least 10,000 events were recorded on the FL1 detector, represented as a histogram, and analyzed with FACS Calibur flow cytometry software. Positive cells showed a shift to an enhanced level of green fluorescence (FL1).

Cytochrome c Release from Mitochondria

Cells treated with apoptosis inducers in the absence or presence of the tested compounds were harvested, washed twice with PBS, pH 7.4 and gently resuspended at 6 mg/ml in ice-cold buffer (100 mM KCl, 2.5 mM $MgCl_2$, 250 mM sucrose, 20 mM HEPES/KOH pH 7.5, 0.2 mM EDTA, 1 mM dithiothreitol, 1 μg/ml leupeptin, 5 mg/ml cytochalasin B and 0.1 mM PMSF) containing 0.025% digitonin and incubated for 10 min on ice. Samples were centrifuged at 10,000×g (relative centrifugal force—RCF) at 4° C. for 5 min to obtain supernatants (cytosolic extracts free of mitochondria) and pellet (fraction that contains mitochondria). Cytochrome c released to the cytosol was analyzed by immunoblotting using Cytochrome c-specific antibodies. Anti-VDAC1 and anti-GAPDH antibodies were used to verify that the cytosolic extracts are mitochondria-free.

Flow Cytometry Using Propidium Iodide (PI) and Annexin V-FITC Staining

Cells, e.g. HeLa cells ($2\times10^3$), untreated or treated with apoptosis-inducing reagents, were analyzed for apoptotic cell death using PI, annexin V-FITC and flow cytometer analysis. Cells were collected (1500×g for 10 min), washed, and resuspended in 200 μl binding buffer (10 mM HEPES/NaOH, pH 7.4, 140 mM NaCl, and 2.5 mM $CaCl_2$). Annexin V-FITC was added according to the recommended Protocol (Enzo Life Sciences, Switzerland), and the cells were incubated in the dark for 15 min. Cells were then washed with binding buffer and resuspended in 200 μl binding buffer, to which PI was added immediately before flow cytometry analysis. At least 10,000 events were collected, recorded on a dot plot, and analyzed by the FACSCalibur™ flow cytometer software (BD Biosciences, Franklin Lakes, N.J.).

Preparation of Intermediate 1

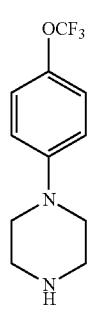

Intermediate 1

Step A

Intermediate 1 was synthesized according to the scheme below.

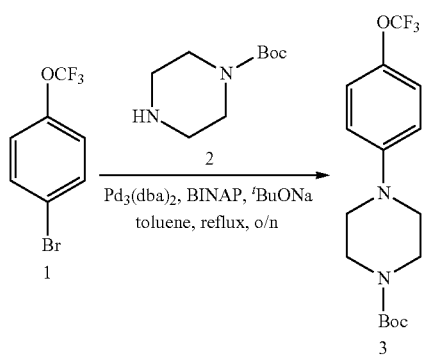 [SMILES: FC(F)(F)Oc1ccc(Br)cc1 ; CC(C)(C)OC(=O)N1CCNCC1 ; CC(C)(C)OC(=O)N1CCN(c2ccc(OC(F)(F)F)cc2)CC1]

The starting material reagent 1 (p-trifluoromethoxy-bromobenzene; 1-Bromo-4-(trifluoromethoxy)benzene) was used. To a solution of reagent 1 (2.41 g, 10 mmol) in toluene (50 mL) were consecutively added the following compounds: reagent 2 (1-Boc-piperazine; tert-butyl piperazine-1-carboxylate) (1.68 g, 9 mmol), $Pd_2(dba)_3$ (tris-(dibenzylidenacetone)dipalladium) (290 mg, 0.5 mmol), 2,2'-bis(diphenylphosphino)-1,1'-binaphthyl (BINAP) (311 mg, 0.5 mmol) and sodium t-butoxide (1.92 g, 20 mmol). The mixture was refluxed under $N_2$ atmosphere overnight. The solvent was evaporated to provide crude reagent 3 (tert-butyl 4-(4-(trifluoromethyl)-phenyl)-piperazine-1-carboxylate) as a residue.

Step B

Reagent 3 was directly used for next step without further purification.

Boc group was removed by acid hydrolysis according to the scheme below

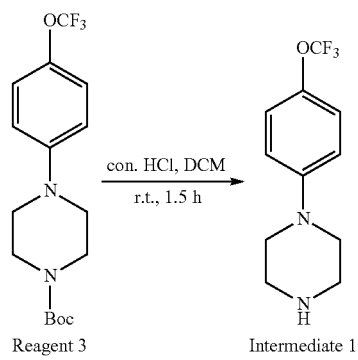 [SMILES: CC(C)(C)OC(=O)N1CCN(c2ccc(OC(F)(F)F)cc2)CC1 ; FC(F)(F)Oc1ccc(N2CCNCC2)cc1]

The mixture comprising crude reagent 3 in 50 mL of concentrated hydrochloric acid and 50 mL of dichloromethane was stirred for 1.5 hours at room temperature. After phase separation, the dichloromethane phase was discarded, and the aqueous phase was evaporated in vacuo to dryness. The residue was dissolved in 50 mL of aqueous sodium hydroxide solution, 2.0 M, and 50 mL dichloromethane were added and stirred for additional 1.5 hours. The organic phase was collected and concentrated in vacuo to provide Intermediate 1 as brown oil (2.0 g, 80% yield for steps A and B).

The Intermediate 1 was analyzed using LC-MS method as described above with ramping over 1.6 minutes and elution for 1.4 minutes, with detection at +246. A representative chromatogram and respective mass spectra of two peaks of interest relating to Intermediate 1 are represented in FIG. 1.

Example 1

Preparation of compound of Formula 2 (VBIT-3, 1-(4-chlorophenyl)-3-(4-(4-(trifluoromethoxy)phenyl)piperazin-1-yl)pyrrolidine-2,5-dione)

The compound of Formula 2 (VBIT-3) was synthesized according to the reaction scheme below:

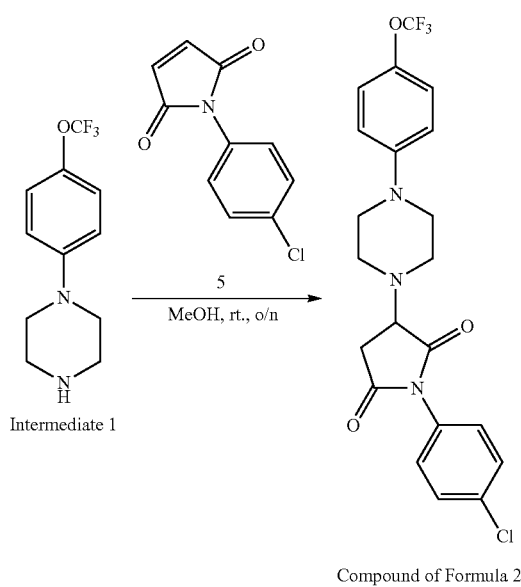 [SMILES: FC(F)(F)Oc1ccc(N2CCNCC2)cc1 ; O=C1C=CC(=O)N1c1ccc(Cl)cc1 ; O=C1CC(N2CCN(c3ccc(OC(F)(F)F)cc3)CC2)C(=O)N1c1ccc(Cl)cc1]

Compound of Formula 2

To a solution of Intermediate 1 (207 mg, 1 mmol) in methanol (2 mL) was added reagent 5 (1-(4-Chlorophenyl)-1H-pyrrole-2,5-dione) (246 mg, 1 mmol). The reaction was stirred at room temperature overnight. The final mixture was concentrated and purified by preparative reverse-phase HPLC to provide compound of Formula 2 (VBIT-3) as white solid (100 mg, 22% yield).

Figure 2A:
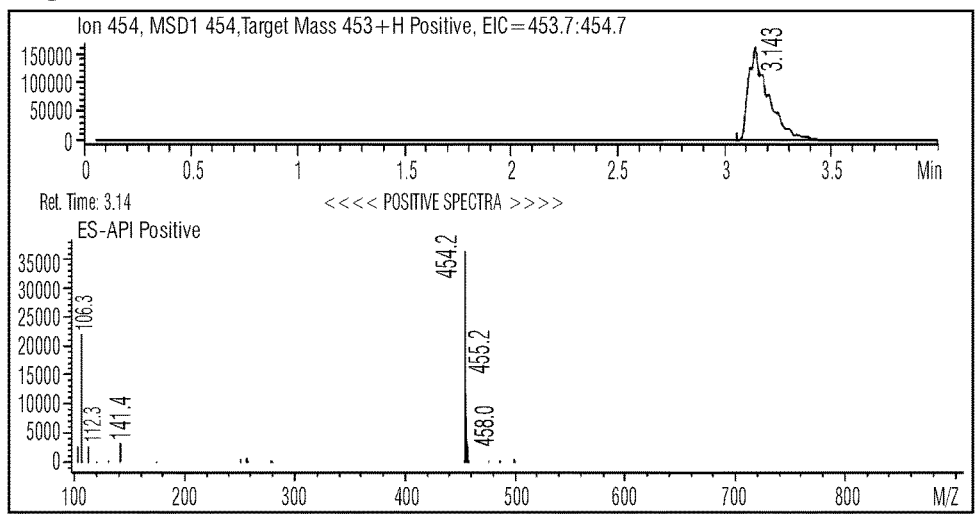
FIG. 2a demonstrates a representative chromatogram and respective mass spectrum of the peak of interest relating to the compound of Formula 2.

The product (compound of Formula 2 (VBIT-3)) was analyzed using LC-MS method as described above with ramping over 3 minutes and elution for 1 minute, with detection at +453. The chromatogram is represented in FIG. 2a.

The NMR spectra were obtained on 400 MHz apparatus (by Varian).

Figure 2B:
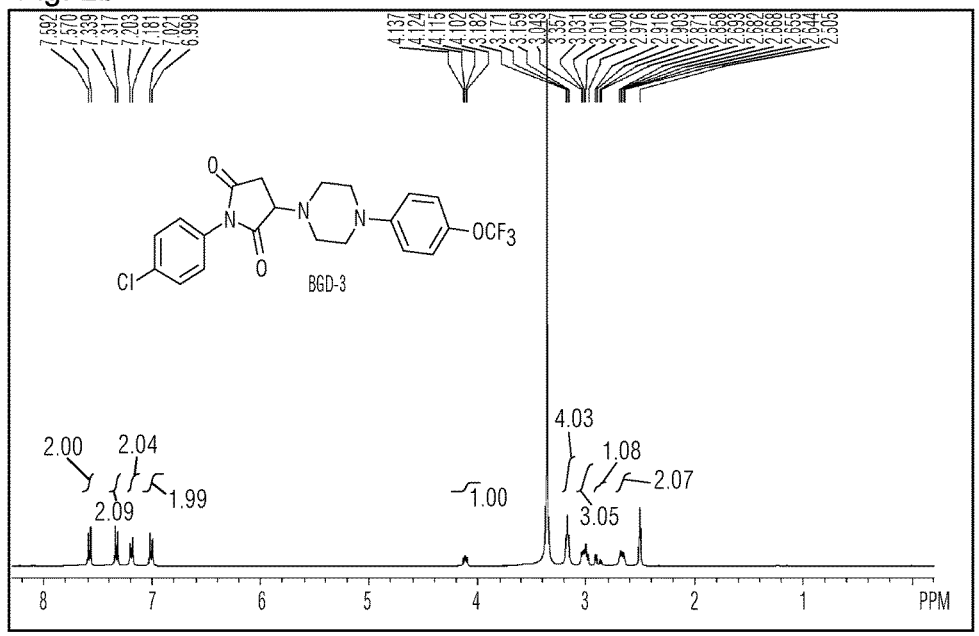
FIG. 2b demonstrates a representative NMR spectrum relating to the compound of Formula 2.

$^1$H NMR (400 MHz, DMSO-$d_6$: δ7.592 (d, J=2.2 Hz, 2H), 7.339 (d, J=2.2 Hz, 2H), 7.201 (d, J=2.2 Hz, 2H), 7.021 (d, J=2.1 Hz, 2H), 4.137 (dd, J=1.3 Hz, 1H), 3.159 (m, J=1.1 Hz, 4H), 3.00 (m, J=2.4 Hz, 3H), 2.871 (m, J=1.3 Hz, H), 2.680 (m, J=2.0 Hz, 2H). The spectrum is shown in the FIG. 2b.

Example 2

Preparation of compound of Formula 1 (VBIT-4, N-(4-chlorophenyl)-4-hydroxy-3-(4-(4-(trifluoromethoxy)phenyl) piperazin-1-yl)butanamide)

The compound of Formula 1 (VBIT-4) was synthesized according to the reaction scheme below:

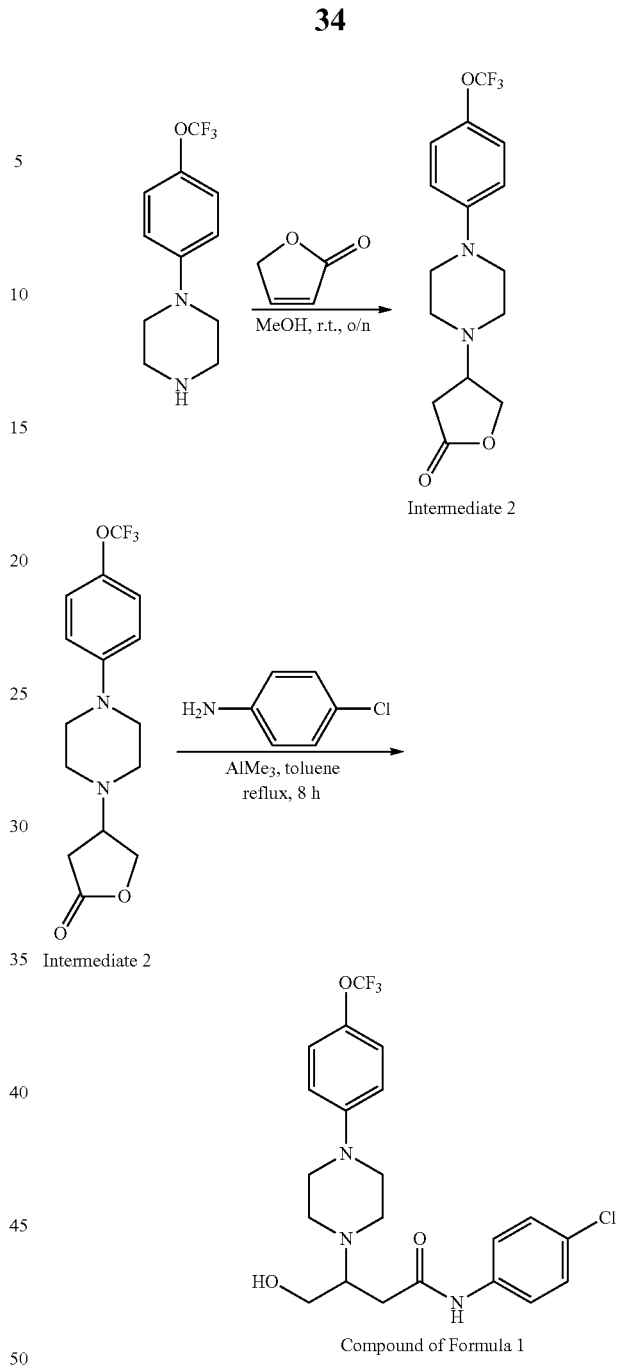

Compound of Formula 1

Step A

A mixture of Intermediate 1 (2.0 g, 8 mmol) and furan-2(5H)-one (2(5H)-Furanone) (1.3 g, 16 mmol) in methanol (MeOH) (5 mL) was stirred at room temperature overnight. The mixture was evaporated in vacuo and the residue was purified by reverse phase preparative HPLC to provide Intermediate 2 [3-(4-(4-(trifluoromethoxy)phenyl)piperazin-1-yl)-dihydrofuran-2(3H)-one) as white solid (1.3 g, 0.4 mmol, 50% yield).

Figure 3:
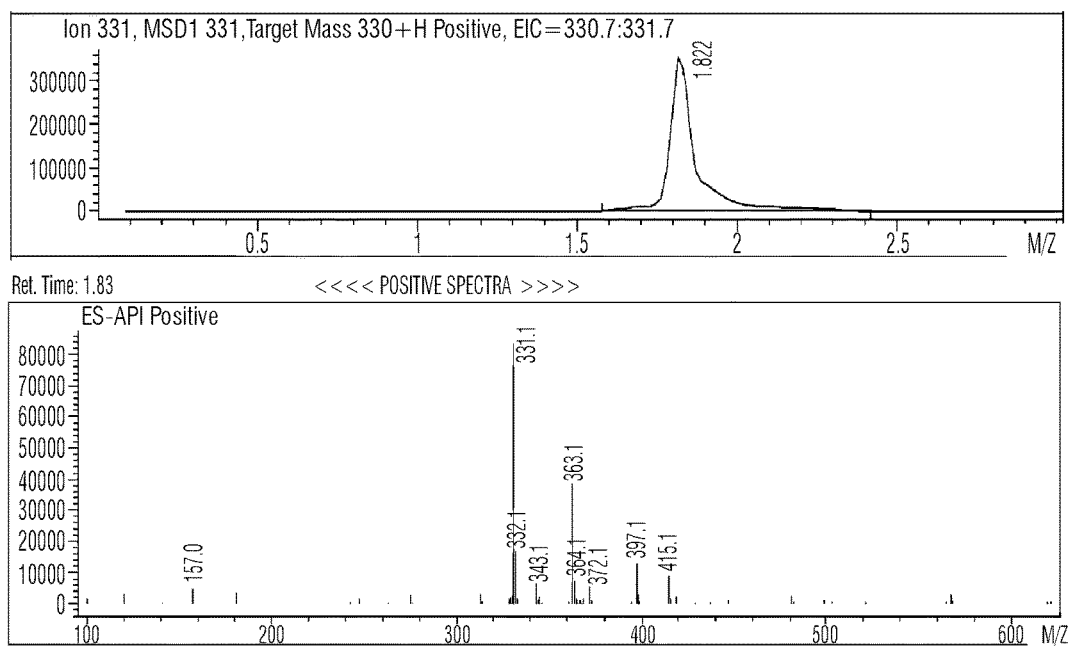
FIG. 3 demonstrates a representative chromatogram and respective mass spectrum of the peak of interest relating to Intermediate 2.

The product (Intermediate 2) was analyzed using LC-MS method as described above with ramping over 1.6 minutes and elution for 1.4 minutes, with detection at +330. The chromatogram is represented in FIG. 3.

Step B

To a solution of 4-chloroaniline (254 mg, 2 mmol) in toluene (5 mL) trimethyl aluminum (AlMe$_3$) was added (2.0

M in toluene, 2 mL). After stirring for 10 minutes, Intermediate 2 (330 mg, 1.0 mmol) was added to the solution and the resulting mixture was heated to 80° C. for 8 hours. After cooling to room temperature, the solvent was evaporated in vacuo and the residue was purified by reverse preparative HPLC to afford the compound of Formula 1 (VBIT-4) as white solid (200 mg, 44% yield).

Figure 4A:
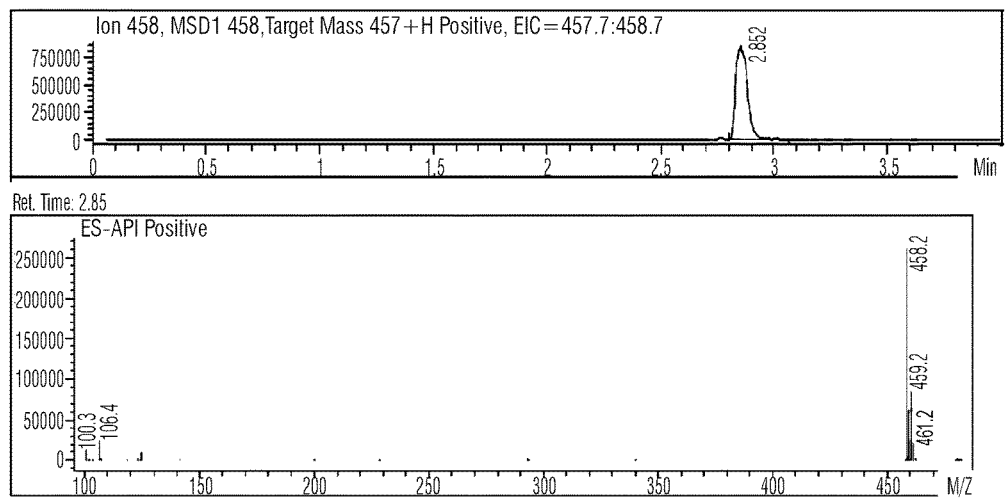
FIG. 4a demonstrates a representative chromatogram and respective mass spectrum of the peak of interest relating to the compound of Formula 1.

The product (Compound of Formula 1) was analyzed using LC-MS method as described above with ramping over 3 minutes and elution for 1 minute, with detection at +457. The chromatogram is represented in FIG. 4a.

The NMR spectra were obtained on 400 MHz apparatus (by Varian).

Figure 4B:
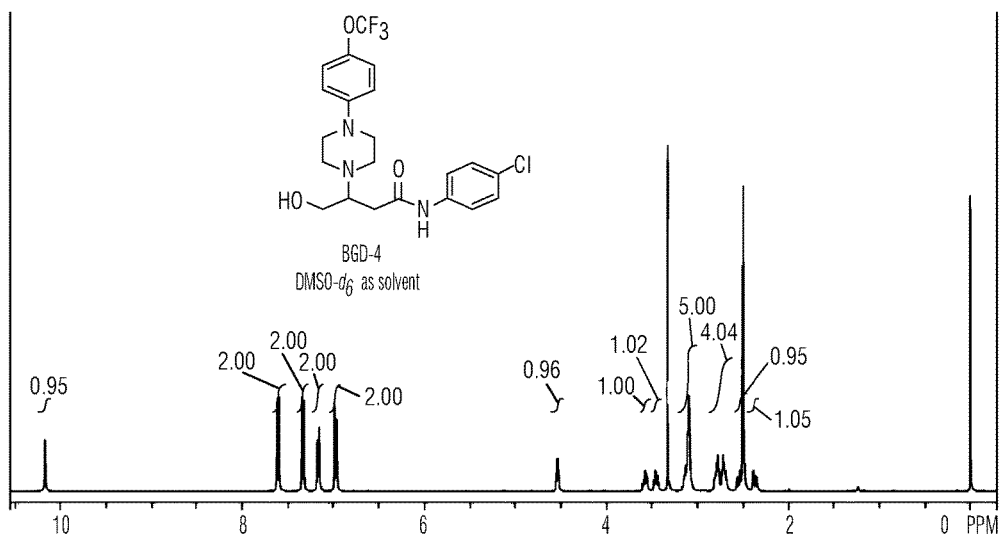
FIG. 4b demonstrates a representative NMR spectrum relating to the compound of Formula 1.

$^1$H NMR (400 MHz, DMSO-d$_6$): δ10.081 (s, H), 7.601 (d, J=0.5 Hz, 2H), 7.341 (d, J=1.2 Hz, 2H), 7.177 (d, J=2.2 Hz, 2H), 6.980 (d, J=2.3 Hz, 2H), 4.538 (dd, J=1.2 Hz, 1H), 3.561 (m, J=1.3 Hz, H), 3.440 (m, J=1.4 Hz, H), 3.112 (m, J=1.2 Hz, 5H), 2.807 (m, J=1.6 Hz, 2H), 2.709 (m, J=1.5, Hz, 2H), 2.400 (m, J=1.4, Hz, H), 2.150 (m, J=1.4, Hz, H). The spectrum is shown in the FIG. 4b.

Example 3

Preparation of compound of Formula 3 (VBIT-12, 2-(1-(naphthalen-1-ylmethyl)-4-(phenylamino)piperidine-4-carboxamido)acetic acid)

Step 1

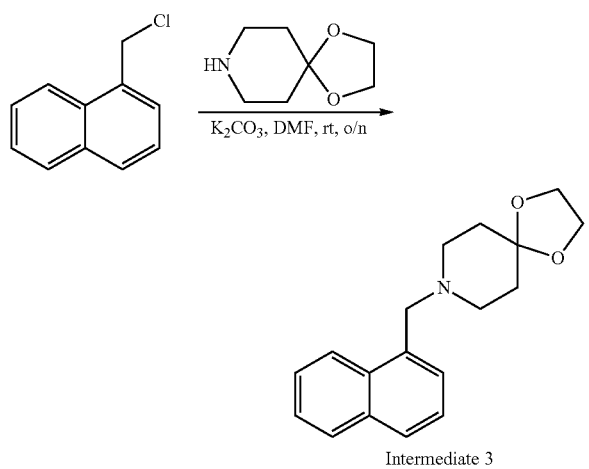 [SMILES: ClCc1cccc2ccccc12 ; C1CC2(CCN1)OCCO2 ; c1ccc2c(CN3CCC4(CC3)OCCO4)cccc2c1]

Intermediate 3

1-(Chloromethyl)naphthalene (8.8 g, 50 mmol) was dissolved in dimethylformamide (DMF) (100 mL), and potassium carbonate (13.8 g, 100 mmol) was added, followed by 4-piperidone ethylene ketal (1,4-dioxa-8-azaspiro[4.5]decane) (7.2 g, 50 mmol). The mixture was stirred at room temperature overnight. The solvent was evaporated in vacuo and the residue was purified by chromatography in silica gel (eluting with dichloromethane) to provide pure naphthylated ketal (Intermediate 3) as white solid (8.5 g, 60% yield).

Figure 5:
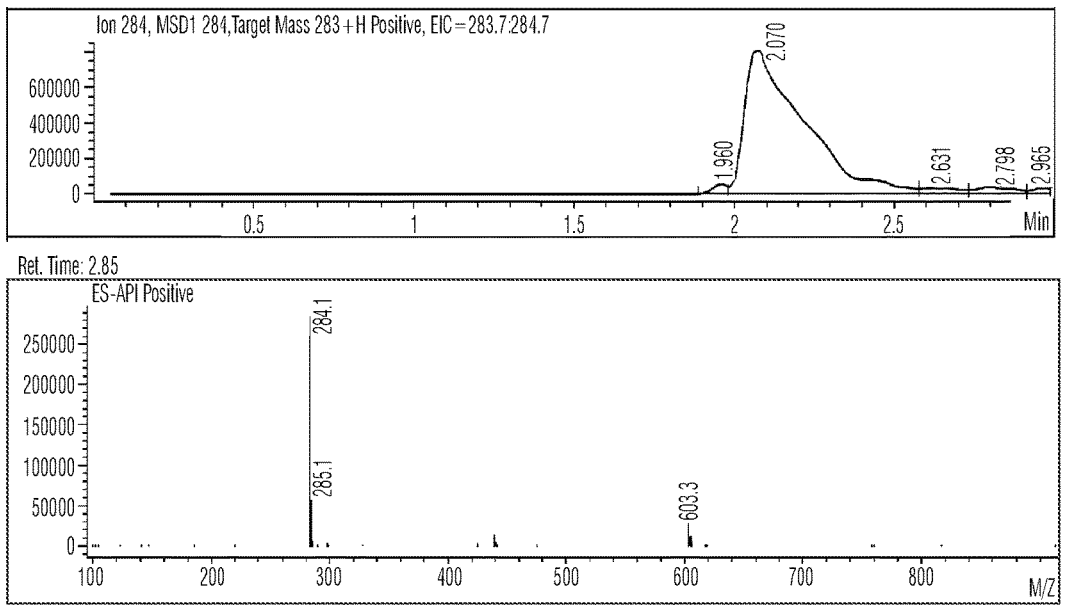
FIG. 5 demonstrates a representative chromatogram and respective mass spectrum of the peak of interest relating to Intermediate 3.

Intermediate 3 was analyzed using LC-MS method as described above with ramping over 1.6 minutes and elution for 1.4 minute, with detection at +283. The chromatogram is represented in FIG. 5.

Step 2

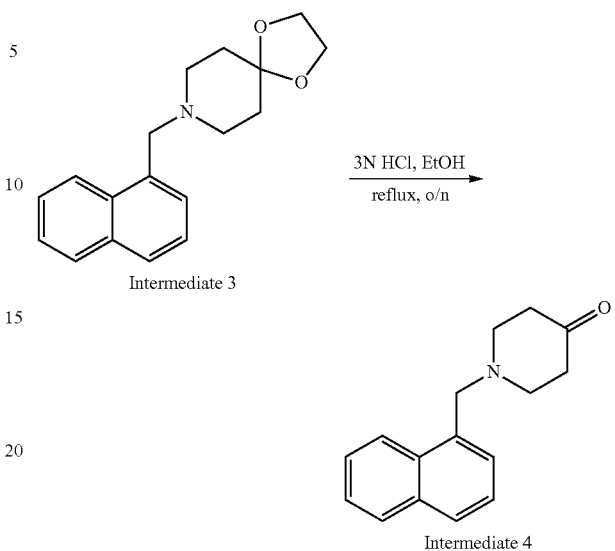

Intermediate 4

A solution of Intermediate 3 (product of Step 1) (1.42 g, 5 mmol) in 20 ml of 3N hydrochloric acid (HCl) in ethanol (EtOH) was refluxed overnight. The resulting mixture was concentrated in vacuo to provide Intermediate 4 (1-(naphthalen-1-ylmethyl)piperidin-4-one), which was used with no further purification.

Figure 6:
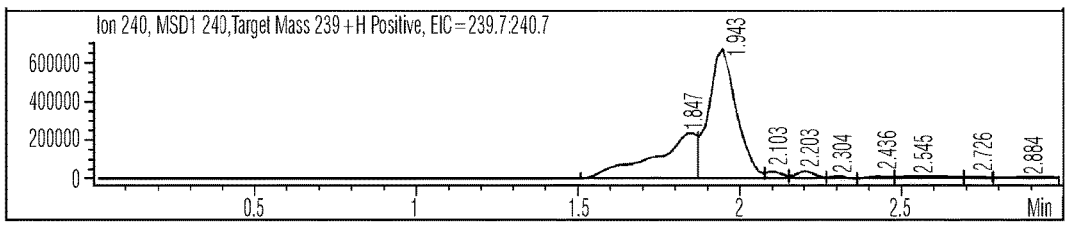
FIG. 6 demonstrates a representative chromatogram and respective mass spectrum of the peak of interest relating to Intermediate 4.

The product (Intermediate 4) was analyzed using LC-MS method as described above with ramping over 1.6 minutes and elution for 1.4 minute, with detection at +239. The chromatogram is represented in FIG. 6.

Step 3

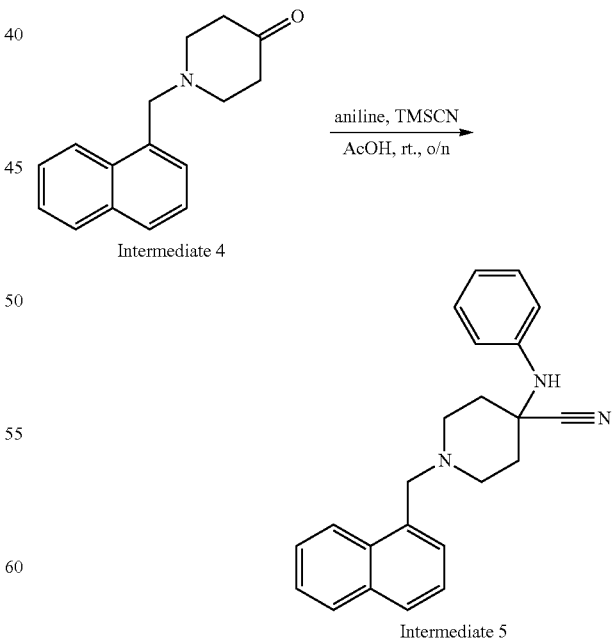

Intermediate 5

Intermediate 4 (N-methylnaphtyl-4-piperidinone) (2.4 g, 10 mmol) and aniline (930 mg, 10 mmol) were dissolved in glacial acetic acid (AcOH) (25 mL). Thereafter, trimethylsilyl cyanide (TMSCN) was added dropwise (1.3 mL, 10 mmol) over a 10-min period, maintaining the temperature below 40° C. using a cold water bath. The solution was stirred overnight and then poured into ammonium hydroxide ice mixture, formed by 50 mL of concentrated ammonium hydroxide solution and 100 g of crushed ice. Additional concentrated ammonium hydroxide was slowly added until pH rose to 10. The resultant mixture was extracted three times with 100 mL of chloroform, and the combined organic layers were dried over sodium sulfate, filtered and concentrated to a yellow nitrile residue (Intermediate 5, 1-(naphthalen-1-ylmethyl)-4-(phenylamino)piperidine-4-carbonitrile) which was used in the next step directly without further purification.

Figure 7:
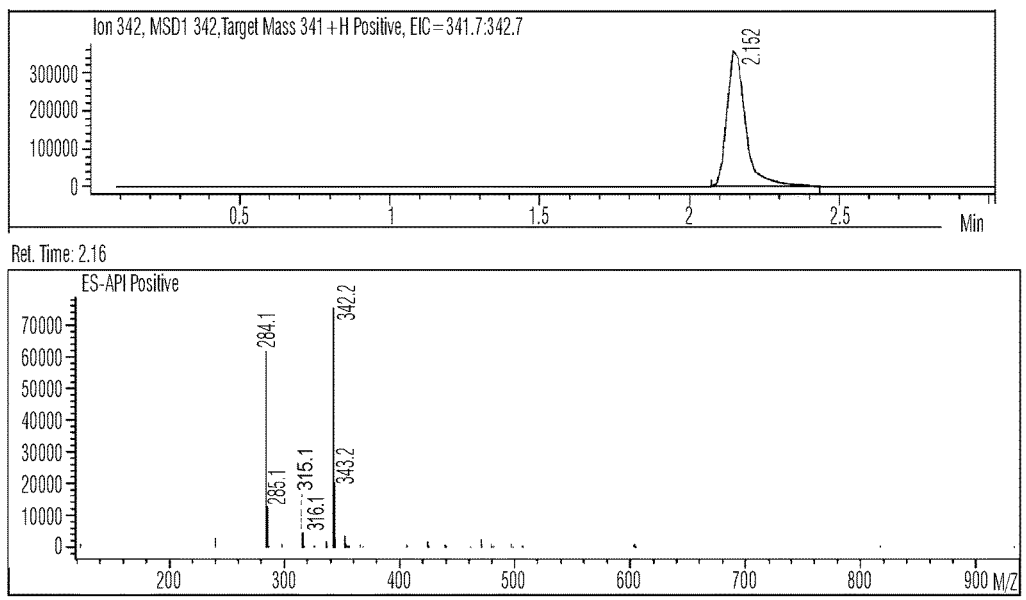
FIG. 7 demonstrates a representative chromatogram and respective mass spectrum of the peak of interest relating to Intermediate 5.

The product (Intermediate 5) was analyzed using LC-MS method as described above with ramping over 1.6 minutes and elution for 1.4 minute, with detection at +341. The chromatogram is represented in FIG. 7.

Step 4

The nitrile (Intermediate 5) was hydrolyzed according to the scheme below:

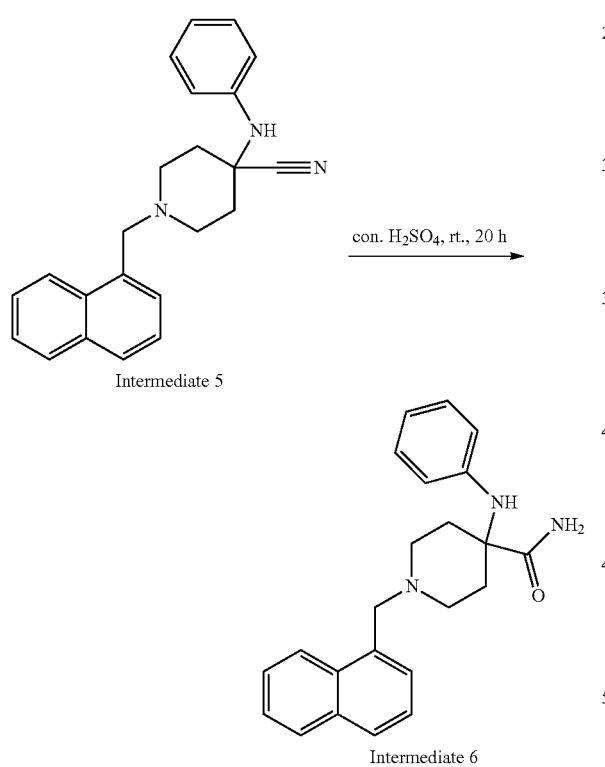

Intermediate 5 (the product of step 3) was mixed with 10 mL of concentrated sulfuric acid ($H_2SO_4$). The mixture was stirred at room temperature overnight. A concentrated ammonium hydroxide solution was slowly added until pH rose to 10. The final mixture was concentrated and purified by reverse phase preparative HPLC to provide the amide (Intermediate 6, 1-(naphthalen-1-ylmethyl)-4-(phenylamino)piperidine-4-carboxamide) as white solid (400 mg, 11% yield for the steps 2-4).

Figure 8:
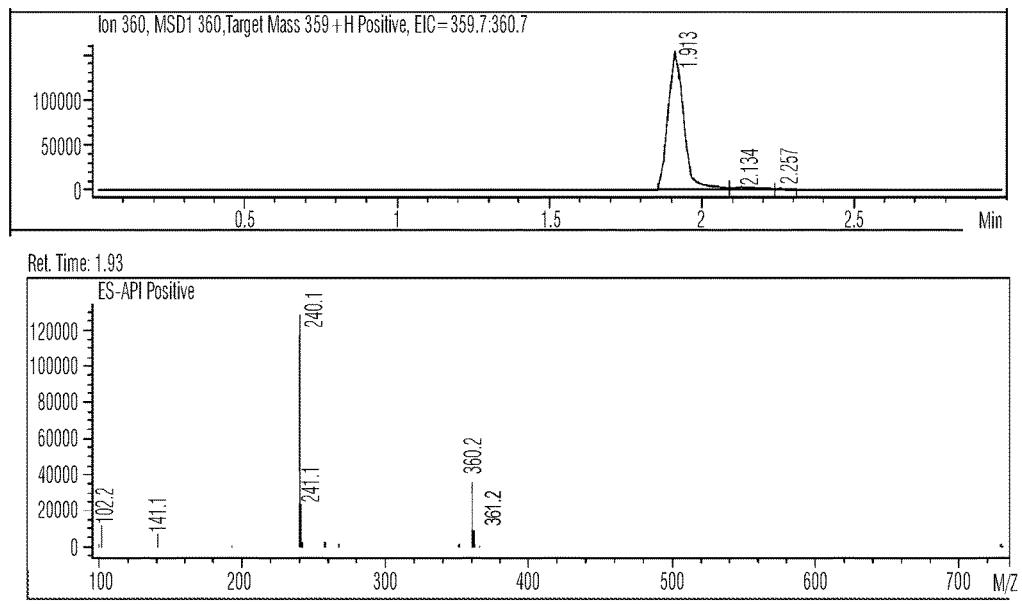
FIG. 8 demonstrates a representative chromatogram and respective mass spectrum of the peak of interest relating to Intermediate 6.

The product (Intermediate 6) was analyzed using LC-MS method as described above with ramping over 1.6 minutes and elution for 1.4 minute, with detection at +359. The chromatogram is represented in FIG. 8.

Step 5

Intermediate 6 was further hydrolyzed to carboxylic acid according to the scheme below:

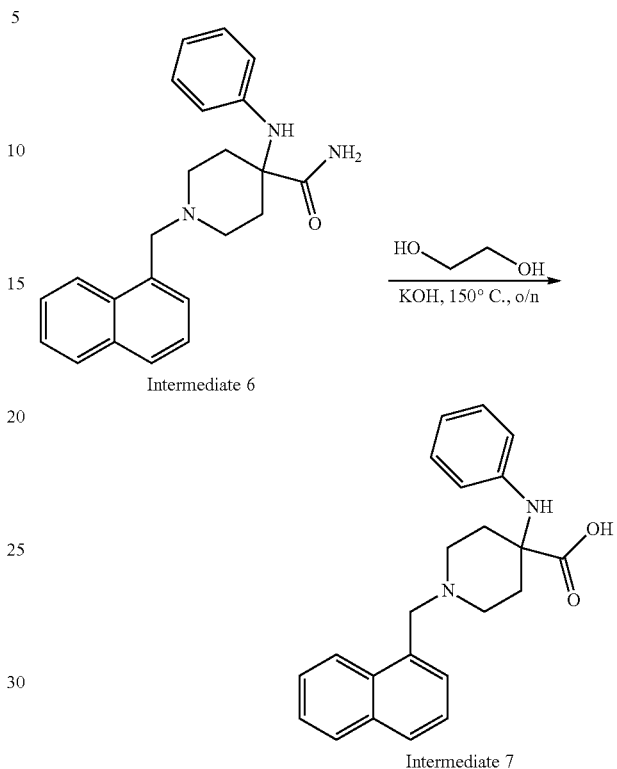

Intermediate 6 (360 mg, 1.0 mmol) was dissolved in ethylene glycol (10 mL), and potassium hydroxide (KOH) (280 mg, 5 mmol) was added. The resulting mixture was heated to 150° C. and stirred overnight. After cooling to room temperature, the final mixture was concentrated in vacuo and purified by reverse phase preparative HPLC to provide the free carboxylic acid (Intermediate 7, 1-(naphthalen-1-ylmethyl)-4-(phenylamino)-piperidine-4-carboxylic acid) as white solid (200 mg, 50% yield).

Figure 9:
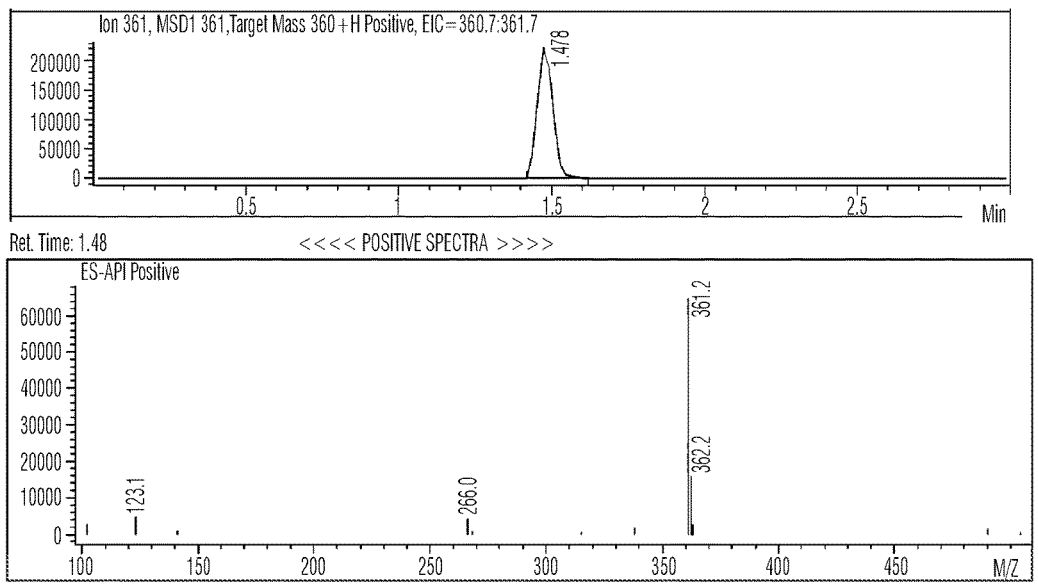
FIG. 9 demonstrates a representative chromatogram and respective mass spectrum of the peak of interest relating to Intermediate 7.

The product (Intermediate 7) was analyzed using LC-MS method as described above with ramping over 1.6 minutes and elution for 1.4 minute, with detection at +360. The chromatogram is represented in FIG. 9.

Step 6

Intermediate 7 was glycinated with methyl 2-aminoacetate (methyl glycinate) according to the scheme below:

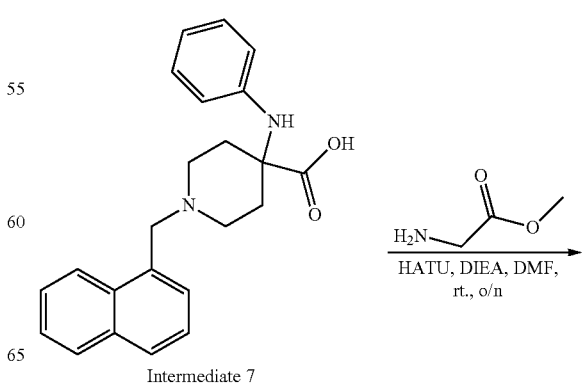

-continued

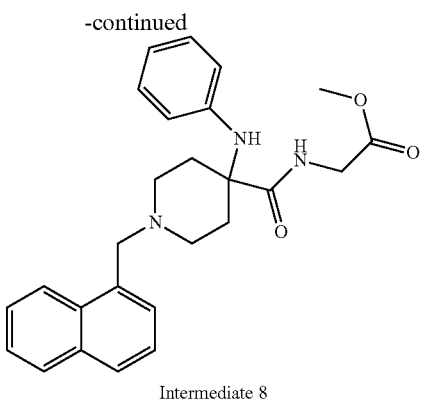

Intermediate 8

Intermediate 7 (180 mg, 0.5 mmol), HATU (1-[Bis(dimethylamino)methylene]-1H-1,2,3-triazolo-[4,5-b]-pyridinium 3-oxid hexafluorophosphate) (380 mg, 1.0 mmol), N,N-diisopropylethylamine (DIEA) (260 mg, 2.0 mmol), and methyl glycinate (90 mg, 1.0 mmol) were dissolved in dimethyl formamide (DMF) (10 mL), and the solution was stirred at room temperature overnight. The resulting mixture was concentrated in vacuo and purified by reverse phase preparative HPLC to provide the glycinate methyl ester (Intermediate 8, methyl (1-(naphthalen-1-ylmethyl)-4-(phenylamino)piperidine-4-carbonyl)glycinate) as white solid (100 mg, 46% yield).

Figure 10:
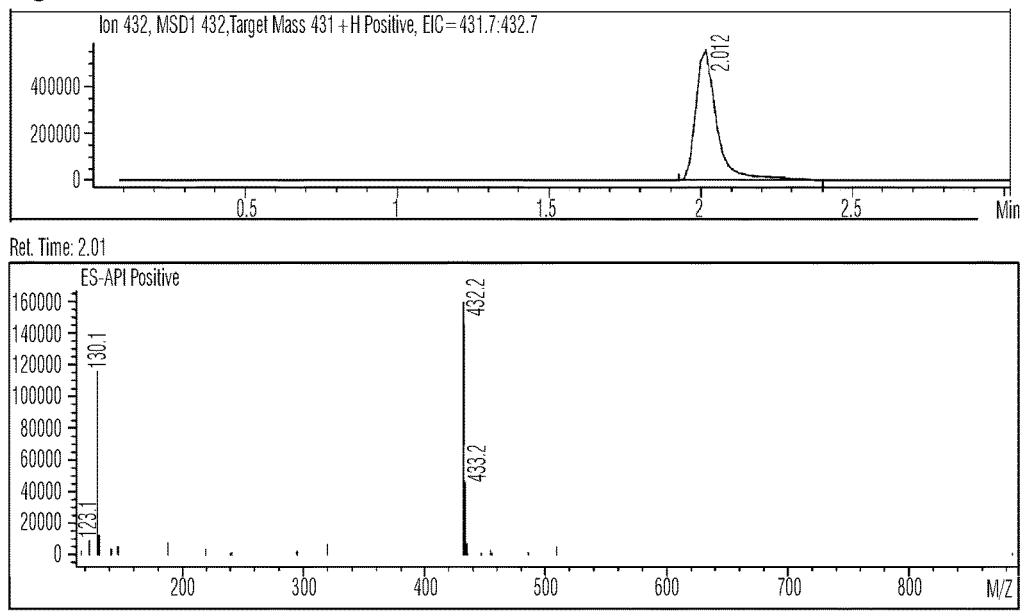
FIG. 10 demonstrates a representative chromatogram and respective mass spectrum of the peak of interest relating to Intermediate 8.

The product (Intermediate 8) was analyzed using LC-MS method as described above with ramping over 1.6 minutes and elution for 1.4 minute, with detection at +431. The chromatogram is represented in FIG. 10.

Step 7

Intermediate 8 (the glycinate methyl ester product of Step 6) was hydrolyzed with lithium hydroxide in tetrahydrofuran, according to the scheme below:

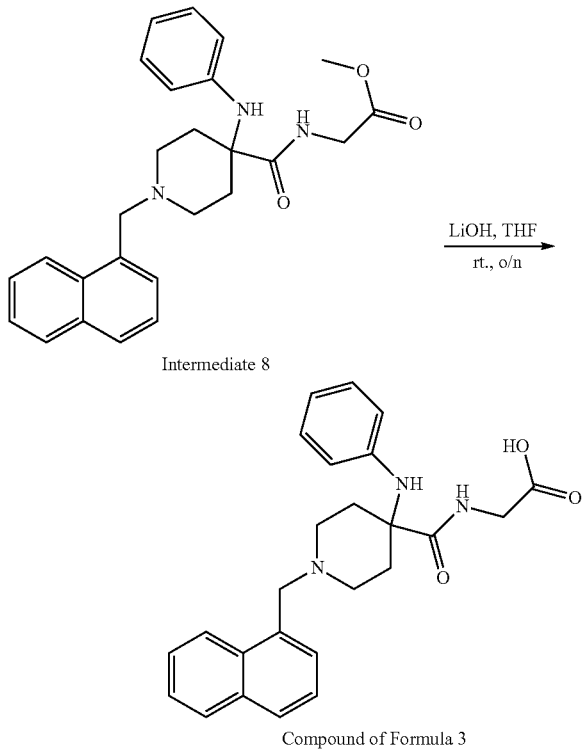

To a solution of Intermediate 8 (100 mg, 0.23 mmol) in 5 mL of THF, a solution of lithium hydroxide (LiOH) (40 mg, 1.0 mmol) in 5 mL of water was added, the resulting mixture was stirred at room temperature overnight. Thereafter, the pH was adjusted to about 7 with 1.0 N HCl. The mixture was concentrated in vacuo and purified by preparative HPLC to provide the compound of Formula 3 (VBIT-12) (20 mg, 20% yield) as white solid.

Figure 11A:
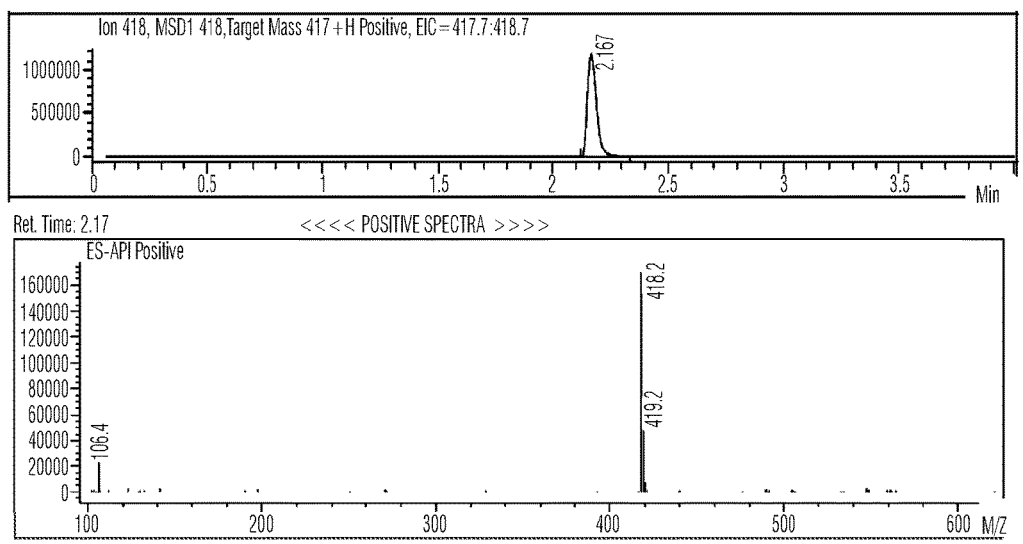
FIG. 11a demonstrates a representative chromatogram and respective mass spectrum of the peak of interest relating to the compound of Formula 3.

The product (compound of Formula 3; IUPAC name: 2-(1-(naphthalen-1-ylmethyl)-4-(phenylamino)piperidine-4-carbox-amido)acetic acid) was analyzed using LC-MS method as described above with ramping over 3 minutes and elution for 1 minute, with detection at +417. The chromatogram is represented in FIG. 11a.

The NMR spectra were obtained on 400 MHz apparatus (by Varian).

$^1$H NMR (400 MHz, DMSO/D20-d6): δ8.63 (d, H), 8.1 (s, H), 7.9 (d, J=1.2 Hz, 2H), 7.89 (d, J=2.2 Hz, 2H), 7.87 (d, J=2.3 Hz, 2H), 7.71 (dd, J=1.2 Hz, 2H), 7.67 (d, J=1.3 Hz, 2H), 7.16 (2, J=1.4 Hz, 2H), 6.78 (m, 4H), 3.80 (s, 2H), 3.71 (s, 2H), 2.31 (d, J=2.4, Hz, 2H), 2.25 (s, 2H), 2.17 (t, J=2.4, 2H), 1.98 (t, J=1.9, 2H), 1.88 (t, J=1.8, 2H)

Figure 11B:
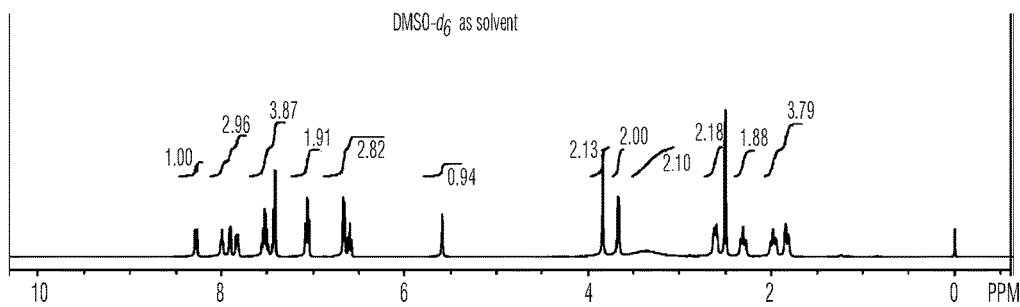
FIG. 11b demonstrates a representative NMR spectrum in deuterated DMSO relating to the compound of Formula 3.
Figure 11C:
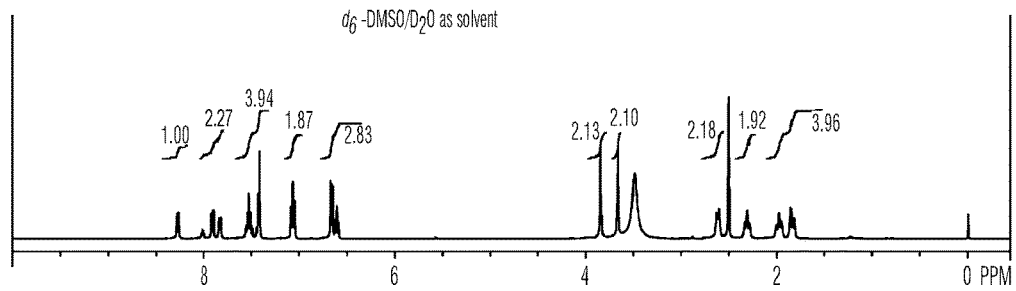
FIG. 11c demonstrates a representative NMR spectrum in deuterated DMSO and deuterated water ($D_2O$) relating to the compound of Formula 3.

The spectra in d6-DMSO and in d6-DMSO with D$_2$O are shown in the FIGS. 11b and 11c respectively.

Example 4

Chiral Separation of Compound of Formula 1 (VBIT-4) Enantiomers

Racemic compound of Formula 1 (VBIT-4) was analyzed by analytical chiral HPLC. Briefly, the material was eluted on Chiralpak-IC3 column (4.6×100 mm, 3 μm), kept at 35° C., at 2 mL/min, with acetonitrile and 20% of 0.1% solution of DEA in methanol. Two peaks, with 0.38 min difference in retention time (2.32 and 2.7 min), were obtained in expected ratio as about 50.0%. Preparative chiral HPLC was then conducted. Each peak was collected separately. The enantiomers were analyzed by 400 MHz NMR but were not discernable in deuterated DMSO.

$^1$H NMR (400 MHz, DMSO-d$_6$): δ10.081 (s, H), 7.601 (d, J=0.5 Hz, 2H), 7.341 (d, J=1.2 Hz, 2H), 7.177 (d, J=2.2 Hz, 2H), 6.980 (d, J=2.3 Hz, 2H), 4.538 (dd, J=1.2 Hz, 1H), 3.561 (m, J=1.3 Hz, H), 3.440 (m, J=1.4 Hz, H), 3.112 (m, J=1.2 Hz, 5H), 2.807 (m, J=1.6 Hz, 2H), 2.709 (m, J=1.5, Hz, 2H), 2.400 (m, J=1.4, Hz, H), 2.150 (m, J=1.4, Hz, H).

Figure 12A:
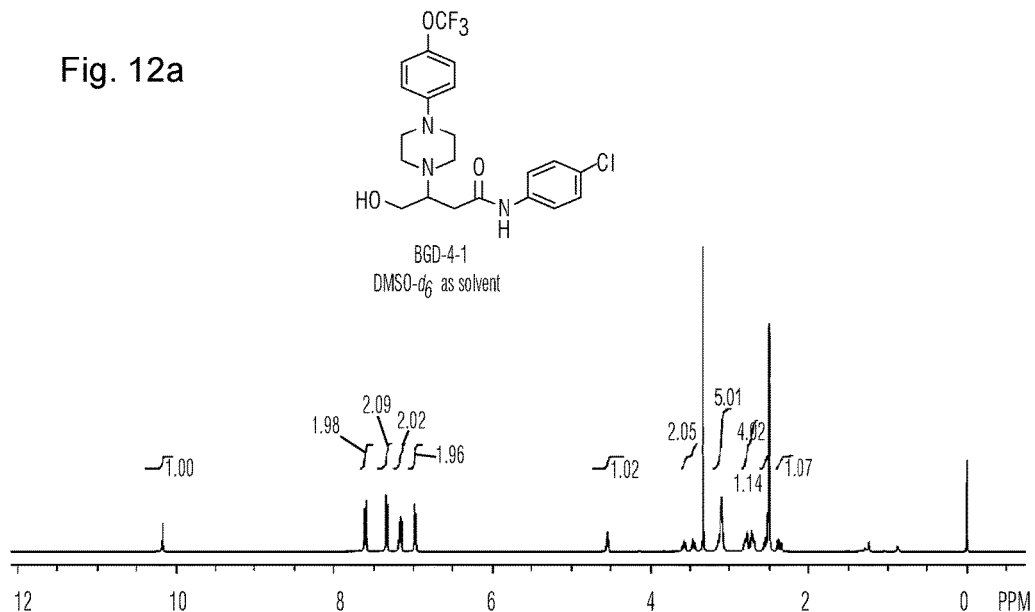
FIGS. 12a and 12b demonstrate representative NMR spectra in deuterated DMSO relating to separated single enantiomers of the compound of Formula 1 (identified as BGD-4-1 and VBIT-4-2, respectively).
Figure 12B:
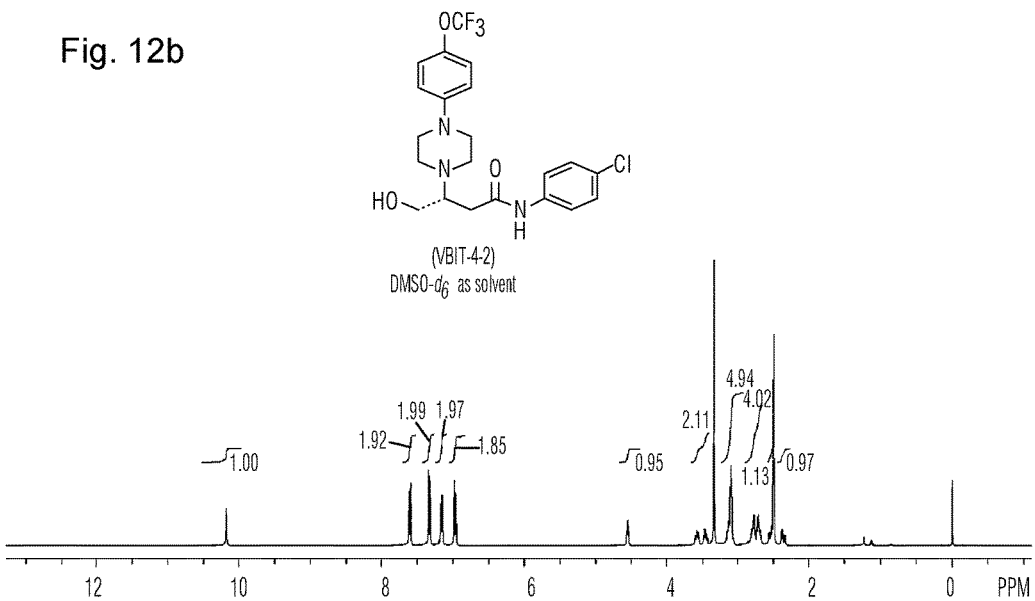

FIG. 12a demonstrates a representative NMR spectrum in deuterated DMSO relating to the separated single enantiomer of the compound of Formula 1, VBIT-4-1 (also referred to as BGD-4-1). FIG. 12b demonstrates a representative NMR spectrum in deuterated DMSO relating to the separated single enantiomer of the compound of Formula 1, VBIT-4-2 (also referred to as BGD-4-2).

Example 5

Bioluminescence Resonance Energy Transfer (BRET-2) Assay for Monitoring Oligomerization of VDAC1 in Living Cells Plasmids encoding the fusion proteins rat(r)VDAC1-GFP2 and rVDAC1-luc were constructed using the BRET2 plasmids (Perkin Elmer, Waltham, Mass.). The rVDAC1 gene was cloned into BamHI and HindIII sites of the BRET2 plasmids (N2 variants) and amplified using the forward primer CGAAGCTTATGGCTGTGCCACCCACGTAT-GCC and the reverse primer GGATCCGCCGCCGCCG- GAGCCGCCGCCGCCTGCTTGAAAT-TC. The reverse primer was designed to contain a double linker sequence ((GGGS)$_2$) connecting VDAC1 and the RLuc or GFP$_2$ genes that introduces flexibility to the region.

A plasmid encoding shRNA against human VDAC1 (hV-DAC1) for specific silencing of endogenous human VDAC1 was introduced into a shRNA-expressing vector. The hVDAC1-shRNA-encoding sequence was created using the two complimentary oligonucleotide sequences, each containing the 19 nucleotide target sequence of hVDAC1 (337-355), followed by a short spacer and an anti-sense sequence of the target:

oligonucleotide 1,

```
AGCTTAAAAACACTAGGCACCGAGATTATCTCTTGAATAATCTCGGTGC
CTAGTGTG
``` and oligonucleotide 2,

```
GATCCACACTAGGCACCGAGATTATTCAAGAGATAATCTCGGTGCCTAG
TGTTTTTTA,
``` with the VDAC1-derived sequence being underlined. The hVDAC1-shRNA-encoding sequence was cloned into the BglII and HindIII sites of the pSUPERretro plasmid (OligoEngine, Seattle, Wash.), containing a puromycin-resistance gene. Transcription of this sequence under the control of the H1 RNA promoter of RNA Polymerase III produces a hairpin (hVDAC1-shRNA).

T-REx-293 cells stably expressing hVDAC1-shRNA, showing low (10 to 20%) endogenous VDAC1 expression (referred to as T-REx-pS10 cells) were seeded onto 96-well plates at density 9,000 cells per well and incubated for at least 24 hours until attached.

The cells were transfected using calcium phosphate method. Transfections were carried out with 0.2 μg of a plasmid coding for rVDAC1-Rluc and with 0.8 μg of a plasmid coding for rVDAC1-GFP2. As a negative control, cells were transfected with plasmids encoding for rVDAC1-Rluc (0.2 μg DNA) and GFP2 (0.8 μg). In another control (control cells), cells were also transfected with a plasmid encoding for rVDAC1-luc (0.2 μg) and plasmid pcDNA4/TO (0.8 μg).

The BRET2 signal represents the ratio of the GFP2 fluorescence, measured at its emission wavelength (510 nm), over the light intensity (luminescence) emitted at 395 nm. All measurements were performed using the Infinite 200 ELISA reader (Tecan). BRET2 signals were defined as GFP2/Rluc intensity ratio and calculated as follows:

(a) The BRET2 signals obtained in VDAC1-RLuc/pcDNA4/TO cells (control cells) were subtracted from the signals obtained in cells expressing VDAC1-Rluc and VDAC1-GFP2.

(b) The net ratios of *Renilla* luciferase and GFP2 activities (GFP2/luciferase ratio after the subtraction of the BRET2 signals from control cells) were calculated.

(c) The ratios of BRET2 signals between different cells exposed and not exposed to apoptosis inducers were compared.

(d) For validation of BRET2 assay robustness, VDAC1 oligomerization was induced by the apoptosis inducer STS (Starosporine). The Z-factor and the Z'-factor, which is a measure of assay robustness, were calculated as follows:

$$Z=[BRET2\ Ratio(AVG+STS)-(AVG-STS)]/SD(+STS).$$

A Z factor >3 is considered good, the calculated Z value of about 28 was obtained.

$$Z'=1-[3\times SD(+STS)+3\times SD(-STS)]/[AVG(+STS)-AVG(-STS)]$$

A value of 0.58 for Z' factor was obtained, which is in the required range of 0.5-1; wherein
SD indicates standard deviation and AVG=average of BRET2 signal of several samples (repeats 10-36).

Alternatively, the Z-factor was calculated using the equation:

$$Z=[BRET2\ Ratio(AVG+STS)-(AVG-STS)]/SD(+STS),\ where\ a\ Z\ factor>3\ is\ considered\ good.$$

As a measure of the assay robustness, the Z' factor was obtained using the equation: $Z'=1-[3\times SD(+STS)+3\times SD(-STS)]/[AVG(+STS)-AVG(-STS)]$.

a) A value of 0.58 for Z' factor, which is in the required range of 0.5-1 for cell-based assay.

DNA encoding fusion proteins rVDAC1-Rluc (in which RLuc was connected to rVDAC1 at the C terminal position through a linker (GGGS)) and rVDAC1-GFP2 (in which the GFP2 was fused to the rVDAC1 C terminus) was cloned into BRET2 vectors. rVDAC1-GFP2 and rVDAC1-Rluc were expressed in T-REx-293 cells stably expressing shRNA-hVDAC1 and a low level of endogenous hVDAC1 (referred to as T-REx-pS10 cells) hVDAC1-shRNA, being specific to human VDAC1, allowed the expression of rVDAC1 and decreased the participation of endogenous hVDAC1 in oligomerization, thereby enhancing the BRET2 signal. rVDAC1-GFP2 and rVDAC1-Rluc expression levels were correlated with the amount of plasmids used. Specifically, 0.8 μg rVDAC1-GFP2 and 0.1 μg rVDAC1-Rluc were found to give the best signal.

The present inventors have recently demonstrated that selenite induces apoptosis and VDAC1 oligomerization. Therefore selenite was used to enhance BRET-2-detectable VDAC1 oligomerization. Conversely, 4,4-diisothiocyanostilbene-trans-2,2-disulfonic acid (DNDS), an inhibitor of VDAC1 channel conductance and apoptosis (Ben-Hail D, Shoshan-Barmatz V.VDAC1-interacting anion transport inhibitors inhibit VDAC1 oligomerization and apoptosis. Biochim Biophys Acta. 2016 July; 1863(7 Pt A):1612-2) was used to inhibit any selenite-induced BRET2 signal. Chemical cross-linking and Western blot analysis also served to demonstrate any enhancement or inhibition of VDAC1 oligomerization.

T-REx-293 cells were treated as follows: first the cells were incubated for 1 hour without or with DNDS at final concentration 200 μM in 100 μL, and then incubated with selenite, at concentration 30 μM, for additional 3 hours.

Following incubation, cells were harvested using trypsin, washed twice with PBS by centrifugation at 1000×g, 5 min, resuspended in 200 μl of PBS and divided between two wells of a 96-well clear-bottom plate (Grenier). Luciferase activity was assayed using the membrane-permeable substrate DBC in PBS supplemented with magnesium chloride (1 g/L) and glucose (1 g/L), with DBC being added to a final concentration of 5 μM just before luminescence was measured.

Figure 13A:
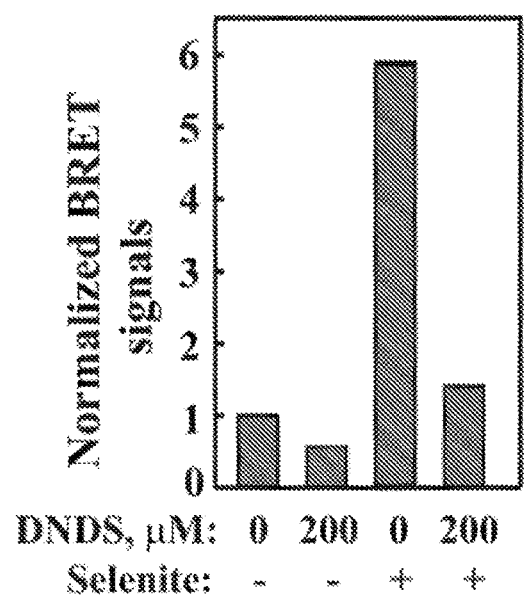
FIG. 13a demonstrates the BRET2 signals in VDAC1 dimerization experiment with or without the VDAC1 dimerization inhibitor DNDS ((Ben-Hail D, Shoshan-Barmatz V.VAC1-interacting anion transport inhibitors inhibit VDAC1 oligomerization and apoptosis. Biochim Biophys Acta. 2016 July; 1863(7 Pt A):1612-2), in absense or presence of selenite.

The results are shown in the FIG. 13a.

Example 6

Identification of VDAC1 Oligomerization Inhibitors

The ability of the compounds of the invention to inhibit VDAC1 oligomerization was tested by the following methods A and B:

Method A—VDAC1 Oligomerization Induced by Apoptosis-Inducing Reagents—the BRET2 Assay The screening was conducted using BRET2 assay as described above. Briefly, T-Rex-293 cells containing low VDAC1 levels, cultured as described above, were transfected to express rVDAC1-GFP2 (0.8 µg) and rVDAC1-Rluc (0.1 µg) and seeded at a density of 9,000 cells/well in a 96-well plate. Test compounds were diluted with DMSO to a concentration of 2 mM of the tested compound and stored frozen. Test compounds (1 µl of 2 mM stock solutions) were added (using a robotic system) to the cells to a final concentration of 10 µM in 100 µl (1% final DMSO concentration). The cells were pre-incubated for 1 hour with the tested compounds, and then incubated with one of the following apoptosis inducers: STS, 1 µM (3 h) or selenite, 30 µM (3 h) or $As_2O_3$, 60 µM (3h)—all in growth medium. After treatment, the medium was removed and assayed for BRET2 signals as described above. Liquid handling was done with the Tecan (Mannedorf, Switzerland) Freedom 150 Robotic & MCA Liquid Handling System, while luciferase luminescence and fluorescence readings were obtained a robot-integrated Tecan Infinite M1000 reader.

Method A was used for screening of VDAC1 oligomerization inhibitors. For example, drug-like compounds library provided by the National Cancer Institute (NCI) was tested using this method and the results, presented as the % of inhibition of the BRET2 signal, are shown in the Table 2 below.

TABLE 2

Summary of BRET2-based screen results of the anti-VDAC1 oligomerization activity of compounds from the NCI library
BRET2, % of inhibition

| # | NSC | $As_2O_3$ | Selenite | STS |
|---|---|---|---|---|
| 1 | 16631 | 0 | 41.5 | 30.5 |
| 2 | 48422 | 0 | 38.6 | 36.8 |
| 3 | 308849 | 99.5 | 0 | 0 |
| 4 | 42537 | 84.9 | 0 | 0 |
| 5 | 324623 | 78 | 16.3 | 0 |
| 6 | 667251 | 77.5 | 0 | 1.4 |
| 7 | 109292 | 75.4 | 0 | 0 |
| 8 | 31069 | 74.9 | 0 | 0 |
| 9 | 13151 | 67 | 0 | 0 |
| 10 | 163802 | 65.8 | 1.2 | 0 |
| 11 | 605333 | 63.7 | 16 | 0 |
| 12 | 30205 | 62.7 | 0 | 0 |
| 13 | 205968 | 58.5 | 0 | 0 |
| 14 | 32892 | 55.4 | 16.4 | 0 |
| 15 | 10768 | 52 | 9.6 | 0 |
| 16 | 31698 | 51.3 | 2.1 | 0 |
| 17 | 36586 | 49 | 0 | 0 |
| 18 | 41066 | 48.8 | 0 | 0 |
| 19 | 39938 | 48.7 | 18.8 | 0 |
| 20 | 151252 | 100 | 29.8 | 0 |
| 21 | 146554 | 100 | 71.8 | 0 |
| 22 | 23247 | 97.3 | 52.1 | 0 |
| 23 | 11150 | 95.2 | 67 | 11.6 |
| 24 | 204232 | 90.3 | 32.5 | 0 |
| 25 | 135618 | 88.9 | 64.9 | 0 |
| 26 | 657149 | 88.3 | 25.3 | 0 |
| 27 | 20045 | 88 | 77.4 | 0 |
| 28 | 268487 | 86.7 | 69.4 | 0 |
| 29 | 522131 | 86.8 | 47.6 | 0 |
| 30 | 191029 | 86.5 | 36.4 | 0 |
| 31 | 331208 | 86.4 | 28.3 | 0 |
| 32 | 28837 | 85.2 | 48.3 | 0.3 |
| 33 | 329249 | 82.8 | 22.4 | 12.1 |
| 34 | 12262 | 81.5 | 67.4 | 0 |
| 35 | 67436 | 78.1 | 65.7 | 14.8 |
| 36 | 372767 | 77.3 | 26.6 | 0 |
| 37 | 335048 | 76.5 | 35 | 17 |
| 38 | 19637 | 76.2 | 61.8 | 0 |

TABLE 2-continued

Summary of BRET2-based screen results of the anti-VDAC1 oligomerization activity of compounds from the NCI library
BRET2, % of inhibition

| # | NSC | $As_2O_3$ | Selenite | STS |
|---|---|---|---|---|
| 39 | 404057 | 74.6 | 37.1 | 0 |
| 40 | 15571 | 72.3 | 77.5 | 1.3 |
| 41 | 672441 | 69.6 | 41.8 | 0 |
| 42 | 40275 | 64.8 | 35.2 | 16.8 |
| 43 | 41377 | 60.4 | 27.3 | 0 |
| 44 | 31703 | 56.7 | 33.3 | 16.6 |
| 45 | 132868 | 55.5 | 41.4 | 0 |
| 46 | 341956 | 51.5 | 24 | 0 |
| 47 | 8816 | 49.6 | 20.1 | 0 |
| 48 | 31672 | 46.4 | 32.3 | 17.3 |
| 49 | 317605 | 46 | 52 | 0.3 |
| 50 | 338042 | 44.7 | 80.2 | 0 |
| 51 | 343966 | 39.4 | 20.1 | 0 |
| 52 | 15362 | 98 | 41 | 39.7 |
| 53 | 601359 | 97.7 | 74.4 | 46 |
| 54 | 42199 | 97 | 78.7 | 31 |
| 55 | 10428 | 96.4 | 75.7 | 38.2 |
| 56 | 154389 | 90.6 | 90.6 | 45.9 |
| 57 | 19487 | 88.8 | 68.6 | 32.6 |
| 58 | 680515 | 87.8 | 66.3 | 33.4 |
| 59 | 15364 | 85.4 | 75.9 | 40.9 |
| 60 | 146771 | 70.7 | 68.1 | 41.2 |
| 61 | 39047 | 70.2 | 54 | 39.1 |
| 62 | 36815 | 67.7 | 50 | 34.5 |
| 63 | 19115 | 64.2 | 62 | 36.4 |
| 64 | 319990 | 96.2 | 43.2 | 22 |
| 65 | 43678 | 95.1 | 78.3 | 34.6 |
| 66 | 252172 | 83.1 | 50 | 44.1 |
| 67 | 103520 | 82.5 | 74 | 22.7 |
| 68 | 43344 | 80.7 | 50.1 | 23.8 |
| 69 | 372275 | 72.5 | 46.5 | 28.5 |
| 70 | 41376 | 71.6 | 41.8 | 29.7 |
| 71 | 321502 | 67.3 | 46.5 | 22.4 |

Table 2 provides a summary of BRET2-based screen results of the anti-VDAC1 oligomerization activity of compounds from the NCI library. Results are presented as percent inhibition of the BRET2 signal induced by the indicated pro-apoptotic agent. The twelve most active compounds from the NCI library, with the three inducers, as identified by this test, were compounds number: 15362, 601359, 42199, 10428, 154389, 19487, 680515, 15364, 146771, 39047 and 19115.

Method B—VDAC1 Oligomerization Assayed by Chemical Cross-Linking

Figure 13B:
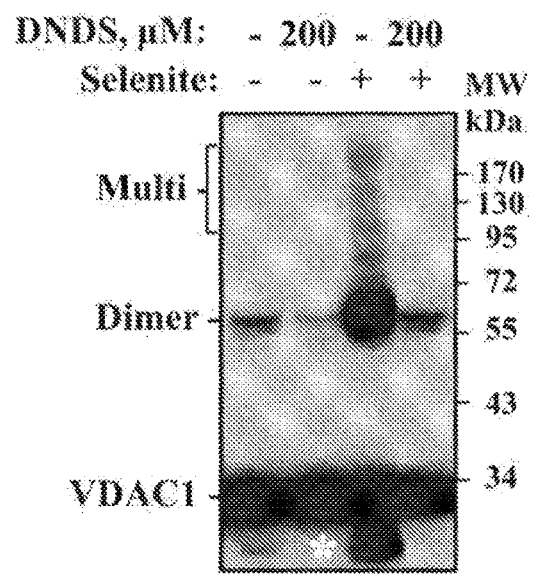
FIG. 13b demonstrates a representative VDAC1 immunoblot of electroblotted gel in VDAC1 oligomerization experiment with or without the VDAC1 dimerization inhibitor DNDS ((Ben-Hail D, Shoshan-Barmatz V.VDAC1-interacting anion transport inhibitors inhibit VDAC1 oligomerization and apoptosis. Biochim Biophys Acta. 2016 July; 1863(7 Pt A):1612-2), in absense or presence of selenite. VDAC oligomers were stabilized by EGS cross-linking.

T-Rex-293 cells were treated as described in Example 5 hereinabove, and cross-linked with EGS as described above in Methods (VDAC1 cross-linking), subjected to SDS-electrophoresis and immunoblotted for VDAC1. The results are shown in the FIG. 13b.

The present inventors have previously reported the equivalence of the method A and B for apoptosis inhibitor 4,4'-dinitrostilbene-2,2'-disulfonic acid (DNDS) (Ben-Hail D, Shoshan-Barmatz V. VDAC1-interacting anion transport inhibitors inhibit VDAC1 oligomerization and apoptosis. Biochim Biophys Acta. 2016 1863 (2016) 1612-1623).

The ability of the compounds of the invention to inhibit VDAC1 oligomerization was tested by Method B and the results are provided in Examples 8-12 hereinafter.

Example 8

VDAC1 Oligomerization Inhibition by Racemic VBIT-4 and Enantiomers

HEK-293 cells were incubated with racemic compound of Formula 1 (VBIT-4), enantiomer 1 of compound of Formula 1 (VBIT-4-1 (also identified as BGD-4-1)) or enantiomer 2 of compound of Formula 1 (VBIT-4-2 (also identified as BGD-4-2)) (10 μM) for 2 h and then with or without selenite (15 μM, 4 h). The cells were harvested, cross-linked with EGS (300 μM, 15 min) as described above, and analyzed by immunoblot using anti-VDAC1 antibodies.

Figure 14A:
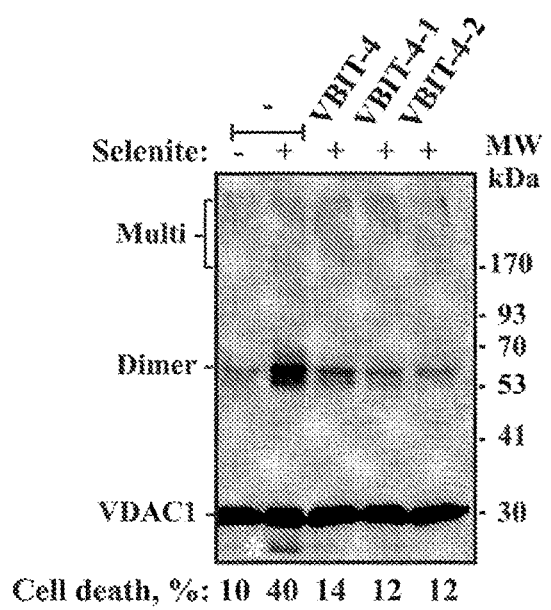
FIG. 14a demonstrates a representative VDAC1 immunoblotted electroblotted gel of VDAC1 oligomerization experiment with or without the single enantiomers or the racemic compound of Formula 1, in presence of selenite. VDAC1 oligomers were stabilized by EGS cross-linking.

The results are presented in the FIG. 14a. The positions of VDAC1 monomers and multimers are indicated. The star indicates monomeric VDAC1 with modified electrophoretic mobility, representing intra-molecular crossed-linked monomeric VDAC1.

Example 9

Figure 14B:
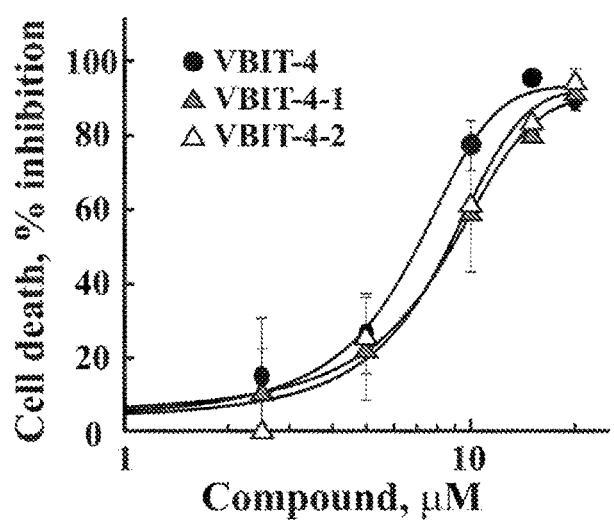
FIG. 14b schematically demonstrates an apoptotic cell death inhibition as function of concentration of the single enantiomers or the racemic compound of Formula 1 in presence of selenite.

Racemic Compound of Formula 1 (VBIT-4) and Enantiomers of Compound of Formula 1 (VBIT-4-1 and VBIT-4-2) Inhibit Apoptotic Cell Death HeLa cells were incubated with varying concentrations (2-20 μM) of racemic compound of Formula 1 (VBIT-4) and of the enantiomers of compound of Formula 1 (VBIT-4-1 and VBIT-4-2) for 1 hour, and then with or without selenite (25 μM, 3 hours). Cells were harvested and assayed for apoptotic cell death, using PI staining and FACS analysis. The results shown in the FIG. 14b correspond to means±SD (n=3).

Example 10

Figure 15A:
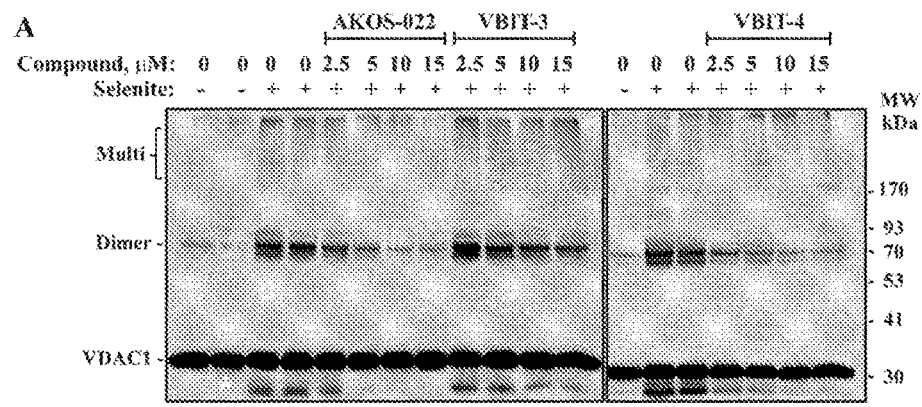
FIG. 15a demonstrates a representative VDAC1 immunostained electroblotted gel in VDAC1 oligomerization experiment with or without the racemic compound of Formula 1, and the compounds of Formulae 2 and 10, in presence of selenite.

Inhibition of VDAC1 Oligomerization, Apoptosis and Cytochrome C Release by Compound of Formula 10 (AKOS-022), Compound of Formula 2 (VBIT-3) and Racemic Compound of Formula 1 (VBIT-4), in HEK-293 Cells a. HEK-293 cells were incubated without and with the following tested compounds: compound of Formula 10 (AKOS-022), compound of Formula 2 (VBIT-3) or racemic compound of Formula 1 (VBIT-4) (2.5-15 μM) for 2 hours and then with or without selenite (15 μM, 4 h), trypsinized, washed with PBS, protein concentration was determined and harvested, cross-linked with EGS (3 mg protein/ml, 300 μM, 15 min), and analyzed by immunoblot using anti-VDAC1 antibodies. The positions of VDAC1 monomers and multimers are indicated in the FIG. 15a. The star indicates monomeric VDAC1 with modified electrophoretic mobility, representing intra-molecular crossed-linked monomeric VDAC1.

Figure 15B:
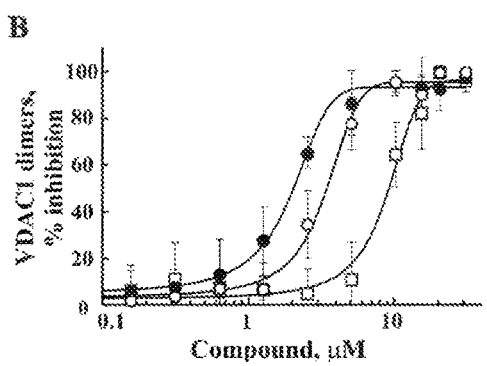
FIG. 15b demonstrates inhibition of VDAC1 oligomerization as function of concentration of the compounds of Formulae 1, 2 and 10, in presence of selenite. The closed circle (●) indicates compound of Formula 1, the open circle (○) indicates compound of Formula 10, and an open square (□) indicates compound of Formula 2.
Figure 15C:
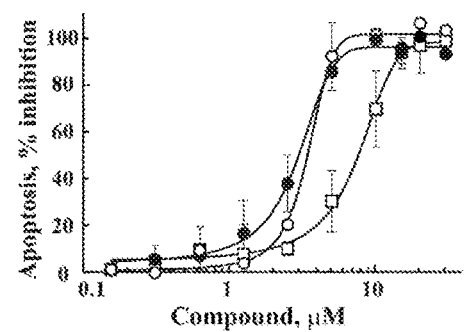
FIG. 15c schematically demonstrates inhibition of selenite-induced apoptotic cell death as function of concentration of the compounds of Formulae 1, 2 and 10. The closed circle (●) indicates compound of Formula 1, the open circle (○) indicates compound of Formula 10, and an open square (□) indicates compound of Formula 2.
Figure 15D:
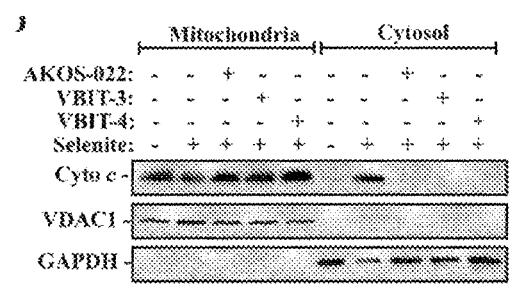
FIG. 15d demonstrates a representative VDAC1 immunostained electroblotted gel bands of Cyto c and VDAC1 in mitochondria and in cytosolic fraction after exposure to selenite and the compounds of Formulae 1, 2 and 10.
Figure 15E:
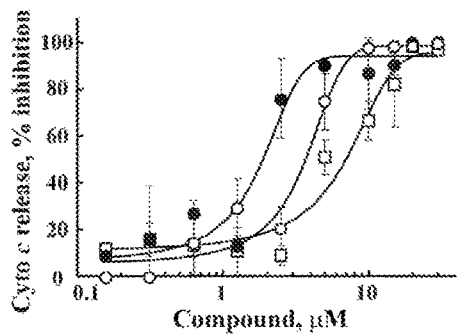
FIG. 15e demonstrates inhibition of selenite-induced Cyto C release as a function of concentration of the compounds of Formulae 1, 2 and 10. The closed circle (●) indicates compound of Formula 1, the open circle (○) indicates compound of Formula 10, and an open square (□) indicates compound of Formula 2.

Quantitative data of the selenite-induced VDAC1 dimer formation by the tested compounds is presented as inhibition percentile, in the FIG. 15b. The results show means±SD (n=3). The closed circle (●) indicates VBIT-4 (compound of Formula 1), the open circle (○) indicates compound of Formula 10, and an open square (□) indicates VBIT-3 (compound of Formula 2).

b. Additionally, the inhibition of selenite-induced apoptosis by the compounds as analyzed using annexin V-FITC/PI staining and FACS, presented in the FIG. 15c.

c. Cytochrome c (Cyto c) release was determined as described above in Methods (Cytochrome c release from mitochondria). Briefly, to assess Cyto c release, cells were incubated on ice for 10 min with 0.025% digitonin, centrifuged, and the pellet (mitochondria—Mito) and supernatants (cytosol—Cytos) were subjected to SDS-PAGE and immunoblotting, using anti-Cyto c, antibodies. Anti-VDAC1 and anti-GAPDH antibodies were used to verify that the cytosolic extracts are mitochondria-free. The results of Cyto c release from the mitochondria as induced by selenite are presented as immunoblots, with the cytosolic and mitochondrial fractions confirmed by immunoblotting of GAPDH (glyceraldehyde-3-phosphate dehydrogenase) and VDAC1, respectively, in the FIG. 15d. The quantitative data of selenite-induced Cyto c release to the cytosol by the tested compounds is presented in the FIG. 15e. The data are presented as percent inhibition. The results shown correspond to means±SD (n=3). The closed circle (●) indicates VBIT-4 (compound of Formula 1), the open circle (○) indicates compound of Formula 10 (AKOS-022), and an open square (□) indicates VBIT-3 (compound of Formula 2).

d. IC50 values of the tested compounds were derived from the obtained data. The results shown correspond to means±SD (n=3).

TABLE 3

| Compound Formula # (name) | VDAC1 oligomerization $IC_{50}$, μM | Cyto c release $IC_{50}$, μM | Apoptosis $IC_{50}$, μM |
|---|---|---|---|
| Formula 10 (AKOS 022) | 3.3 ± 0.18 | 3.6 ± 0.4 | 3.4 ± 0.2 |
| Formula 2 (VBIT-3) | 8.8 ± 0.56 | 6.6 ± 1.03 | 7.5 ± 0.27 |
| Formula 1 (VBIT-4) | 1.9 ± 008 | 1.8 ± 0.24 | 2.9 ± 0.12 |

Example 11

Inhibition of VDAC1 Oligomerization and of Apoptosis, in Neuronal Cells and in Bax/Bak-Lacking Cells, by Compound of Formula 10 (AKOS-022) and Racemic Compound of Formula 1 (VBIT-4)

SH-SY5Y cells and $Bax^{-/-}/Bak^{-/-}$ MEFs cells were incubated with the following tested compounds: compound of Formula 10 (AKOS-022) or racemic compound of Formula 1 (VBIT-4) (30 μM, 2 h), and then with or without cisplatin (20 μM, 20 h). The cells were harvested, cross-linked with EGS (200 μM, 15 min), and analyzed by immunoblot using anti-VDAC1 antibodies.

Figure 16A:
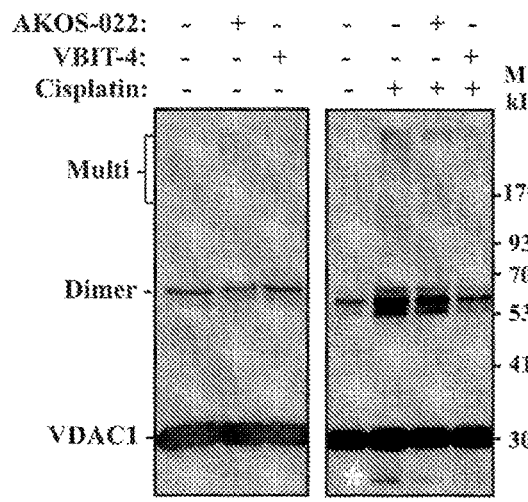
FIG. 16a demonstrates a representative immunostained electroblotted gel of VDAC1 after exposure to the compounds of Formulae 1 and 10 in absence or presence of cisplatin in SH-SY5Y cells.
Figure 16B:
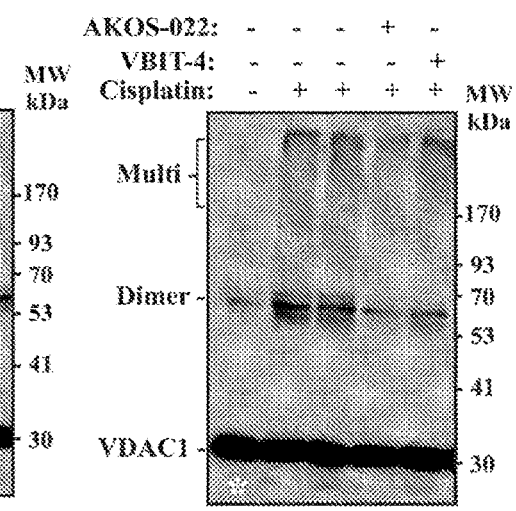
FIG. 16b demonstrates a representative immunostained electroblotted gel of VDAC1 after exposure to the compounds of Formulae 1 and 10 in presence of cisplatin in $Bax^{-/-}/Bak^{-/-}$ MEF cells.

The results from SH-SY5Y cells are presented in the FIG. 16a. The results from $Bax^{-/-}/Bak^{-/-}$ MEFs cells are presented in the FIG. 16b. The positions of VDAC1 monomers and multimers are indicated. The star indicates monomeric VDAC1 with modified electrophoretic mobility, representing intra-molecular crossed-linked monomeric VDAC1.

Figure 16C:
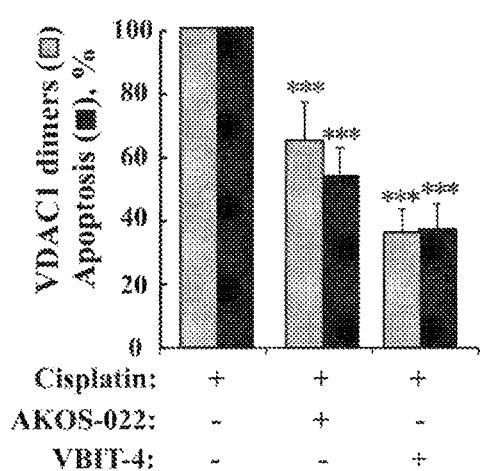
FIG. 16c demonstrates inhibition of apoptotic cell death and of VDAC1 dimers formation in the presence of the compounds of Formulae 1 and 10, in presence of cisplatin in SH-SY5Y cells.

Quantitative analysis of cisplatin-induced VDAC1 dimers formation (gray columns) and apoptosis as analyzed using annexin V-FITC/PI staining and FACS (black columns) in SH-SY5Y cells, in the absence and presence of the tested compounds, is presented in the FIG. 16c. The results shown correspond to mean±SD (n=3), $p<0.001$(***).

Figure 16D:
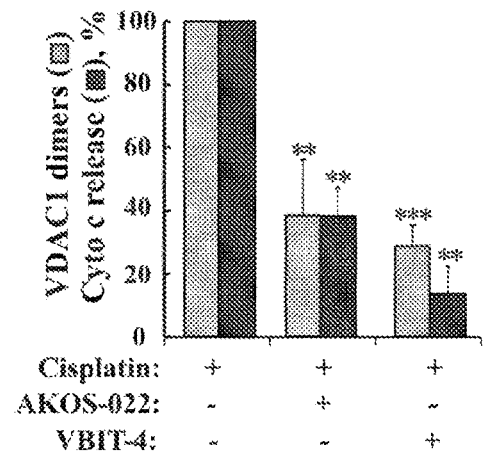
FIG. 16d demonstrates inhibition of apoptosis Cyto C release and of VDAC1 dimers formation in the presence of the compounds of Formulae 1 and 10, in presence of cisplatin in $Bax^{-/-}/Bak^{-/-}$ MEF cells.

Quantitative analysis of cisplatin-induced VDAC1 dimers formation and cytochrome c release by the tested compounds in $Bax^{-/-}/Bak^{-/-}$ MEFs cells is presented in the FIG. 16d.

Example 12

Correlation Between the Extent of Inhibition of Apoptosis and of VDAC1 Oligomerization by Compound of Formula 10 (AKOS-022)

HeLa cells were incubated with compound of Formula 10 (AKOS-022) at 0-20 μM for 2 hours and further with or without selenite (30 μM, 3 h) or cisplatin (15 μM, 20 h). Cells were harvested and either cross-linked with EGS (300 μM, 15 min) as described above, and analyzed for VDAC1 oligomerization by immunoblot using anti-VDAC1 antibodies, or assayed for apoptotic cell death using annexin V-FITC/PI staining and FACS analysis. The gel of selenite experiment is represented in the FIG. 17a.

Figure 17:
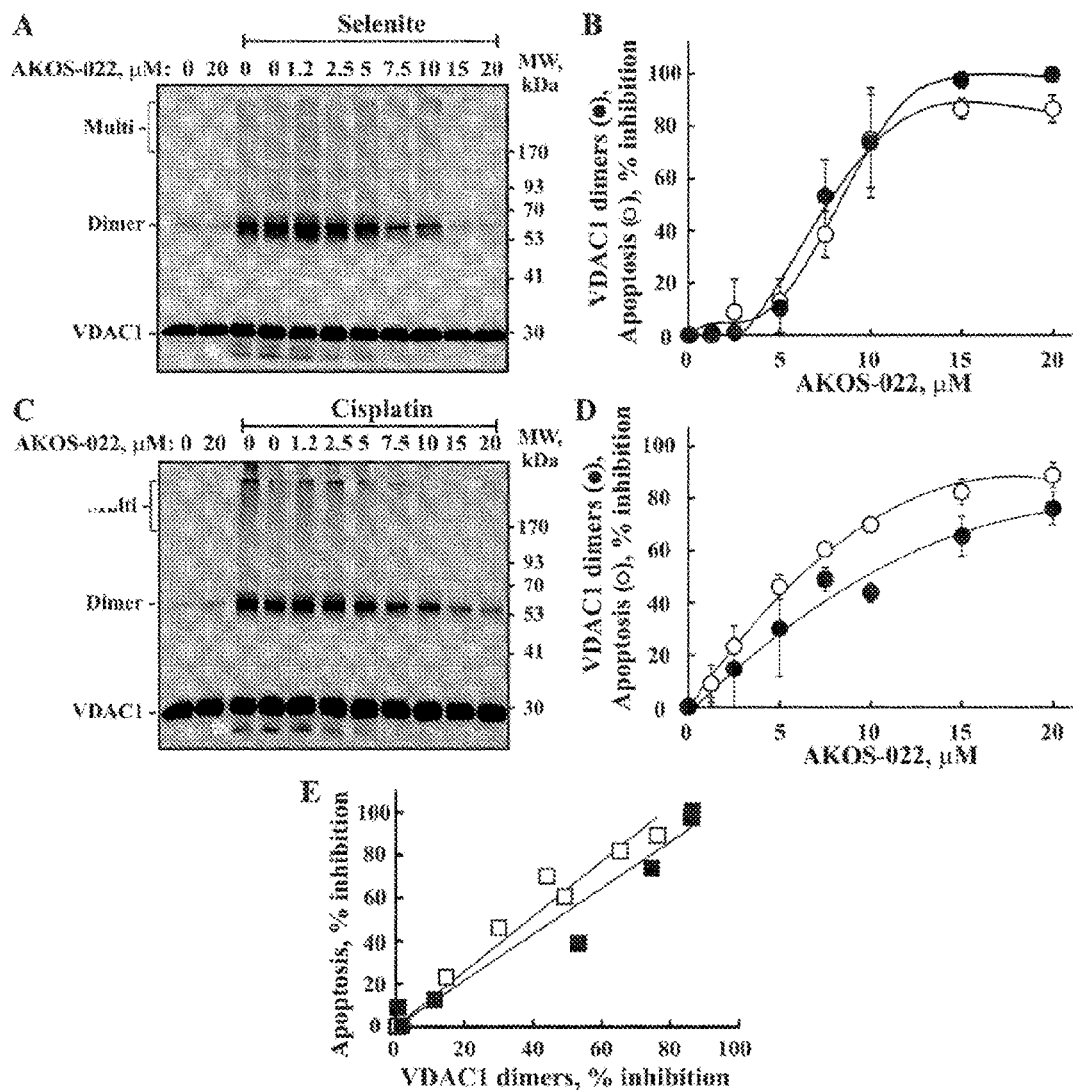
FIG. 17a demonstrates a representative VDAC1 immunostained electroblotted gel of VDAC1 after exposure to increasing concentrations of the compound of Formula 10 in presence of selenite.
FIG. 17b demonstrates inhibition of apoptosis and VDAC1 dimers formation as function of exposure to increasing concentrations of the compound of Formula 10 in presence of selenite.
FIG. 17c demonstrates a representative VDAC1 immunostained electroblotted gel of VDAC1 after exposure to increasing concentrations of the compound of Formula 10 in presence of cisplatin.
FIG. 17d demonstrates inhibition of apoptosis and VDAC1 dimers formation as function of exposure to increasing concentrations of the compound of Formula 10 in presence of cisplatin.
FIG. 17e demonstrates the extent of apoptosis inhibition as function of VDAC1 dimerization inhibition obtained at the same concentration of Formula 10 and as induced by either cisplatin (empty square—□) or selenite (solid square—■).

Quantitative analysis of the inhibition of VDAC1 dimer levels and cells undergoing apoptosis as induced by selenite, as a function of compound of Formula 10 (AKOS-022) concentration, are presented in the FIG. 17b. The results reflect means±SD (n=3).

The gel of cisplatin experiment is represented in the FIG. 17c. Quantitative analysis of the inhibition of VDAC1 dimer levels and cells undergoing apoptosis as induced by cisplatin, as a function of compound of Formula 10 (AKOS-022) concentration, are presented in the FIG. 17d. The results reflect means±SD (n=3).

Quantitative analysis of the extent of apoptosis inhibition as a function of the inhibition of VDAC1 dimer formation is presented in FIG. 17e. Apoptosis was induced either by selenite (solid square—■) or cisplatin (empty square—□), and was analyzed at the identical AKOS-022 concentration as described above.

Example 13

Interaction of Tested Compounds with Purified VDAC1 and with Lipid Bilayer-Reconstituted Purified VDAC1 and Reduced Channel Conductance VDAC1 was purified as described above in Methods (VDAC1 purification). Purified VDAC1 was reconstituted into a planar lipid bilayer (PLB) membrane and currents through VDAC1, in response to a voltage step from 0 to 10 mV, were recorded before and 30 min after the addition of 40 μM of the following test compounds: compound of Formula 10 (AKOS-022), compound of Formula 2 (VBIT-3) or racemic compound of Formula 1 (VBIT-4), as shown in the FIG. 18a.

Additionally, the channel conduction via multi-channel recordings as function of voltage, and the average steady-state conductance of VDAC1 were measured.

FIG. 18b demonstrates channel conductance before (solid squares) and 30 min after the addition of compound of Formula 10 (AKOS-022) (empty circle), of compound of Formula 2 (VBIT-3) (empty square), or of racemic compound of Formula 1 (VBIT-4) (solid circle). Relative conductance (conductance/maximal conductance) was determined at a given voltage. The data were normalized according to the conductance at −10 mV (maximal conductance).

Example 14

Binding Affinities of Tested Compounds to Purified VDAC1

Purified VDAC1 (133 nM), labeled using the NanoTemper fluorescent protein-labeling Kit BLUE (Nano Temper technologies, Munich, Germany), according to the manufactory instructions, was incubated with increasing concentrations of the following tested compounds: compound of Formula 10 (AKOS-022), compound of Formula 2 (VBIT-3), or racemic compound of Formula 1 (VBIT-4). After 20 min of incubation, the samples (3-5 μL) were loaded into MST-grade glass capillaries (Monolith NT Capillaries), and the thermophoresis process was measured using the Monolith-NT115 apparatus. The results are presented in the FIG. 18c as % of the bound fraction, of compound of Formula 10 (AKOS-022) (open circle), of compound of Formula 2 (VBIT-3) (open square), or of racemic compound of Formula 1 (VBIT-4) (closed circle) (0.3 μM to 100 μM), each with purified VDAC-1.

The fraction bound was calculated as:

$$\text{Fraction bound} = 100 \times \frac{F - Fmin}{Fmax - Fmin}$$

Fmax and Fmin represent the maximal and minimal fluorescence, respectively and F the fluorescence measured in the presence of the tested compound.

VDAC1 binding affinities of tested compounds were calculated from the MST measurements. The results of means±SD (n=3) are 15.4±2.9 μM for the compound of Formula 10 (AKOS022), 31.3±1.7 μM for the compound of Formula 2 (VBIT-3), and 17±5.3 μM for the racemic compound of Formula 1 (VBIT-4).

Example 15

Figure 19:
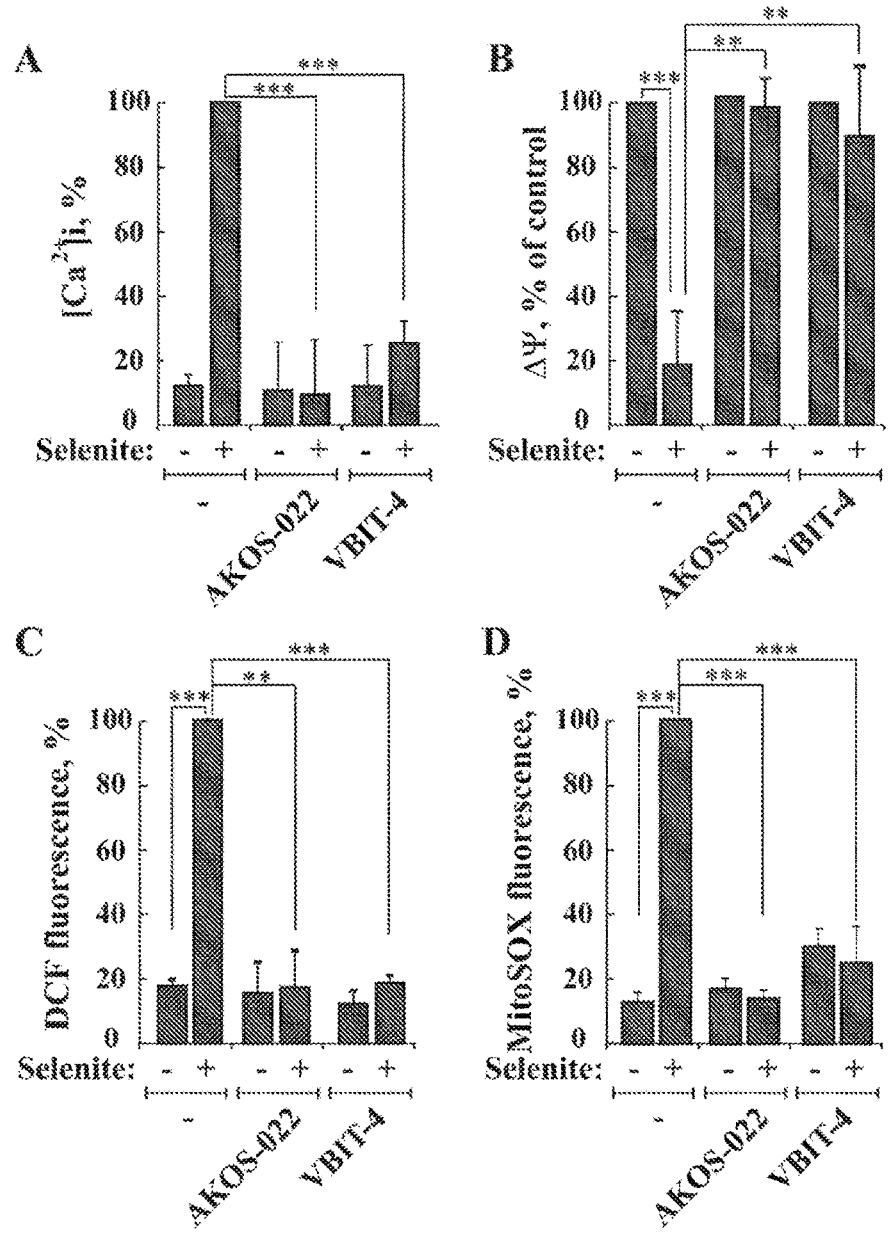
FIG. 19a demonstrates the effect of compounds of Formulae 1 and 10 on intracellular calcium ion concentrations in cells treated selenite.
FIG. 19b demonstrates the effect of compounds of Formulae 1 and 10 on mitochondrial membrane potential in cells treated selenite.
FIG. 19c demonstrates the effect of compounds of Formulae 1 and 10 on ROS levels in cells treated selenite.
FIG. 19d demonstrates schematically the effect of compounds of Formulae 1 and 10 on mitochondrial superoxide levels in cells treated selenite.

The Effect of the Tested Compounds on Selenite-Induced Increases in Intracellular Calcium Levels, Mitochondrial Membrane Potential and Reactive Oxygen Species (ROS) Levels a. HEK-293 cells were incubated with the following test compounds: compound of Formula 10 (AKOS-022), compound of Formula 2 (VBIT-3), or compound of Formula 1 (VBIT-4) (15 μM, 2 hours) and then with or without selenite (15 μM, 4 hours). The cells were harvested and intracellular calcium ($[Ca^{2+}]i$) levels were measured using Fluo-4 and FACS analysis, as described above. Quantitative analysis of the results as percentile of maximal $[Ca^{2+}]i$ is presented in the FIG. 19a.

b. Mitochondrial membrane potential ($\Delta\Psi$) was analyzed with TMRM and FACS analysis. CCCP (25 μM, 30 min) served as a positive control for mitochondrial ΔΨ dissipation and the CCCP-sensitive TMRM fluorescence. The respective results are presented in FIG. 19b.

c. Cellular ROS levels were analyzed with carboxy-H2DCFDA and FACS analysis. Mitochondrial superoxide was detected with MitoSOX Red and flow cytometry. The respective results are presented in FIGS. 19c-d.

All the results shown in FIGS. 19a-d correspond to mean±SD (n=3), $p<0.05(*)$, $<0.01 ()$ or $<0.001(*)$.

Example 16

Preparation of PLGA Nanoparticles of Compound of Formula 10

About 10 mg of AKOS-022 was dissolved in 1 mL of acetone, followed by 50 mg of PLGA. This organic phase mixture was added in a drop-wise manner (ca. 0.5 ml/min) to 20 ml of aqueous solution containing 1% polyvinyl alcohol (PVA) (w/v) as the stabilizer. The mixture was then stirred at 400 rpm by a laboratory magnetic stirrer at room temperature until complete evaporation of the organic solvent. The redundant stabilizer was removed from the nanoparticles dispersion by centrifugation at 15,000×g at 4° C. for 20 min. The pellet was re-suspended in sterile double distilled water and washed three times.

Blank nanoparticles were prepared in the same manner except AKOS-022 addition.

Example 17

Preparation of PLGA Nanoparticles of Compound of Formula 1

PLGA nanoparticles containing the compound of Formula 1 (VBIT-4) were prepared according to the Example 16, with 10 mg of VBIT-4 substituting 10 mg of AKOS022.

Example 18

Brain Penetration of and Exposure to the Compounds of Formulae 1 and 10

C57BL/6 mice (20 gm) were used. The animals received treatments with either free compounds of Formulae 1 and 10, or encapsulated compounds, prepared according to the Examples 16 and 17. Doses as indicated in the Table 4 below were administered in phosphate-buffered saline (PBS) through an oral gavage. After 12 hours and 24 hours, randomly selected mice from each group were sacrificed, their brains collected and stored in −80° C. The concentrations of the compounds in the tissues were determined by HPLC/MS analysis. Tissue samples were homogenized in phosphate-buffered saline solution, then diluted with acetonitrile to 50% v/v, centrifuged at 10,000 g for 10 minutes, and supernatants were analyzed. The compounds concentrations in the brain extracts were determined from calibration curves. The results were the averaged from 2 mice for each treatment group/time point.

TABLE 4

| Compound | Treatment | Compounds in brain extract, µM |
|---|---|---|
| Formula 10 | 50 mg/kg, 12 h | 4.2 ± 0.714 |
| Formula 10 | 50 mg/kg, 24 h | 1.24 ± 0.23 |
| Formula 10 | 50 mg/kg in PLGA, 12 h | 4.36 ± 0.148 |
| Formula 10 | 50 mg/kg in PLGA, 24 h | 2.8 ± 1.19 |
| Formula 1 | 50 mg/kg in PLGA, 24 h | 0.190 ± 0.07 |
| Formula 1 | 50 mg/kg, 24 h | 0.120 ± 0.02 |

The compounds of Formulae 1 and 10 (AKOS-022 and VBIT-4) given orally reached the brain both when giving in solution or encapsulated in PLGA nano-particles. However, while 12 hours after administration the level of AKOS-022 in the brain was similar in both cases, after 24 hours the level of AKOS022 or VBIT-4 was over 2-fold when encapsulated in PLGA. The AKOS-022 and VBIT-4 levels in the brain is in its effective range (IC50=1 µM). Thus the molecules when administrated either non- or PLGA-encapsulated can reach the brain.

Example 19

Effect of Compound of Formula 1 on Learning and Memory Task of 5XFAD Transgenic Mice with Alzheimer Disease-Like Disease Using the Radial-Arm Water Maze for Testing Learning and Memory Task The effect of the compound of Formula 1 (VBIT-4) on learning and memory task of 5XFAD transgenic mice with AD-like disease was tested as disclosed in Webster, S. J., et al, (2014) *Frontiers in genetics* 5, 88, ([5XFAD B6.Cg-Tg APPSwFlLon, PSEN1*M146Ln*L286V6799Vas/J]). These mice present detectable phenotypes of intracellular and extracellular amyloid plaques at 2 months of age, develop cognitive impairments at 4-5 months and exhibits neuronal death at 9 months.

The compound of Formula 1 (VBIT-4) was dissolved in drinking water as follows. About 24 mg of VBIT-4 were transfer to Eppendorf tube and dissolved in 120 µl of 100% DMSO by Vortex mixer. Clear solution was obtained. Solution of 1 M of HCl, about 10 mL, was prepared from 6-M HCl solution, provided by Pierce, Rockford, Ill., USA. About 370 µL of the 1M HCl solution was used to acidify 120 mL of drinking water. The VBIT-4 DMSO solution (120 µL) was slowly added (by dropping) into the acidic water and mixed by magnetic stirring. The final pH was between 4.8 and 5.0. If the solution became milky, further 10 to 30 µL of HCl solution were added to obtain clear solution. The amount was sufficient for 24 mice at dose of 20 mg/kg and drinking volume of 5 mL per mouse per day.

Animals at age two months were assigned to three groups: transgenic treated (TG-T, 8 males and 3 females), transgenic vehicle (TG-V, 8 males and 3 females), and wild type (WT, 10 males and 8 females). Of these, 2 males in TG-T group dies during the study.

Two-months old 5XFAD mice were provided with 0.9% of DMSO solution or VBIT-4 solution (20 mg/kg in 0.9% DMSO) in drinking water replaced with fresh solution three times a week in the first month and thereafter twice a week for additional 3 months.

When the mice reached the age of six months, a two-day radial-arm water maze (RAWM) trial was performed as described previously (Jennifer Alamed, et al, Nature Protocols 1, (2006) 1671-1679) to test the effect of VBIT-4 on learning and memory task. The RAWM containing six swim paths (arms) was used. The arms were extending out from an open central area with an escape platform located at the end of one arm (the goal arm). The goal arm location remained constant for a given mouse. On day 1, mice were trained for 15 trials (spaced over 3 h), with trials alternating between visible and hidden platforms. On day 2, mice were trained for 15 trials with the hidden platform.

Figure 20A:
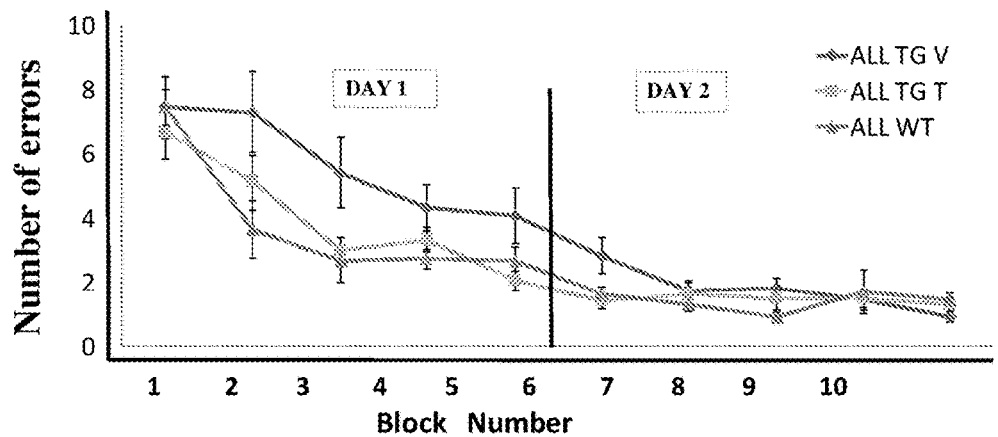
FIG. 20A demonstrates the effect of compound of Formula 1 on learning and memory of transgenic mice with Alzheimer's disease like symptoms using Radial Arm Water Maze test; number of errors is demonstrated as function of learning blocks.
Figure 20B:
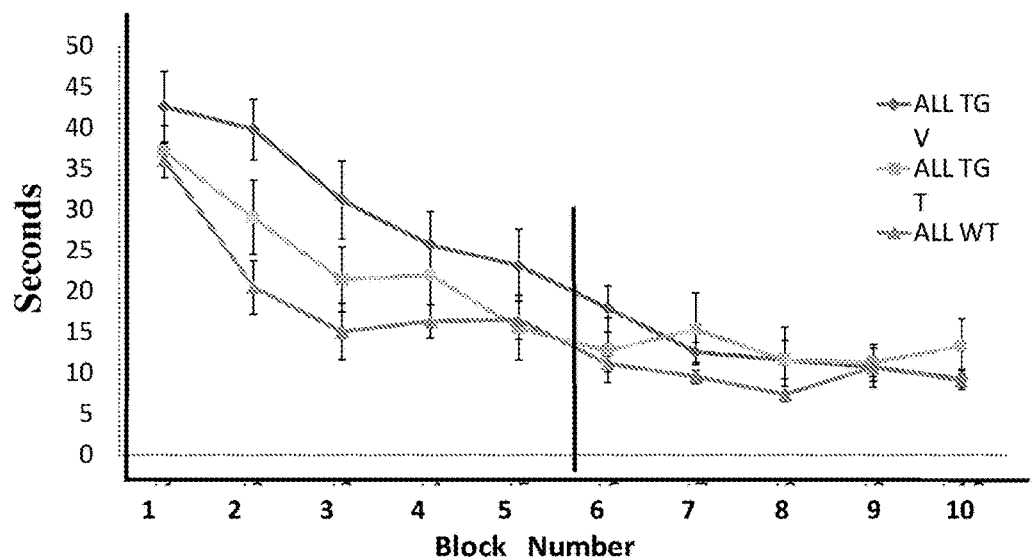
FIG. 20B demonstrates the effect of compound of Formula 1 on learning and memory of transgenic mice with Alzheimer's disease like symptoms using Radial Arm Water Maze test; total time per test is demonstrated as function of learning blocks.

Entry into an incorrect arm was scored as an error, and the times spent by the animal to find the platform were recorded. The results are demonstrated in the FIGS. 20A and 20B. FIG. 20A shows the number of errors, while FIG. 20B shows the total time spend in the water maze, as function of number of learning blocks. The number of errors data (FIG. 20A, data presented as mean±standard error of the mean) from RAWM was assessed using ANOVA test; a significant difference in animal's memory training between the three groups: WT-mice (n=18), 5XFAD/APOE (n=13) and 5XFAD/APOE treated with VBIT-4 (n=9) in different measurement times (trials) was obtained with F (9,159)=2.03 (p=0.03). To examine the source of differences the post-hoc test of Bonferroni-type was used. The non-transgenic mice trained better in comparison to non-treated TG mice (p=0.007). The TG mice treated with VBIT-4 performance was better than untreated TG and there was no difference between TG VBIT-4 treated group and the WT group. A trend for the improved performance (training) of the VBIT-4-TG treated group compared to non-treated TG group was seen (p=0.06).

The data of total time spent (FIG. 20B, data presented as mean±standard error of the mean) from RAWM was analyzed using repeated measures ANOVA test; a significant difference was obtained in animal's memory training between the three mouse groups: WT (n=18), 5XFAD/APOE (n=13) and 5XFAD/APOE treated with VBIT-4 (n=9) in different measurement times (trials), with F (2,35)=6.91,

The invention claimed is:

1. A compound of general formula (Id):

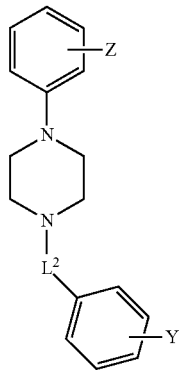

Formula (Id)

wherein
L² is a linking group selected from the group consisting of 4-hydroxybutanamidylene having the formula HO—CH₂—C*H—CH₂—C(O)NH—, wherein the asterisk denotes an attachment point and pyrrolidine-2,5-dionylene;
Z is $C_{1-2}$-perfluoroalkoxy, and Y is halogen;
or an enantiomer, diastereomer, mixture or salt thereof.

2. The compound of claim 1 having Formula 1:

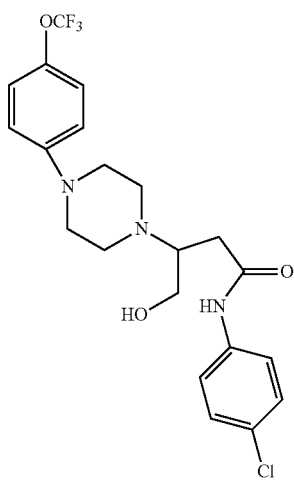

(Formula 1)

or an enantiomer, diastereomer, mixture or salt thereof.

3. The compound of claim 1 having Formula 2:

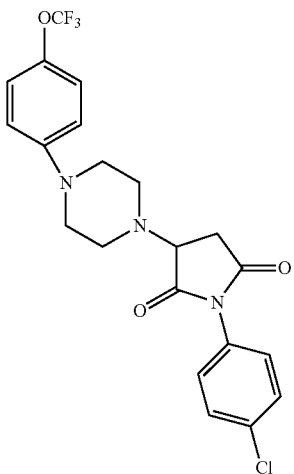

(Formula 2)

or an enantiomer, diastereomer, mixture or salt thereof.

4. A pharmaceutical composition containing the compound according to claim 1 together with one or more pharmaceutically acceptable excipients.

5. A method of making a medicament comprising formulating a compound according to claim 1 with one or more pharmaceutically acceptable excipients.

6. A method for treating a disease or disorder associated with enhanced apoptosis comprising administering to a subject in need thereof a therapeutically effective amount of the compound according to claim 1.

7. A method for treating a disease or disorder selected from the list consisting of neurodegenerative diseases and disorders, cardiovascular diseases and disorders, Alzheimer's disease, Parkinson's disease, cardiac hypertrophy, heart failure, myocardial infarction, ischemia/reperfusion injury, apoptosis, autophagy of cardiac myocytes, atrial fibrillation (AF), and cardiac arrhythmia comprising administering to a subject in need thereof a therapeutically effective amount of the compound according to claim 1.

* * * * *

UNITED STATES PATENT AND TRADEMARK OFFICE
CERTIFICATE OF CORRECTION

PATENT NO. : 10,508,091 B2  
APPLICATION NO. : 15/567807  
DATED : December 17, 2019  
INVENTOR(S) : Shoshan-Barmatz et al.

Page 1 of 1

It is certified that error appears in the above-identified patent and that said Letters Patent is hereby corrected as shown below:

In the Specification

Column 9 & 10, Table 1, Formula 1:

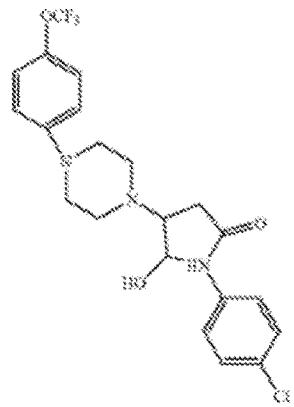

Should be:

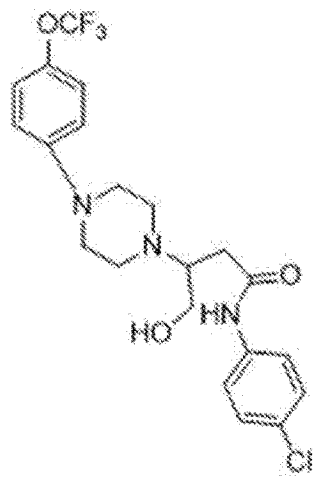

Signed and Sealed this  
Twentieth Day of October, 2020

Andrei Iancu  
*Director of the United States Patent and Trademark Office*